US009279157B2

(12) United States Patent
He et al.

(10) Patent No.: US 9,279,157 B2
(45) Date of Patent: Mar. 8, 2016

(54) EMX2 IN CANCER DIAGNOSIS AND PROGNOSIS

(75) Inventors: Biao He, So. San Francisco, CA (US); David M. Jablons, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 874 days.

(21) Appl. No.: 12/701,324

(22) Filed: Feb. 5, 2010

(65) Prior Publication Data

US 2010/0233703 A1 Sep. 16, 2010

Related U.S. Application Data

(60) Provisional application No. 61/150,627, filed on Feb. 6, 2009, provisional application No. 61/157,100, filed on Mar. 3, 2009.

(51) Int. Cl.

| C12Q 1/68 | (2006.01) |
|---|---|
| G01N 33/574 | (2006.01) |
| C07H 21/04 | (2006.01) |
| C12P 19/34 | (2006.01) |

(52) U.S. Cl.
CPC ........ *C12Q 1/6886* (2013.01); *G01N 33/57407* (2013.01); *G01N 33/57423* (2013.01); *C12Q 2600/106* (2013.01); *C12Q 2600/118* (2013.01); *C12Q 2600/154* (2013.01); *C12Q 2600/158* (2013.01); *C12Q 2600/16* (2013.01); *G01N 2800/54* (2013.01)

(58) Field of Classification Search
None
See application file for complete search history.

(56) References Cited

U.S. PATENT DOCUMENTS

| 2003/0124600 A1* | 7/2003 | Sidransky ........................... 435/6 |
|---|---|---|
| 2003/0143606 A1* | 7/2003 | Olek et al. ......................... 435/6 |
| 2005/0095607 A1* | 5/2005 | Erlander et al. .................. 435/6 |
| 2005/0119171 A1* | 6/2005 | Bejanin et al. .................. 514/12 |
| 2005/0260646 A1* | 11/2005 | Baker et al. ..................... 435/6 |
| 2006/0121476 A1* | 6/2006 | Petroziello et al. ............... 435/6 |
| 2006/0236421 A1* | 10/2006 | Pennell et al. ................. 800/278 |
| 2007/0128636 A1* | 6/2007 | Baker et al. ..................... 435/6 |
| 2007/0161029 A1* | 7/2007 | Li et al. .......................... 435/6 |
| 2007/0178445 A1* | 8/2007 | Eshleman et al. ................ 435/5 |
| 2007/0196840 A1* | 8/2007 | Taron Roca et al. .............. 435/6 |
| 2007/0274912 A1* | 11/2007 | Allis et al. ..................... 424/9.1 |
| 2007/0280969 A1* | 12/2007 | Shih et al. .................... 424/277.1 |
| 2007/0298431 A1* | 12/2007 | Mai ................................ 435/6 |
| 2007/0299030 A1* | 12/2007 | Dmitrovsky et al. ........... 514/44 |
| 2008/0021048 A1* | 1/2008 | Bennett et al. ........... 514/263.23 |
| 2008/0026415 A1* | 1/2008 | Rimm et al. .................... 435/15 |
| 2010/0240035 A1* | 9/2010 | Jablons et al. .................... 435/6 |

FOREIGN PATENT DOCUMENTS

DK EP 1895302 A2 * 3/2008 ....... G01N 33/57419

OTHER PUBLICATIONS

Stein et al. A database study that identifies genes whose expression correlates, negatively or positively, with 5-year survival of cancer patients. Biochimica et Biophysica Acta 1770:857-871 (2007).*
Su et al. Molecular classification signatures of human carcinomas by use of gene expression signatures. Cancer Research 61:7388-93 (2001).*
Winnepenninckx et al. Gene expression profiling of primary cutaneous melanoma and clinical outcome. Journal of the National Cancer Institute 98(7):472-482 (2006).*
Lind et al. Novel epigenetically deregulated genes in testicular cancer include homeobox genes and SCGB3A1(HIN-1). Journal of Pathology 210:441-449 (2006).*
Gangemi et al. Emx2 in adult neural precursor cells. Mechanisms of Development 109:323-329 (2001).*
Gangemi et al. Effects of Emx2 inactivation on the gene expression profile of neural precursors. European Journal of Neuroscience 23:325-334 (2006).*
Abate-Shen, "Deregulated Homeobox Gene Expression in cancer: cause or consequence?" Nat Rev Cancer, 2002, vol. 10, pp. 777-785.
Akiri et al. "Wnt pathway aberrations including autocrine Wnt activation occur at high frequency in human non-small-cell lung carcinoma," Oncogene, 2009, vol. 28, pp. 2163-2172.
Boersma et al. "Homeobox Proteins as Signal Transduction Intermediates in Regulation of NCAM Expression by Recombinant Human Bone Morphogenetic Protein-2 in Osteoblast-like Cells." Mol. Cell. Biol. Res. Commun., 1999, vol. 1, No. 2, pp. 117-124.
Clément et al. "Epigenetic alteration of the Wnt inhibitory factor-1 promoter occurs early in the carcinogenesis of Barrett's esophagus," Cancer Sci., 2008, vol. 99, No. 1, pp. 46-53.
Dalton et al. "Expression and embryonic function of empty spiracles: A *Drosophila* homeo box gene with two patterning functions on the anterior-posterior axis of the embryo," Genes and Development, 1989, pp: 1940-1956.
Donato, "S100: a multigenic family of calcium-modulated proteins of the EF-hand type with intracellular and extracellular functional roles," Intl J Biochem Cell Biol, 2001, vol. 33, pp. 637-668.
Fong, "Lung Cancer 9: Molecular biology of lung cancer: clinical implications," Thorax, 2003, vol. 58, pp. 892-900.
Galli et al. "Emx2 regulates the proliferation of stem cells of the adult mammalian central nervous system," Development, 2002, vol. 129, pp. 1633-1644.
Ganesan et al. "Inhibition of Gastric Cancer Invasion and Metastasis by PLA2G2A, a Novel β-Catenin/TCF Target Gene," Cancer Res, 2008, vol. 68, No. 11, pp. 4277-4286.
Harden et al. "Gene Promoter Hypermethylation in Tumors and Lymph Nodes of Stage I Lung Cancer Patients," Clin. Cancer Res., 2003, vol. 9, pp. 1370-1375.

(Continued)

*Primary Examiner* — Samuel Woolwine
(74) *Attorney, Agent, or Firm* — Morrison & Foerster LLP

(57) ABSTRACT

The present invention provides methods for determining a prognosis of disease free or overall survival in a patient suffering from cancer. The methods generally involve determining a normalized expression level of an EMX2 gene product, which correlates with prognosis and likelihood of survival.

22 Claims, 39 Drawing Sheets

(56) References Cited

OTHER PUBLICATIONS

He et al. "Secreated Frizzled-Related Protein 4 is Silenced by Hypermethylation and Induces Apoptosis in β-Catenin-Deficient Human Mesothelioma Cells," Cancer Res., 2005, vol. 65, No. 3, pp. 743-748.

He B et al., "A Monoclonal Antibody against Wnt-1 Induces Apoptosis in Human Cancer Cells," Neoplasia, 2004, vol. 6, pp. 7-14.

Heizmann et al., "S100 proteins: structure, functions and pathology," Front Biosci., 2002, vol. 7, pp. d1356-d1368.

Huang et al., "Wnt5a Expression Is Associated with the Tumor Proliferation and the Stromal Vascular Endothelial Growth Factor—an Expression in Non-Small-Cell Lung Cancer," J. Clin Oncol, 2005, vol. 23, pp. 8765-8773.

Huang et al. "Wnt1 overexpression promotes tumour progression in non-small cell lung cancer," Eur. J. Cancer, 2008, vol. 44, pp. 2680-2688.

Klaus et al. "Wnt signalling and its impact on development and cancer," Nat Rev Cancer, 2008, vol. 8, pp. 387-398.

Königshoff et al, "WNT Signaling in Lung Disease," Am J. Respir. Cell. Mol. Biol., 2010, vol. 42, pp. 2131.

Ligon et al. "Loss of EMx2 function leads to ectopic expression of Wnt1 in the developing telencephalon and cortical dysplasia," Development, 2003, vol. 130, pp. 2275-2287.

Lind Ge et al., "Novel epigenetically deregulated genes in testicular cancer include homeobox genes and SCGB3A1 (HIN-1)," J Pathol, 2006, vol. 210, pp. 441-449.

Marenholz et al., "S100 Proteins in mouse and man: from evolution to function and pathology (including an update of the nomenclature)" Biochem Biophys Res Commun, 2004, vol. 322, pp. 1111-1122.

Mazieres et al, "Wnt Inhibitory Factor-1 Is Silenced by Promoter Hypermethylation in Human Lung Cancer," Cancer Research, 2004, vol. 64, pp. 4717-4720.

Mcdonald et al., "The opposing roles of Wnt-5a in cancer," British J Cancer, 2009, vol. 101, No. 2, pp. 209-214.

Noonan et al., "Characterization of the Homeodomain Gene EMX2: Sequence Conservation, Expression Analysis, and a Search for Mutations in Endometrial Cancers," Genomics, 2001, vol. 76, pp. 37-44.

Noonan et al., "Antisense transcripts at the EMX2 locus in human and mouse," Genomics, 2003, vol. 81, pp. 58-66.

Raman V et al. "HOXA5 Regulates Expression of the Progesterone Receptor," J Biol Chem. 2000, vol. 275, No. 34, pp. 26551-26555.

Samuel et al., "Homebox gene expression in cancer: Insights from developmental regulation and deregulation," Eur. J. Cancer., 2005, vol. 16, pp. 2428-2437.

Stein et al. "The metastasis-associated gene S100A4 is a novel target of β-catenin/T-cell factor signaling in colon cancer," Gastroenterology, 2006, vol. 131, pp. 1486-1500.

Taylor, "Emx2 Regulates Mammalian Reproduction by Altering Endometrial Cell Proliferation," Mol. Endocrinol, 2005, vol. 19, No. 11. pp. 2839-2846.

Yoshida et al. "Deregulation of the HOXA10 Homeobox Gene in Endometrial Carcinoma: Role in Epithelial-Mesenchymal Transition," Cancer Res, 2006, vol. 2, pp. 889-897.

You et al. "Inhibition of Wnt-2-mediated signaling induces programmed cell death in non-small-cell lung cancer cells," Oncongene, 2004, vol. 23, pp. 6170-6174.

Zimmer et al., "Molecular mechanisms of S100-target protein interactions," Microsc Res Tech., 2003, vol. 60, No. 6, pp. 552-559.

Zöchbauer-Müller et al., "Fragile histidine triad (FHIT) gene abnormalitites in lung cancer," Clin Lung Cancer, 2000, vol. 2, pp. 141-145.

* cited by examiner

| Characteristics | Normal Lung (N = 65) | | | Adenocarcinoma and **BAC (N = 144) | | | |
|---|---|---|---|---|---|---|---|
| | Number | (%) | EMX2 Expression | Number | (%) | EMX2 Expression | p-value |
| Age | | | | | | | |
| Median | 64.3 ± 0.9 (years) | | | 67.6 ± 0.9 (years) | | | |
| Range | 36-85 (years) | | | 41-91 (years) | | | |
| Whole | 65 | (100%) | 17.99 ± 3.50 | 144 | (100%) | 21.36 ± 4.68 | |
| Young (<50) | 6 | (9.2%) | 27.35 ± 13.28 | 9 | (6.3%) | 6.36 ± 6.13 | |
| Middle (50≤, 75>) | 46 | (70.8%) | 18.83 ± 4.48 | 96 | (66.7%) | 20.79 ± 5.88 | |
| Old (≥75) | 13 | (20.0%) | 11.44 ± 4.87 | 39 | (26.7%) | 25.54 ± 12.29 | N.S. |
| Sex | | | | | | | |
| Male | 31 | (47.7%) | 20.44 ± 5.69 | 54 | (37.5%) | 15.34 ± 5.91 | |
| Female | 34 | (52.3%) | 15.75 ± 4.27 | 90 | (62.5%) | 24.97 ± 6.58 | p = 0.04 |
| Race | | | | | | | |
| Caucasian | 45 | (69.2%) | 16.26 ± 3.95 | 110 | (76.4%) | 20.20 ± 5.43 | |
| Asian | 14 | (21.5%) | 25.01 ± 9.50 | 22 | (15.3%) | 20.42 ± 13.60 | |
| Others | 6 | (9.2%) | 13.85 ± 9.79 | 11 | (7.6%) | 31.24 ± 20.21 | |
| Unknown | | | | 1 | (0.7%) | 13.63 | N.S. |
| Smoking | | | | | | | |
| Never | 12 | (18.5%) | 12.71 ± 6.50 | 33 | (22.9%) | 19.54 ± 8.20 | |
| Smoker | 50 | (76.9%) | 19.82 ± 4.26 | 107 | (74.3%) | 21.27 ± 5.73 | |
| Past | 27 | (41.5%) | 15.38 ± 4.26 | 68 | (47.2%) | 24.56 ± 8.22 | |
| Current | 23 | (35.4%) | 25.04 ± 7.76 | 39 | (27.1%) | 15.55 ± 6.50 | |
| Unknown | 3 | (4.6%) | 8.60 ± 7.05 | 4 | (2.8%) | 38.62 ± 21.72 | N.S. |
| Pack per year | | | | | | | |
| Median | 40.6 ± 4.8 | | | 34.4 ± 3.0 | | | |
| Range | 0 - 190 | | | 0 - 150 | | | |
| Sex, Smoking | | | | | | | |
| Male, Smoker | 26 | (40.0%) | 21.48 ± 6.45 | 46 | (31.9%) | 17.11 ± 6.91 | |
| Male, Non-Smoker | 4 | (6.2%) | 18.74 ± 14.86 | 8 | (5.6%) | 5.18 ± 2.66 | |
| Female, Smoker | 24 | (36.9%) | 18.03 ± 5.57 | 61 | (42.4%) | 24.41 ± 8.63 | |
| Female, Non-Smoker | 8 | (12.3%) | 9.70 ± 6.95 | 25 | (17.3%) | 24.14 ± 10.68 | |
| Unknown | 3 | (4.6%) | 8.60 ± 7.05 | 4 | (2.8%) | 38.62 ± 21.72 | N.S. |
| Tumor size | | | | | | | |
| Median | | | | 3.5 ± 0.3 (cm) | | | |
| Range | | | | 0.6 - 13.5 (cm) | | | |
| 3cm or less | | | | 76 | (52.8%) | 28.74 ± 8.02 | |
| over 3cm | | | | 67 | (46.5%) | 13.24 ± 4.11 | |
| Unknown | | | | 1 | (0.7%) | 3.79 | N.S. |
| Pathological Stage | | | | | | | |
| Normal | 65 | (100%) | 17.99 ± 3.50 | - | - | - | |
| Stage I | - | - | - | 91 | (63.2%) | 18.55 ± 4.29 | |
| Stage II | - | - | - | 17 | (11.8%) | 16.09 ± 11.19 | |
| Stage III | - | - | - | 25 | (17.4%) | 15.70 ± 8.57 | |
| Stage IV | - | - | - | 10 | (6.9%) | 72.00 ± 46.35 | |
| Unknown | - | - | - | 1 | (0.7%) | 1.52 | N.S. |
| Histology | | | | | | | |
| Adenocarcinoma | | | | 81 | (56.3%) | 26.03 ± 7.56 | |
| *BAC | | | | 63 | (43.7%) | 15.35 ± 4.42 | |
| Mixed BAC | | | | 42 | (29.1%) | 18.24 ± 5.34 | |
| Pure BAC | | | | 21 | (14.6%) | 9.57 ± 4.85 | N.S. |
| ECOG PS | | | | | | | |
| 0 | - | | | 76 | (52.8%) | 19.31 ± 4.90 | |
| 1 | - | | | 29 | (20.1%) | 11.18 ± 6.53 | |
| 2 | - | | | 6 | (4.2%) | 1.73 ± 0.70 | |
| Unknown | - | | | 33 | (22.9%) | 38.60 ± 15.80 | N.S. |
| Operation Procedure | | | | | | | |
| Wedge Resection | | | | 13 | (9.0%) | 48.31 ± 33.91 | |
| Segmentectomy | | | | 5 | (3.5%) | 15.77 ± 13.23 | |
| Lobectomy | | | | 110 | (76.5%) | 19.71 ± 4.43 | |
| Bilobectomy | | | | 7 | (4.9%) | 17.45 ± 14.72 | |
| Pneumonectomy | | | | 6 | (4.1%) | 11.23 ± 11.07 | N.S. |
| Chemotherapy | | | | | | | |
| Yes | | | | 69 | (47.9%) | 22.87 ± 6.02 | |
| No | | | | 74 | (51.4%) | 20.21 ± 7.20 | |
| N/A | | | | 1 | (0.7%) | 2.15 | N.S. |
| Vital Status | | | | | | | |
| Alive | | | | 91 | (63.2%) | 30.51 ± 7.36 | |
| Dead | | | | 53 | (36.8%) | 5.64 ± 1.91 | p = 0.003 |
| Recurrence | | | | | | | |
| Positive | | | | 55 | (38.2%) | 6.48 ± 2.11 | |
| Negative | | | | 74 | (51.4%) | 22.75 ± 5.46 | p = 0.007 |
| Follow up: months | | | | | | | |
| Median | | | | 41.6 ± 2.3 (months) | | | |
| Range | | | | 0.1 - 117.3 (months) | | | |

FIG. 4

*; Eastern Cooperative Oncology Group performance status
**; Bronchioloalveolar carcinoma

| Variable | Hazard Ratio | (95%CI*) | p-value |
|---|---|---|---|
| EMX2 Expression | | | |
| High Expression Group | 0.44 | 0.23-0.85 | 0.02 |
| Pathological stage (compared to Stage I) | | | 0.03 |
| Stage II | 0.81 | 0.71-1.04 | 0.03 |
| Stage III | 1.36 | 0.50-3.72 | 0.55 |
| Stage IV | 2.47 | 1.13-5.41 | 0.02 |
| | 3.88 | 1.41-10.69 | 0.009 |
| Histology | | | |
| BAC (compared to Adenocarcinoma) | 0.60 | 0.80-4.90 | 0.12 |

FIG. 5

| Gene | Forward Primer | Reverse Primer | Probe |
|---|---|---|---|
| RT-PCR GAPDH | 5'-GATATCTGGGTCATCGCTTC-3' | 5'-TGAGTTTCCGTGAGGCTGAG-3' | |
| EMX2 | 5'-GATATCTGGGTCATCGCTTC-3' | 5'-TGAGTTTCCGTGAGGCTGAG-3 | |
| WNT1 | 5'-CTGCAGCGACAACATTGACT-3' | 5'-CGTGGCACTTGCACTCCT-3' | |
| WNT2 | 5'-GGATGCCAGAGCCCTGATGAATCTT-3' | 5'-GCCAGCCAGCATGTCCTGAGAGTA-3' | |
| WNT3 | 5'-ATCATAAGGGGCCGCCTGGCGAA-3' | 5'-ATGAGCGTGTCACTGCAAAG-3' | |
| WNT3A | 5'-CAAGATTGGCATCCAGGAGT-3' | 5'-ATGAGCGTGTCACTGCAAAG-3' | |
| WNT5A | 5'-AGGGCATTACTTGTTCGTTA-3' | 5'-GAACATATTTGATGGCCTGT-3' | |
| WNT16 | 5'-TGTCCAGTATGGCATGTGGT-3' | 5'-TTCCAGCATGTTTTCACAGC-3' | |
| qPCR GAPDH | Hs99999905_m1 | | |
| EMX2 | Hs00244574_m1 | | |
| qMSP ATCB | 5'-TGGTGATGGAGGAGGTTTAGTAAGT-3 | 5'-AACCAATAAAACCTACTCCTCCCTTAA-3' | 6 FAM5'-ACCACCACCCAACACACAATAACAAACACA-3' |
| EMX2 | 5-ATTCGGATTTGGTGTTCGTC-3 | 5'-CGAATCCCGCTACTACGAAAA-3' | 6 FAM5'-TATTCGGTGTCGTCGTCGTACG-TAMRA-3' |

FIG. 20

Table S1. Primers and Probes Used in RT-PCR and qMSP

| | Gene | Forward Primer | Reverse Primer | Probe |
|---|---|---|---|---|
| RT-PCR | GAPDH | GATATCTGGGTCATCGCTTC | TGAGTTTCCGTGAGGCTGAG | |
| | EMX2 | GATATCTGGGTCATCGCTTC | TGAGTTTCCGTGAGGCTGAG | |
| | WNT1 | CTGCAGCGACAACATTGACT | CGTGGCACTTGCACTCCT | |
| | WNT2 | GGATGCCAGAGCCCTGATGAATCTT | GCCAGCCAGCATGTCCTGAGAGTA | |
| | WNT3 | ATCATAAGGGGCCGCCTGGCGAA | ATGAGCGTGTCACTGCAAAG | |
| | WNT3A | CAAGATTGGCATCCAGGAGT | ATGAGCGTGTCACTGCAAAG | |
| | WNT5A | AGGGCATTACTTGTTCGTTA | GAACATATTTGATGGCCTGT | |
| qPCR | GAPDH | Hs99999905_m1 | | |
| | EMX2 | Hs00244574_m1 | | |
| | WNT1 | Hs01011247_m1 | | |
| | WNT2 | Hs01128652_m1 | | |
| | WNT3 | Hs00902257_m1 | | |
| | WNT3A | Hs01055707_m1 | | |
| | WNT5A | Hs00180103_m1 | | |
| | β-catenin | Hs99999168_m1 | | |
| qMSP | ATCB | TGGTGATGGAGGAGGTTTAGTAAGT | AACCAATAAAACCTACTCCTCCCTTAA | ACCACCACCCAACACACAATAAGAAACACA |
| | EMX2 | ATTCGGATTTGGTGTTCGTC | CGAATCCCGCTACTACGAAA | TATTCGGTGTCGTCGTCGTACG |

*FIG. 26*

EMX2 IN CANCER DIAGNOSIS AND PROGNOSIS

CROSS-REFERENCES TO RELATED APPLICATIONS

This application claims priority to U.S. Provisional Patent Application No. 61/150,627, filed Feb. 6, 2009, and to U.S. Provisional Patent Application No. 61/157,100, filed Mar. 3, 2009, the contents of all of the above are incorporated by reference in the entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 220002076000SeqList.txt, date recorded: Jul. 27, 2015, size: 6 KB).

BACKGROUND OF THE INVENTION

Prognosis in clinical cancer is an area of great concern and interest. It is important to know the aggressiveness of malignant cells and the likelihood of tumor recurrence or spread in order to plan the most effective therapy. Certain cancers are managed by alternative strategies. In some cases local-regional therapy is utilized, while in other cases when spread of disease is detected or suspected, systemic therapy is instituted.

Inactivation of tumor suppression genes is an important event contributing to the development of neoplastic malignancies. In addition to the classical genetic mechanisms involving deletions or activating point mutations, growth regulatory genes can be functionally inactivated or otherwise modulated by epigenetic alterations. These may involve alterations in the genome other than the DNA sequence itself, which include genomic hypomethylations, promoter-related hypermethylation (e.g., of CpG dinucleotides, and CpG islands), histone deacetylation and chromatin modifications. Molecular analysis of tumor-derived genetic and epigenetic alterations may have a profound impact on cancer diagnosis and monitoring for tumor recurrence.

DNA methylation is a naturally-occurring epigenetic modification that occurs in a cytosine base followed by a guanosine base (CpG). In general, CpG hypermethylation is thought to be associated with transcriptional silencing. It is believed that methylation can result in recruitment of methylation binding proteins (MBPs) and histone deacetylation of, for example, tumor suppressor genes, inactivating them and allowing tumors to form.

A need exists in the art for methods and tests that provide predictive information about patient prognosis and likelihood of survival. More particularly, methods are needed for identifying and statistically correlating altered gene expression with a specific stage of cancer.

BRIEF SUMMARY OF THE INVENTION

The present invention provides methods for determining a prognosis of disease free or overall survival in a patient suffering from cancer. The methods generally involve determining a normalized expression level of an EMX2 gene product, which correlates with prognosis and likelihood of survival.

In one aspect, this invention provides a method of predicting the likelihood of survival without cancer recurrence for a patient having cancer. The method comprises these steps: (a) assaying an expression level of an EMX2 RNA transcript or its expression product in a biological sample comprising a cancer cell obtained from said patient, except that the sample is not from endometrial or testicular tissue of the patient, and the expression level of the EMX2 RNA transcript or its expression product directly correlates with a likelihood of cancer survival of the patient; and (b) providing information including an estimate of the likelihood of survival, which includes and relates to the expression level of the EMX2 RNA transcript or its expression product.

In some embodiments, step (a) further comprises comparing the expression level of EMX2 RNA or expression product from the biological sample comprising the cancer cell with the expression level of EMX2 RNA or expression product from a normal control. When a decrease in the expression level of EMX2 RNA or expression product is observed as compared to the expression level from the normal control, a likelihood of cancer recurrence is indicated.

In other embodiments, step (a) is performed on the biological samples from two or more subjects, and the estimate in step (b) indicates a lower likelihood of survival when a larger decrease is observed in step (a), whereas a smaller decrease suggests a higher likelihood of survival. In some cases, the estimate of likelihood of survival is an estimate of a likelihood of disease-free survival.

The claimed method can be practice to assess patients suffering from cancers such as lung, colon, skin, and esophageal cancer, especially non-small cell lung carcinoma, adenocarcinoma, mesothelioma, or bronchioloalveolar carcinoma.

In other embodiments, step (a) involves determining the normalized expression level of the EMX2 RNA transcript or its expression product, for example, by semi-quantitative real-time PCR (RT-PCR). In other embodiments, step (a) involves determining a level of EMX2 promoter methylation, and EMX2 promoter methylation is inversely correlated with the expression level of EMX2 RNA transcript or its expression product. In the alternative, the expression level is determined by measuring a level of EMX2 protein in a sample.

In some embodiments of the claimed method, step (b) involves generating a report comprising the information comprising an estimate of likelihood of survival, for example, the report may include information regarding treatment options for cancers according to an expression level of the EMX2 RNA transcript or its expression product.

In a second aspect, the present invention also provides a kit for predicting the likelihood of survival without cancer recurrence for a patient having cancer. A kit used for determining EMX2 RNA level generally includes two main components: PCR primers for quantitatively determining the amount of EMX2 RNA transcript in a biological sample comprising a cancer cell obtained from the patient; and a standard control representing the amount of EMX2 RNA transcript in a sample of the same tissue type from an average person without cancer.

Similarly, a kit used for determining EMX2 protein level generally includes two main components: an antibody for quantitatively determining the amount of EMX2 protein in a biological sample comprising a cancer cell obtained from the patient; and a standard control representing the amount of EMX2 protein in a sample of the same tissue type from an average person without cancer. In either version of the kits, these components are typically kept in separate containers or vials. Instruction manuals for users are also typically included in the kits.

BRIEF DESCRIPTION OF THE DRAWINGS

FIG. 1, Panel B is a second bar graph which shows the extent of EMX2 promoter methylation in the same 12 NSCLC cell lines as a normalized percentage (%) of EMX2 promoter methylation in H1703 (set as 100%), determined by quantitative methylation specific PCR (qMSP). Read in conjunction with one another, Panels A and B illustrate that the extent of EMX2 promoter methylation negatively correlates with the extent of EMX2 gene expression in all lung cancer cell lines examined. Thus, a high degree of promoter methylation is associated with low EMX2 expression levels, and vice versa.

FIG. 4 is a table summarizing the EMX2 expression status in NSCLC patients having adenocarcinoma and/or bronchioloalveolar carcinoma as compared to healthy subjects. 65 normal lung patients and 144 affected patients gave tissue samples. As above, RT-PCR was used to ascertain gene expression levels and qMSP was used to determine the extent of EMX2 promoter methylation. After EMX2 expression and methylation was evaluated in the normal and affected groups, significant differences were revealed. For example, females and living patients had significantly higher EMX2 expression levels. In contrast, patients with recurrent cancer had low EMX2 expression levels.

FIG. 5 is a table summarizing the Hazard Ratios (HR) of groups of patients separated by EMX2 expression levels. In survival analysis, HR is an estimate of the likelihood of survival. HR increases with increasingly severe pathological stage. Here, tissue samples were taken from lung cancer patients and separated into low and high expressing groups. High EMX2 expressing groups demonstrate a low HR, indicating a higher likelihood of survival for individuals in that group. Consistently high EMX2 expression levels are significantly associated with overall survival.

FIG. 11 Panel B shows increased proliferation of the A427 cell line upon transfection with EMX2 shRNA. This is compared to proliferation levels of control shRNA transfected cells. Consistently, colony formation assays showed a significantly increased number of colonies after shRNA-knockdown of EMX2 expression.

FIG. 20 is a table including information regarding the primers (SEQ ID NOS:3-18, 20 and 21) and probes (SEQ ID NOS:19 and 22) used for RT-PCR experiments which were obtained from Operon Biotechnologies.

FIG. 26. Primers (SEQ ID NOS:3-14, 17, 18, 20 and 21) and probes (SEQ ID NOS:23 and 24) used in RT-PCR and qMSP FIG. 27. Knock-down of EMX2 in human lung cancer cell line A427 stably transfected with EMX2 shRNA construct #2 (sequence is described in Materials and Methods). (A) Quantitative RT-PCR of EMX2 gene. GAPDH served as RNA control and normalization. (B) TOP/FOP assay of the canonical WNT pathway transcription activity. (C) Cell proliferation MTS assay in A427 cells stably transfected with EMX2 shRNA #2 (solid squares and dashed line) and non-silencing shRNA (solid diamonds and solid line). (D) Colony formation assay. Controls were set as 100%. The data shown are the means of triplicate with error bars (S.D.).

DEFINITIONS

Figure 1:
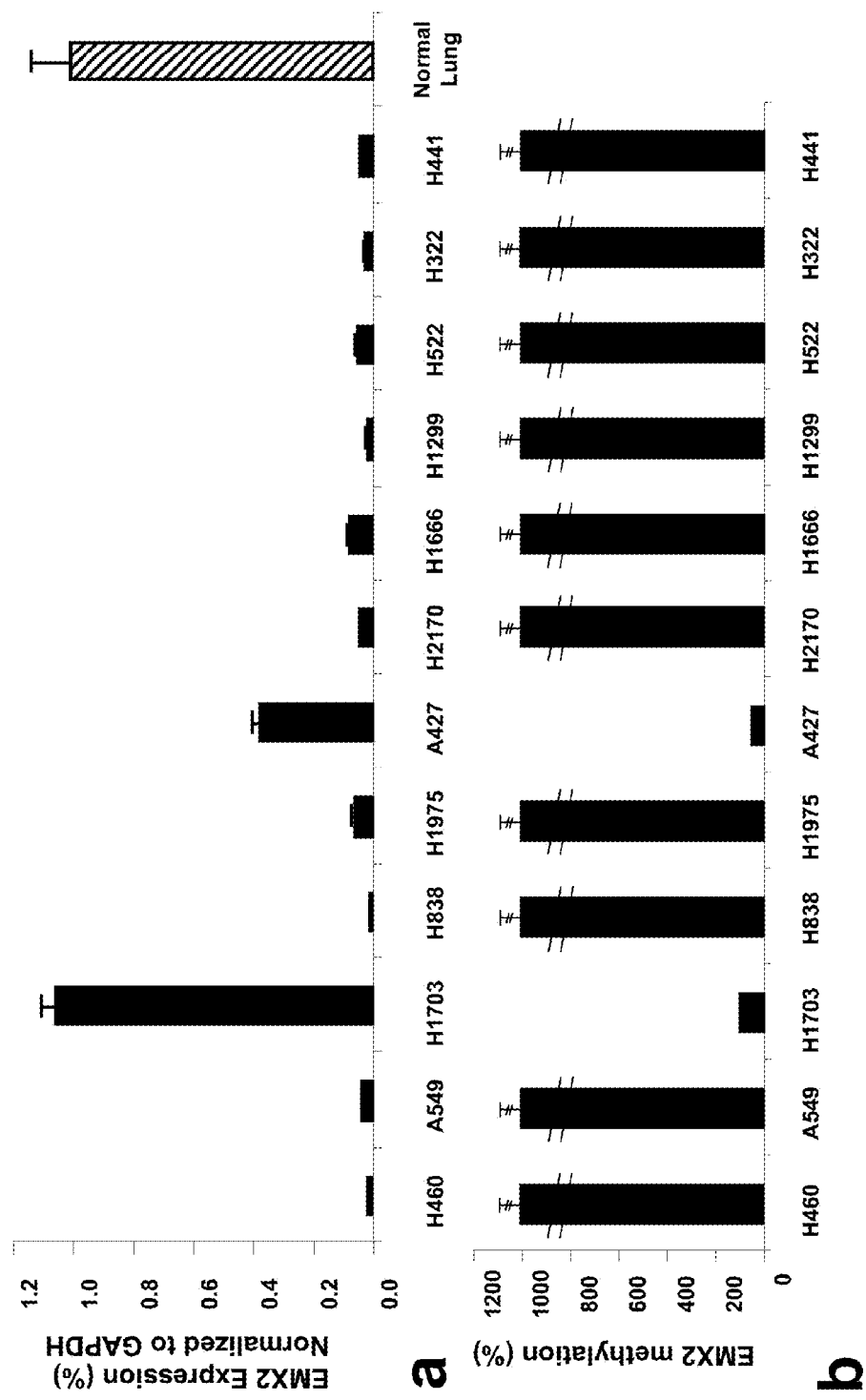
FIG. 1 presents two bar graphs which show that hyper-methylation in the promoter region of EMX2 correlates with down-regulation of EMX2 expression in non-small cell lung carcinoma ("NSCLC") cell lines. The bar graph in Panel A depicts normalized EMX2 expression levels (y-axis) in 12 different NSCLC cell lines (x-axis) as compared to normal lung. The relative expression levels were determined by semi-quantitative real-time PCR (RT-PCR). Glyceraldehyde 3-phosphate dehydrogenase ("GAPDH"), a housekeeping gene that is constitutively expressed at high levels in most tissues, was used as an internal control for normalization calculations. EMX2 expression was lost in almost all lung cancer cell lines examined as compared to the normal lung tissue control, with the exception of the H1703 and A427 lines.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, an "EMX2 gene" refers to a nucleic acid that encodes an EMX2 gene product, e.g., an EMX2 RNA, an EMX2 polypeptide, and the like. In one embodiment EMX2 has the sequence shown in Accession number AAM75387 or CAA48751.

The terms "methylation" and "hyper-methylation" are used interchangeably herein to refer to methyl group modification(s) in the polynucleotide of at least one gene, most often within the promoter of a gene, whose methylation status is linked to the incidence of cancer.

As used herein, the term "methylation status" is used to indicate the presence or absence or the level or extent of methyl group modification in the polynucleotide of at least one gene. As used herein, "methylation level" is used to indicate the quantitative measurement of methylated DNA for a given gene, defined as the percentage of total DNA copies of that gene that are determined to be methylated, based on quantitative methylation-specific PCR. The subject methods comprise determining the methylation status and level of a gene such as EMX2 in a test subject.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having cancer (e.g., colorectal cancer), including those who have undergone or are candidates for resection (surgery) to remove cancerous tissue (e.g., cancerous colorectal tissue).

As used herein, the terms "treatment," "treating," and the like, refer to administering an agent, or carrying out a procedure (e.g., radiation, a surgical procedure, etc.), for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. In tumor (e.g., cancer) treatment, a therapeutic agent may directly decrease the pathology of tumor cells, or render the tumor cells more susceptible to treatment by other therapeutic agents, e.g., radiation and/or chemotherapy.

The term "long-term" survival is used herein to refer to survival for at least 5 years, following surgery or other treatment.

The term "tumor," as used herein, refers to all neoplastic cell growth and proliferation, whether malignant or benign, and all pre-cancerous and cancerous cells and tissues.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. In general, cells of interest for detection, analysis, classification, or treatment in the present application include precancerous (e.g., benign), malignant, pre-metastatic, metastatic, and non-metastatic cells. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, esophageal cancer, mesothelioma, leukemia, melanoma, head and neck cancer, and brain cancer.

Depending on the nature of the cancer, an appropriate patient sample is obtained. As used herein, the phrase "cancerous tissue sample" refers to any cells obtained from a cancerous tumor. In the case of solid tumors which have not metastasized, a tissue sample from the surgically removed tumor will typically be obtained and prepared for testing by conventional techniques. Alternatively, a body fluid sample, such as lymph, blood or serum sample, or an exudate fluid sample such as the cancerous organ exudate (e.g., exudate from the breast) may be collected and used as the sample to be analyzed. In the case of leukemias, lymphocytes or leukemic cells will be obtained and appropriately prepared. Similarly, in the case of any metastasized cancer, cells may be drawn from a body fluid such as lymphatic fluid, blood, serum, or a distally infected organ or exudate thereof. While EMX2 expression levels will typically be measured within the cancerous cells of a patient, expression levels of EMX2 will also be measured in a body fluid sample (e.g., serum) as a result of EMX2 having been secreted or otherwise released from cells (e.g., by cell rupture).

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Therefore, the present invention contemplates a method of determining the risk of further growth of one or more cancerous tumors in an organ or body part which is not directly connected to the organ of the original cancerous tumor.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis.

The term "diagnosis" is used herein to refer to the identification of a molecular or pathological state, disease or condition, such as the identification of a molecular subtype of head and neck cancer, colon cancer, or other type of cancer. The term "prognosis" is used herein to refer to the prediction of the likelihood of cancer-attributable death or progression, including recurrence, metastatic spread, and drug resistance, of a neoplastic disease, such as lung, colon, skin or esophageal cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

A "biological sample" encompasses a variety of sample types obtained from an individual. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The terms "gene product" and "expression product" are used interchangeably herein in reference to a gene, to refer to the RNA transcription products (transcripts) of the gene, including mRNA and the polypeptide translation products of such RNA transcripts, whether such product is modified post-translationally or not. The terms "gene product" and "expression product" are used interchangeably herein, in reference to an RNA, particularly an mRNA, to refer to the polypeptide translation products of such RNA, whether such product is modified post-translationally or not. A gene product can be, for example, an unspliced RNA, an mRNA, a splice variant mRNA, a polypeptide, a post-translationally modified polypeptide, a splice variant polypeptide, etc.

The term "normalized" with regard to a gene transcript or a gene expression product refers to the level of the transcript or gene expression product relative to the mean levels of transcripts/products of a set of reference genes, wherein the reference genes are either selected based on their minimal variation across, patients, tissues or treatments ("housekeeping genes"), or the reference genes are the totality of tested genes. In the latter case, which is commonly referred to as "global normalization", it is important that the total number of tested genes be relatively large, preferably greater than 50. Specifically, the term 'normalized' with respect to an RNA transcript refers to the transcript level relative to the mean of transcript levels of a set of reference genes. More specifically, the mean level of an RNA transcript as measured by TAQ-MAN RT-PCR refers to the cycle threshold ("Ct") value minus the mean Ct values of a set of reference gene transcripts.

The lower the Ct, the greater the amount of mRNA present in the sample. The expression value of a RNA transcript in a sample is normalized, e.g., by first determining the mean expression value in Ct of designated reference genes in a sample ($Ct_{Ref}$). The normalized expression value for a gene ($Ct_{Gene}$) is then calculated as $Ct_{Gene}$–Ct $Ct_{Ref}$. Optionally, the normalized expression values for all genes can be adjusted, e.g., so that all adjusted normalized Ct have a value >0.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal ion concentration, and salt concentration. Primers are generally of a length compatible with their use in synthesis of primer extension products, and can be in the range of between about 8 nucleotides and about 100 nucleotides (nt) in length, such as about 10 nt to about 75 nt, about 15 nt to about 60 nt, about 15 nt to about 40 nt, about 18 nt to about 30 nt, about 20 nt to about 40 nt, about 21 nt to about 50 nt, about 22 nt to about 45 nt, about 25 nt to about 40 nt, and so on, e.g., in the range of between about 18 nt and about 40 nt, between about 20 nt and about 35 nt, between about 21 and about 30 nt in length, inclusive, and any length between the stated ranges. Primers can be in the range of between about 10-50 nucleotides long, such as about 15-45, about 18-40, about 20-30, about 21-25 nt and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19, or 20 more nucleotides either 5' or 3' from either termini or from both termini.

Primers are in many embodiments single-stranded for maximum efficiency in amplification, but may alternatively be double-stranded. If double-stranded, the primer is in many embodiments first treated to separate its strands before being used to prepare extension products. This denaturation step is typically affected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the covalent addition of bases at its 3' end.

As used herein, the term "probe" or "oligonucleotide probe", used interchangeably herein, refers to a structure comprised of a polynucleotide, as defined above, which contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with their use in specific detection of all or a portion of a target sequence of a target nucleic acid, and are in many embodiments in the range of between about 8 nt and about 100 nt in length, such as about 8 to about 75 nt, about 10 to about 74 nt, about 12 to about 72 nt, about 15 to about 60 nt, about 15 to about 40 nt, about 18 to about 30 nt, about 20 to about 40 nt, about 21 to about 50 nt, about 22 to about 45 nt, about 25 to about 40 nt in length, and so on, e.g., in the range of between about 18-40 nt, about 20-35 nt, or about 21-30 nt in length, and any length between the stated ranges. In some embodiments, a probe is in the range of between about 10-50 nucleotides long, such as about 15-45, about 18-40, about 20-30, about 21-28, about 22-25 and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length. In this context, the term "about" may be construed to mean 1, 2, 3, 4, 5, 6, 7, 8, 9, 10, 11, 12, 13, 14, 15, 16, 17, 18, 19, or 20 more nucleotides either 5' or 3' from either termini or from both termini.

Where a nucleic acid is said to hybridize to a recited nucleic acid sequence, hybridization is under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, e.g., at least about 90% as stringent as the above specific stringent conditions.

The term "microarray" refers to an ordered arrangement of addressable, hybridizable array elements, preferably polynucleotide probes, on a substrate.

The term "polynucleotide," when used in the singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

The term "housekeeping gene" refers to a group of genes that codes for proteins whose activities are essential for the maintenance of cell function. These genes are typically similarly expressed in all cell types. Housekeeping genes include, without limitation, glyceraldehyde-3-phosphate dehydrogenase (GAPDH), Cyp1, albumin, actins, e.g. β-actin, tubulins, cyclophilin, hypoxantine phsophoribosyltransferase (HRPT), L32, 28S, and 18S.

As used in this application, an "increase" or a "decrease" refers to a detectable positive or negative change in quantity from an established standard control. An increase is a positive change of at least 10%, 20%, 30%, or 50%, preferably at least 2-fold, more preferably at least 5-fold, and most preferably at least 10-fold of the control value. Similarly, a decrease is a negative change preferably at least 10%, 20%, 25%, 30%, 40%, or 50%, more preferably at least 80%, and most preferably at least 90% of the control.

"Standard control" or "normal control" as used herein refers to the average level of EMX2 expression, either in EMX2 RNA transcript or EMX2 protein, found in a sample that is obtained from the same type of tissue (but non-cancerous) as the biological sample obtained from a patient who is undergoing testing for assessing likelihood of survival. The standard control value is typically derived from the EMX2 expression level observed in a randomly selected group of cancer-free persons, especially those who do not suffer from the specific type of cancer relevant to the patient who is being assessed for likelihood of future survival. This selected group should comprise a sufficient number of healthy subjects such that the average level of EMX2 expression among these individuals reflects, with reasonable accuracy, the corresponding expression level in the general population of healthy, cancer-free persons.

DETAILED DESCRIPTION OF THE INVENTION

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an EMX2 gene product" includes a plurality of splice variants the EMX2 gene.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

I. Diagnosing and Assessing a Prognosis of Overall Survival in Cancer Patients

The present invention provides methods for diagnosing and determining a prognosis of disease-free or overall survival in a patient suffering from cancer, methods for determining the proper course of treatment for a patient suffering from cancer, and kits for use in practicing the same.

II. Determining Levels of EMX2 Gene Expression

EMX2 expression of a tumor is directly correlated with a subject's likelihood of survival, including tumor recurrence and/or aggressiveness. For example, a higher likelihood of disease-free or overall survival correlates with higher normalized values of EMX2 gene expression, higher EMX2 polypeptide levels, and low normalized values of EMX2 promoter methylation. Conversely, ow normalized values of EMX2 mRNA, polypeptide levels, as well as hyper-methylation of the EMX2 promoter region, correlate poor prognosis. Thus, the level of EMX2 expression may be used as the sole factor, or in combination with additional factors, such as lymph node status, in assessing the disease status and prognosis of cancer patients.

Determination of EMX2 gene expression levels may be performed by one or more of the following exemplary methods known to one of ordinary skill in the art. For example, EMX2 expression levels may be determined by (a) detection of an EMX2 gene product, such as mRNA encoding an EMX2 protein; (b) detection of the extent of EMX2 promoter methylation, where hypermethylation correlates with low expression levels; and (c) detection of an EMX2 polypeptide. Any combination of these techniques can be used to assess patient prognosis and likelihood of overall survival.

A. Detecting and Quantifying mRNA Encoding an EMX2 Protein

Detection of levels of mRNA encoding EMX2 serves as an indicator of EMX2 expression. Methods used to detect mRNA levels include the detection of hybridization or amplification with the mRNA encoding EMX2. In general, this detection may be carried out by analysis of mRNA either in vitro or in situ (e.g., in a tissue sample) using one of the methods known to one of ordinary skill in the art as exemplified in Ausubel et al., *Current Protocols in Molecular Biology* (John Wiley & Sons, 1999); in U.S. Pat. No. 5,882,864; and the like.

B. Sample Extraction and Preparation

The first step in the determination of EMX2 gene expression levels through detection EMX2 mRNA, is the isolation of mRNA from a patient sample. The sample can be any suitable biological sample from the subject which is suspected of containing cancer cells. Methods for obtaining samples and isolated mRNA are known in the art. For example, with respect to solid tumors, isolation may be performed by for example, core needle biopsy, fine needle aspiration, and the like. While the source of mRNA is a primary tissue, mRNA can be extracted, for example, from stored samples, e.g., from frozen or archived paraffin-embedded and fixed (e.g. formalin-fixed) tissue samples. RNA can be isolated from a variety of primary tumors, including lung, colon, intestine, stomach, breast, prostate, brain, skin, esophagus, mesothelial, blood cells, liver, kidney, pancreas, spleen, thymus, testis, ovary, uterus, head and neck tumors, etc., or from tumor cell lines.

After a biological sample is obtained and processed as may be desired, it is then subjected to a detection method that is compatible with the gene product to be assessed (e.g., RNA transcript or expression product thereof, or EMX2 gene methylation status).

C. Detection Methods

Any suitable detection method can be used to detect RNA transcripts in a sample. Some of the most commonly used methods known in the art for the quantification of mRNA expression in a sample include northern blotting and in situ hybridization (Parker & Barnes, *Methods in Molecular Biology* 106:247-283 (1999)); RNAse protection assays (Hod., *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Other suitable methods for assaying a level of a nucleic acid gene product include, e.g., microarrays; serial analysis of gene expression (SAGE); MassARRAY analysis; gene expression by massively parallel signature sequencing (see, e.g., Brenner et al., *Nature Biotechnology* 18:630-634 (2000); and the like.

Methods for RNA extraction from paraffin embedded tissues are disclosed, for example, in Rupp and Locker, *Lab Invest.* 56:A67 (1987), and De Andres et al., *BioTechniques* 18:42044 (1995). In particular, RNA isolation can be performed using a purification kit, buffer set and associated proteases from commercial manufacturers, such as Qiagen, according to the manufacturer's instructions. For example, total RNA from cells in culture can be isolated using Qiagen RNeasy mini-columns. Other commercially available RNA isolation kits include MASTERPURE Complete DNA and RNA Purification Kit (EPICENTRE, Madison, Wis.), and Paraffin Block RNA Isolation Kit (Ambion, Inc.). Total RNA from tissue samples can be isolated using RNA Stat-60 (Tel-Test). RNA prepared from tumor samples can also be isolated, for example, by cesium chloride density gradient centrifugation.

RT-PCR

Of the techniques listed above, RT-PCR is commonly used. RT-PCR can be used to compare mRNA levels in different sample populations, in normal and tumor tissues, to characterize patterns of gene expression, to discriminate between closely related mRNAs, and to analyze RNA structure.

Since RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQ-MAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signals from the released reporter dye are free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipment, such as, for example, ABI PRISM 7700 SEQUENCE DETECTION SYSTEM (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700 SEQUENCE DETECTION SYSTEM. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

A more recent variation of the RT-PCR technique is the real time quantitative PCR, which measures PCR product accumulation through a dual-labeled fluorigenic probe (i.e., TAQ-MAN probe). Real time PCR is compatible both with quantitative competitive PCR, where internal competitors for each target sequence are used for normalization, and with quantitative comparative PCR using a normalization gene contained within the sample, or a reference gene for RT-PCR. For further details see, e.g. Held et al., *Genome Research* 6:986-994 (1996).

Factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. can be used.

For further guidelines for PCR primer and probe design see, e.g. Dieffenbach, C. W. et al., "General Concepts for PCR Primer Design" in: *PCR Primer, A Laboratory Manual*, Cold Spring Harbor Laboratory Press, New York, 1995, pp. 133-155; Innis and Gelfand, "Optimization of PCRs" in: *PCR Protocols, A Guide to Methods and Applications*, CRC Press, London, 1994, pp. 5-11; and Plasterer, T. N. "Primerselect: Primer and probe design." *Methods Mol. Biol.* 70:520-527 (1997), the entire disclosures of which are hereby expressly incorporated by reference.

D. Assaying Promoter Methylation Status

Determining the extent of EMX2 promoter methylation may also serve as an indicator of EMX2 gene expression. In general, determining the methylation state of nucleic acid includes amplifying nucleic acids by means of oligonucleotide primers that distinguished between methylated and unmethylated nucleic acids. Methylation specific PCR (MSP) is described in U.S. Pat. Nos. 5,786,146, 6,200,756, 6,017,704 and 6,265,171, each of which is incorporated herein by reference in its entirety.

For example, DNA from a normal tissue surrounding a polyp can be amplified with two or more different unlabeled or randomly labeled primer sets in the same amplification reaction. The reaction products can be separated on, for example, a denaturing polyacrylamide gel and subsequently exposed to film or stained with ethidium bromide for visualization and analysis.

Examples of types of assays used to assess the methylation pattern include, but are not limited to, Southern blotting, single nucleotide primer extension, methylation-specific polymerase chain reaction (MSPCR), restriction landmark genomic scanning for methylation (RLGS-M) and CpG island microarray, single nucleotide primer extension (SN-uPE), and combined bisulfite restriction analysis (COBRA). The COBRA technique is disclosed in Xiong, Z. et al., *Nucleic Acids Research*, 25(12):2532-2534 (1997), which is incorporated herein by reference.

Methylation arrays may also be employed to determine the methylation status of a panel of genes of interest. Methylation arrays are disclosed in Beier, V. et al., *Adv Biochem Eng Biotechnol* 104:1-11 (2007), which is incorporated herein by reference in its entirety.

E. Assaying Polypeptide Levels

Levels of EMX2 gene expression can also be detected by measuring levels of EMX2 protein using an antibody that binds specifically to an EMX2 polypeptide. Such antibodies can be detectably labeled to facilitate detection of polypeptide-antibody complex formation using methods well known to those of skilled in the art.

Methods of measuring a level of a polypeptide gene product are known in the art and include antibody-based methods such as enzyme-linked immunoabsorbent assay (ELISA); radioimmunoassay (RIA); protein blot analysis; immunohistochemical analysis; and the like. Such methods also include proteomics methods, such as mass spectral methods, which are known in the art.

An exemplary immunoassay for use in the invention methods for detecting EMX2 protein levels is an immuno-polymerase chain reaction immuno-PCR assay (described in U.S. Pat. No. 5,665,539, which is incorporated herein by reference in its entirety). Immuno-PCR utilizes an antibody (or other agent which binds EMX2 to detect the EMX2 protein, wherein the antibody (or other agent) is linked to a molecule (typically biotin) which specifically binds a bridging molecule (typically avidin), wherein this bridging molecule is capable of binding a second molecule (typically biotin) attached to a nucleic acid marker. This nucleic acid marker is then amplified using PCR methods. This sensitive detection method is particularly useful when EMX2 levels are often difficult to detect by other methods, for example, detection of EMX2 in serum.

Measurement of the polypeptide encoded by an EMX2 gene may further be carried out to specifically measure: (a) the level of EMX2 produced in the entire cell, (b) the level of EMX2 produced in the cytosol, (c) the level of EMX2 produced in the nucleus, (d) level of EMX2 resent in cell-free extract (e.g., serum), and (e) any combination thereof. Exemplary methods which can be used in such measurements include in situ methods such as histochemical staining, particularly differential staining between the cytosol and the nucleus, and in vitro methods such as Western blot analysis of nuclear extracts, cytosolic extracts, or serum.

Those of skill in the art will recognize that it is also possible to measure levels of EMX2 proteins in body fluid, such as serum. Tumors are known to readily shed cells which, after release into the bloodstream, may burst due to cell fragility. Thus, detection of any EMX2 levels, present in body fluid (e.g., serum) is contemplated for use in the invention methods to determine a prognosis of disease-free or overall survival in a manner analogous to that demonstrated with the tissue samples. Very small quantities of EMX2 can be measured in body fluid, for example, using anti-EMX2 antibodies in immuno-PCR methods as described herein.

Accordingly, it is contemplated herein that the reference levels may represent the level of EMX2 resent in a body fluid sample, such as serum. Invention methods that measure the level of circulating EMX2 (i.e., the level of EMX2 in blood or serum), will have a particularly preferred application to early diagnosis and screening, and early determination of risk of cancer recurrence or spread, for patients with abnormal levels of EMX2 in their serum.

F. Normalization Methods

In carrying out a subject method, a level of a gene product in a sample from a patient is assayed. The level of the gene product is then "normalized," generating a normalized expression level of the gene product. The gene product is one that has been identified as predictive of patient prognosis and/or long term survival.

Quantitative RT-PCR is usually performed using an internal standard, or one or more reference genes. The ideal internal standard is expressed at a constant level among different tissues, and is unaffected by the experimental treatment.

Suitable reference genes include, but are not limited to, glyceraldehyde-3-phosphate dehydrogenase (GAPDH) (see, e.g., GenBank Accession No. NM_002046. See, e.g., Eisenberg and Levanon (2003) *Trends in Genetics* 19:362, for a list of additional suitable reference genes. Other possible reference genes are 18S rRNA, actin, TATA-box binding protein (TBP). Actin and GAPDH are both good references for EMX2 methylation analysis.

Calculating a Normalized Value for Gene Products

Normalization for methylation status is similar to TAQMAN RT-PCR, expect that bisulfite-treated genomic DNA is used in TAQMAN PCR as template. Normally we do not calculate normalized values for polypeptides in assays such as Western blots.

The level of an RNA transcript as measured by TAQMAN RT-PCR refers to the cycle threshold (Ct) value. The lower the Ct, the greater the amount of mRNA present in the sample. The expression value of a RNA transcript in a sample is normalized, e.g., by first determining the mean expression value in Ct of designated reference genes in a sample ($Ct_{Ref}$). The normalized expression value for a gene ($Ct_{Gene}$) is then calculated as $Ct_{Gene}$-Ct $Ct_{Ref}$. Optionally, the normalized expression values for all genes can be adjusted, e.g., so that all adjusted normalized Ct have a value >0.

III. Methods Involving Assessment of EMX2 Expression Levels

The data obtained from assessing EMX2 expression status can be applied to a variety of uses, including facilitating an assessment of likelihood of survival, guidance in selection of treatment options, classification of subjects for purpose of clinical trial design, and the like.

Subjects suitable for analysis of EMX2 expression are usually humans, but can also include other mammals such as non-human primates, and non-primate mammals (including veterinary and livestock subjects).

In general, subjects suitable for EMX2 expression analysis include subjects having or suspected of having an EMX2-expressing tumor. Such subjects thus can include those diagnosed as having or suspected of having, a neoplastic disease or tumor such as lung cancer (e.g., non-small cell lung carcinoma, bronchioloalveolar carcinoma, mesothelioma, and the like) colon cancer, skin cancer (e.g., melanoma), or esophageal cancer. In some embodiments, the cancer is other than an endometrial cancer or a testicular cancer. Subjects may have solid or cystic tumors, or diffuse disease. Subjects may have a primary occurrence of cancer as well as localized and metastasized cancer at various stages.

The patient can have or be suspected of having any stage of a cancer. As used herein, the term "stage", when applied to tumor development, refers to the degree of progression of a tumor. Various stages of tumor development are well known to those of skill in the art, as exemplified in Markman 1997, Basic Cancer Medicine. Stages of different cancers are defined according to different criteria, typically using the Tumor-Node-Metastasis (TNM) system. For example, stage I of lung cancer requires no detectable lymph node involvement, and stage II of lung cancer involves either no detectable lymph node involvement and a large primary tumor, or initial lymph node involvement and a small primary tumor. Similar descriptions of the various clinical stages can be found in Markman, supra, for breast cancer, and prostate cancer, colon cancer and ovarian cancer. Early stages of tumor development shall be understood to refer to stages in tumor development in which the tumor has detectably spread no further than the lymph nodes local to the organ of the primary tumor. Typically, early stages will be considered to be stages I and II. As used herein, the phrase, "prior to lymph node involvement" refers to the detectable presence of cancer cells in the organ of the primary tumor, but the lack of a detectable presence of cancer cells in any lymph nodes, including the lymph nodes closest to the organ of the primary tumor.

Facilitating Prognosis—Likelihood of Survival

Because EMX2 expression levels are positively correlated with an increased likelihood of survival, and with an increased likelihood of disease-free survival, EMX2 expression levels in tumor cells of a patient can be used to facilitate a determination of prognosis. For example, cut-off values will be determined based on normalized EMX2 expression levels in a specific population as described above in this application. Then these cut-off values can be used to predict prognostic risk for patients with certain EMX2 values normalized in the same way as used for determining those cut-offs. This information can be used to guide the clinician to acquire further treatment options during follow-up of patients after surgery.

IV. Treatment Options

EMX2 expression levels can be used to guide selection of therapy for a subject. For example, if a patient is classified as having low EMX2 gene expression levels and thus a poor likelihood of survival, a more aggressive treatment regimen and/or more frequent monitoring of disease progression could be recommended. If a patient is classified as having high EMX2 gene expression levels, and thus a strong likelihood of survival, then this can inform therapy selection as well, and may suggest that less radical therapy may be required.

Exemplary cancer treatments include, e.g., radiation therapy, surgical removal of a tumor, laser ablation therapy, and chemotherapeutic regimens. For example, suitable treatments for a colorectal cancer patient include, e.g., chemotherapy with 5-fluorouracil alone or in combination with a platinum based chemotherapeutic compound such as oxaliplatin. As another example, suitable alternative treatments for a head and neck cancer patient include, e.g., a platinum-based chemotherapeutic agent (e.g., cisplatin (cis-DDP), carboplatin, etc.); leucovorin; fluorouracil (5-FU); or combinations such as cisplatin+5-FU; and a taxane (e.g., paclitaxel). As another example, suitable alternative treatments for a non-small cell lung cancer patient include, e.g., a platinum-based chemotherapeutic agent (e.g., cisplatin (cis-DDP), carboplatin, etc.); or leucovorin; and a platinum-based chemotherapeutic agent in combination with a second agent such as gemcitabine, paclitaxel, docetaxel, etoposide or vinorelbine.

Because of the chemo-synergic effect between EMX2 expression and chemotherapeutic agents such as cisplatin (see Example 6, infra), EMX2 expression levels can also guide selection of chemotherapeutic regimen.

In addition, it may be desirable to increase expression of EMX2 in cancer cells, particular where the cancer cells are relatively low EMX2-expressing cells. Such can be accomplished by, for example, delivery of an EMX2 expression construct into cells suspected of being cancerous so as to provide for increased EMX2 expression in the cell. Expression systems are available in the art, and include viral-based systems, "naked" nucleic acid delivery systems, and cationic lipid-based delivery systems.

For example, viral based systems for the delivery of nucleic acid inhibitors can include retroviral, lentivirus, adenoviral, adeno-associated and herpes simplex virus vectors for gene transfer. In many gene therapy applications, it is desirable that the gene therapy vector be delivered with a high degree of specificity to a particular tissue type, e.g., a lung cancer. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *PNAS* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other viruses.

Gene therapy vectors can be delivered in vivo by administration to an individual patient, typically by systemic administration (e.g., intravenous, intraperitoneal, intramuscular, sub-dermal, or intracranial infusion) or topical application.

It may also be of interest to assess EMX2 levels for purposes of clinical trial design and/or analysis of clinical trial results. For example, EMX2 expression levels can be used as a basis for inclusion exclusion from a clinical trial (e.g., it may be desirable to exclude low EMX2 expressers from a clinical study group).

V. Analysis Results Reporting

As discussed above, the likelihood that a patient will exhibit a certain prognosis is assessed by determining a normalized expression level of the EMX2 gene. In some embodiments, a patient's likelihood of survival is provided in a report. Thus, in some embodiments, a subject method further includes a step of preparing or generating a report that includes information regarding the patient's likelihood of survival. For example, a subject method can further include a step of generating or outputting a report providing the results of a survival likelihood assessment, which report can be provided in the form of an electronic medium (e.g., an electronic display on a computer monitor), or in the form of a tangible medium (e.g., a report printed on paper or other tangible medium).

A report that includes information regarding the likelihood that a patient will survive is provided to a user. An assessment as to the likelihood that a patient will survive is referred to below as a "survival likelihood assessment" or, simply, "likelihood assessment." A person or entity who prepares a report ("report generator") will also perform the likelihood assessment. The report generator may also perform one or more of sample gathering, sample processing, and data generation, e.g., the report generator may also perform one or more of: a) sample gathering; b) sample processing; c) measuring a level of EMX2 expression; d) measuring a level of a reference gene product(s); and e) determining a normalized level of EMX2 gene product(s). Alternatively, an entity other than the report generator can perform one or more sample gathering, sample processing, and data generation.

For clarity, it should be noted that the term "user," which is used interchangeable with "client," is meant to refer to a person or entity to whom a report is transmitted, and may be the same person or entity who does one or more of the following: a) collects a sample; b) processes a sample; c) provides a sample or a processed sample; and d) generates data (e.g., level of EMX2 gene product(s); level of a reference gene product(s); normalized level of EMX2 gene product(s)) for use in the likelihood assessment. In some cases, the person(s) or entity(ies) who provides sample collection and/or sample processing and/or data generation, and the person who receives the results and/or report may be different persons, but are both referred to as "users" or "clients" herein to avoid confusion. In certain embodiments, e.g., where the methods are completely executed on a single computer, the user or client provides for data input and review of data output. A "user" can be a health professional (e.g., a clinician, a laboratory technician, a physician (e.g., an oncologist), etc.).

In embodiments where the user only executes a portion of the method, the individual who, after computerized data processing according to the methods of the invention, reviews data output (e.g., results prior to release to provide a complete report, a complete, or reviews an "incomplete" report and provides for manual intervention and completion of an interpretive report) is referred to herein as a "reviewer." The reviewer may be located at a location remote to the user (e.g., at a service provided separate from a healthcare facility where a user may be located).

A. Report

A "report," as described herein, is an electronic or tangible document which includes report elements that provide information of interest relating to a subject likelihood assessment and its results. A subject report includes at least a likelihood assessment, e.g., an indication as to the likelihood that a patient cancer will survive. A subject report can be completely or partially electronically generated. A subject report can further include one or more of: 1) information regarding the testing facility; 2) service provider information; 3) patient data; 4) sample data; 5) an interpretive report, which can include various information including: a) indication; b) test data, where test data can include normalized levels of EMX2 gene products; and/or 6) other features.

Where government regulations or other restrictions apply (e.g., requirements by health, malpractice, or liability insurance), all results, whether generated wholly or partially electronically, are subjected to a quality control routine prior to release to the user.

1. Testing Facility Information

The report can include information about the testing facility, which information is relevant to the hospital, clinic, or laboratory in which sample gathering and/or data generation was conducted. Sample gathering can include obtaining a cancer cell sample from a biopsy, a surgically removed tumor, surgically removed tissue comprising a tumor, or other tissue or bodily fluid from a patient. Data generation can include one or more of: a) measuring a level of a gene product(s); and b) determination of a normalized level of an EMX2 gene product. This information can include one or more details relating to, for example, the name and location of the testing facility, the identity of the lab technician who conducted the assay and/or who entered the input data, the date and time the assay was conducted and/or analyzed, the location where the sample and/or result data is stored, the lot number of the reagents (e.g., kit, etc.) used in the assay, and the like. Report fields with this information can generally be populated using information provided by the user.

2. Service Provider Information

The report can include information about the service provider, which may be located outside the healthcare facility at which the user is located, or within the healthcare facility. Examples of such information can include the name and location of the service provider, the name of the reviewer, and where necessary or desired the name of the individual who conducted sample gathering and/or data generation. Report fields with this information can generally be populated using data entered by the user, which can be selected from among pre-scripted selections (e.g., using a drop-down menu). Other service provider information in the report can include contact information for technical information about the result and/or about the interpretive report.

3. Patient Data

The patient data can include patient medical history (which can include, e.g., data about prior treatment for cancer), personal history; administrative patient data (that is, data that are not essential to the likelihood assessment), such as information to identify the patient (e.g., name, patient date of birth (DOB), gender, mailing and/or residence address, medical record number (MRN), room and/or bed number in a healthcare facility), insurance information, and the like), the name of the patient's physician or other health professional who ordered the assessment and, if different from the ordering physician, the name of a staff physician who is responsible for the patient's care (e.g., primary care physician). Report fields with this information can generally be populated using data entered by the user.

4. Sample Data

The sample data can provide information about the biological sample analyzed in the likelihood assessment, such as the source of biological sample obtained from the patient (e.g., tumor biopsy, surgically removed tumor, unknown, etc.) and the date and time collected. Report fields with this information can generally be populated using data entered by the user, some of which may be provided as pre-scripted selections (e.g., using a drop-down menu).

5. Interpretive Report

The interpretive report portion of the report includes information generated after processing of the data as described herein. The interpretive report can include an indication of patient prognosis. The interpretive report can include, for example, Indication (e.g., type of cancer, etc.); Result of normalized level of EMX2 e.g., "normalized level of EMX2 gene product(s)"); Interpretation; and, optionally, Recommendation(s) (e.g., options for therapy).

It will be readily appreciated that the report can include all or some of the elements above, with the proviso that the report generally includes at least the elements sufficient to provide the analysis requested by the user (e.g., likelihood assessment).

6. Additional Features

It will also be readily appreciated that the reports can include additional elements or modified elements. For example, where electronic, the report can contain hyperlinks which point to internal or external databases which provide more detailed information about selected elements of the report. For example, the patient data element of the report can include a hyperlink to an electronic patient record, or a site for accessing such a patient record, which patient record is maintained in a confidential database. This latter embodiment may be of interest in an in-hospital system or in-clinic setting.

B. Computer-Based Systems and Methods

The methods and systems described herein can be implemented in numerous ways. In one embodiment of particular interest, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site associated (e.g., at a service provider's facility).

For example, during or after data input by the user, portions of the data processing can be performed in the user-side computing environment. For example, the user-side computing environment can be programmed to provide for defined test codes to denote a likelihood "score," where the score is transmitted as processed or partially processed responses to the reviewer's computing environment in the form of test code for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s).

The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which can include test data (e.g., level of an EMX2 gene product; level of a reference gene product(s); normalized level of an EMX2 gene product); and may also include other data such as patient data. This information received can be stored at least temporarily in a database, and data analyzed to generate a report as described above.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the final report) are maintained on a web server for access, preferably confidential access, with typical browsers. The data may be accessed or sent to health professionals as desired. The input and output data, including all or a portion of the final report, can be used to populate a patient's medical record which may exist in a confidential database at the healthcare facility.

A system for use in the methods described herein generally includes at least one computer processor (e.g., where the method is carried out in its entirety at a single site) or at least two networked computer processors (e.g., where data is to be input by a user (also referred to herein as a "client") and transmitted to a remote site to a second computer processor for analysis, where the first and second computer processors are connected by a network, e.g., via an intranet or internet). The system can also include a user component(s) for input; and a reviewer component(s) for review of data, generated reports, and manual intervention. Additional components of the system can include a server component(s); and a database(s) for storing data (e.g., as in a database of report elements, e.g., interpretive report elements, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one example, the architecture is provided as a database-centric client/server architecture, in which the client application generally requests services from the application server which makes requests to the database (or the database server) to populate the report with the various report elements as required, particularly the interpretive report elements, especially the interpretation text and alerts. The server(s) (e.g., either as part of the application server machine or a separate RDB/relational database machine) responds to the client's requests.

The input client components can be complete, stand-alone personal computers offering a full range of power and features to run applications. The client component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the client and server(s), including processing on a single machine such as a mainframe, a collection of machines, or other suitable configuration are contemplated. In general, the client and server machines work together to accomplish the processing of the present invention.

Where used, the database(s) is usually connected to the database server component and can be any device which will hold data. For example, the database can be a any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

C. Computer-Readable Storage Media

The invention also contemplates a computer-readable storage medium (e.g. CD-ROM, memory key, flash memory card, diskette, etc.) having stored thereon a program which, when executed in a computing environment, provides for implementation of algorithms to carry out all or a portion of the results of an assessment as described herein. Where the computer-readable medium contains a complete program for carrying out the methods described herein, the program includes program instructions for collecting, analyzing and generating output, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data is carried out at the remote site to generate a report. After review of the report, and completion of any needed manual intervention, to provide a complete report, the complete report is then transmitted back to the user as an electronic document or printed document (e.g., fax or mailed paper report). The storage medium containing a program according to the invention can be packaged with instructions (e.g., for program installation, use, etc.) recorded on a suitable substrate or a web address where such instructions may be obtained. The computer-readable storage medium can also be provided in combination with one or more reagents for carrying out prognosis assessment (e.g., primers, probes, arrays, or other such kit components).

V. Array and other Compositions for Use in Prediction Methods

The present invention provides arrays for use in carrying out a subject method of assessing prognosis of patient based on EMX2 expression levels.

Arrays including EMX2 on a Chip

The present invention provides an array for use in a subject method. A subject array includes a plurality of polynucleotides immobilized on the surface of an insoluble support. The immobilized polynucleotides comprise nucleotide sequences that are capable of hybridizing with a reference gene or EMX2, whose sequence is known in the art. As such, generation of probes that hybridize under suitable hybridization conditions (e.g., stringent hybridization conditions) is well within the skill level of those of ordinary skill in the art.

As an example, a subject array can comprise a probe that provides for detection of one or more gene product(s) encoded by the EMX2 gene.

The EMX2 gene may be represented in the array by probes immobilized on an insoluble support. It may represent at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, or at least about 95% of the genes represented on the array.

A probe can be "addressable," e.g., the nucleotide sequence, or perhaps other physical or chemical characteristics, of a probe can be determined from its address, i.e. a one-to-one correspondence between the sequence or other property of the probe and a spatial location on, or characteristic of, the solid phase support to which it is attached. For example, an address of a probe can be a spatial location, e.g. the planar coordinates of a particular region containing copies of the probe.

A subject array includes a solid phase support, which may be planar or a collection of microparticles, that carries or carry probes as described above fixed or immobilized, e.g., covalently, at specific addressable locations. For example, a subject array includes a solid phase support having a planar surface, which carries a plurality of nucleic acids, each member of the plurality comprising identical copies of an oligonucleotide or polynucleotide probe immobilized to a fixed region, which does not overlap with those of other members of the plurality. Typically, the nucleic acid probes are single stranded and are covalently attached to the solid phase support at known, determinable, or addressable, locations. The density of non-overlapping regions containing nucleic acids in a microarray is typically greater than 100 per cm$^2$, e.g., greater than 1000 per cm$^2$.

The substrates of the subject arrays may be fabricated from a variety of materials. The materials from which a substrate is fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, is of particular interest in this embodiment. For rigid substrates, specific materials of interest include: glass; plastics, e.g. polytetrafluoroethylene, polypropylene, polystyrene, polycarbonate, and blends thereof, and the like; metals, e.g. gold, platinum, and the like; etc. Also of interest are composite materials, such as glass or plastic coated with a membrane, e.g. nylon or nitrocellulose, etc.

Hybridization between a probe and a test nucleic acid (where a test nucleic acid includes a nucleic acid sample obtained from a cancer cell from a patient) results in a "readout," where "readout" refers to a parameter, or parameters, which are measured and/or detected that can be converted to a number or value. In some contexts, readout may refer to an actual numerical representation of such collected or recorded data. For example, a readout of fluorescent intensity signals from an array is the address and fluorescence intensity of a signal being generated at each hybridization site of the array; thus, such a readout may be registered or stored in various ways, for example, as an image of the array, as a table of numbers, or the like.

The total number of spots on the substrate will vary depending on the number of different oligonucleotide probe spots (oligonucleotide probe compositions) one wishes to display on the surface, as well as the number of non probe spots, e.g., control spots, orientation spots, calibrating spots and the like, as may be desired depending on the particular application in which the subject arrays are to be employed. The pattern present on the surface of the array can include at least 2 distinct nucleic acid probe spots, at least about 5 distinct nucleic acid probe spots, at least about 10 distinct nucleic acid spots, at least about 20 nucleic acid spots, or at least about 50 nucleic acid spots.

In some cases, it may be desirable to have each distinct probe spot or probe composition be presented in duplicate, i.e. so that there are two duplicate probe spots displayed on the array for a given target. In some cases, each target represented on the array surface is only represented by a single type of oligonucleotide probe. In other words, all of the oligonucleotide probes on the array for a give target represented thereon have the same sequence. In certain embodiments, the number of spots will range from about 200 to 1200. The number of probe spots present in the array can make up a substantial proportion of the total number of nucleic acid spots on the array, where in many embodiments the number of probe spots is at least about 25%, at least 50%, at least about 80%, or at least about 90% of the total number of nucleic acid spots on the array.

A subject array can be prepared using any convenient means. One means of preparing an array is to first synthesize the oligonucleotides for each spot and then deposit the oligonucleotides as a spot on the support surface. The oligonucleotides may be prepared using any convenient methodology, where chemical synthesis procedures using phosphoramidite or analogous protocols in which individual bases are added sequentially without the use of a polymerase, e.g. such as is found in automated solid phase synthesis protocols, where such techniques are well known to those of skill in the art.

Following preparation of the target nucleic acid from the tissue or cell of interest, the target nucleic acid is then contacted with the array under hybridization conditions, where such conditions can be adjusted, as desired, to provide for an optimum level of specificity in view of the particular assay being performed. Suitable hybridization conditions are well known to those of skill in the art and reviewed in Maniatis et al., supra, and WO 95/21944. Of particular interest in many embodiments is the use of stringent conditions during hybridization, i.e. conditions that are optimal in terms of rate, yield and stability for specific probe-target hybridization and provide for a minimum of non-specific probe/target interaction. Stringent conditions are known to those of skill in the art.

Following hybridization, non-hybridized labeled nucleic acid is removed from the support surface, conveniently by washing, generating a pattern of hybridized nucleic acid on the substrate surface. A variety of wash solutions are known to those of skill in the art and may be used. Methods of detecting hybridization between a probe nucleic acid and a target nucleic acid include scintillation counting, autoradiography, fluorescence measurement, colorimetric measurement, light emission measurement, light scattering, and the like.

VII. Kits

In another embodiment of the invention, a kit is provided to determine the levels of EMX2 expression in the cancerous tumor cells of a patient. Such a kit will comprise a reagent for detecting either the DNA encoding EMX2, the mRNA encoding EMX2 the EMX2 polypeptide, or any combination thereof. The reagent will comprise one or more molecules capable of specifically binding a nucleic acid sequence (DNA or RNA) encoding an EMX2 polypeptide.

The kit may comprise one or more nucleic acid reagents for the detection of either DNA encoding EMX2, mRNA encoding EMX2 or both. The one or more nucleic acid reagents may be used for hybridization or amplification with the DNA and/or mRNA encoding EMX2. The kit may comprise one or more pairs of primers for amplifying the DNA and/or mRNA encoding EMX2. The kit may further comprise samples of total mRNA derived from tissue of various physiological states, such as normal and metastatically progressive tumors, for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting the DNA and/or mRNA encoding EMX2 in cancer cells in a biological sample comprising oligonucleotide probes effective to bind with high affinity to DNA and/or mRNA encoding EMX2 in vitro or in situ and containers for each of these probes.

In a further embodiment, the invention encompasses a kit for use in determining the level of EMX2 expression in a biological sample comprising one or more agents, such as, for example, one or more antibodies, specific for one or more EMX2 polypeptides. In one particular embodiment, the kit will comprise one or more agents and one or more nucleic acid markers wherein the agents and nucleic acid markers are modified in a fashion appropriate for carrying out immuno-polymerase chain reaction assays.

Probes and primers for inclusion in a subject kit include those useful in various amplification and/or detection systems. Exemplary amplification and/or detection systems include SUNRISE primer-based systems, Molecular Beacons, the TAQMAN system, an AMPLIFLUOR hairpin primer-based system, a Scorpions technology (e.g., bi-functional molecules containing a PCR primer element covalently linked to a probe element), and a Light Upon Extension or LUXT™-based system. Further exemplary detection systems include those based on a melt-curve analysis, and using intercalating dyes such as the fluorescent dye SYBR Green.

The kits may optionally comprise reagent(s) with an identifying description or label or instructions relating to their use in the methods of the present invention. The kits may comprise containers (including microtiter plates suitable for use in an automated implementation of the method), each with one or more of the various reagents (typically in concentrated form) utilized in the methods of the invention, including, for example, pre-fabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more probes and primers of the present invention (e.g., appropriate length poly (T) or random primers linked to a promoter reactive with the RNA polymerase). Instructions for the use of mathematical algorithms to assess patient prognosis can also be included in a subject kit.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Real-Time RT-PCR Analysis of EMX2 Expression and Methylation Analysis of the EMX2 Promoter in Human Lung Cancer Cell Lines Expression studies were designed and conducted with the primary goal of molecularly characterizing EMX2 expression in non-small cell lung carcinoma (NSCLC) cells. The following experiments resulted in the observation that silencing of EMX2 by promoter hyper-methylation in human lung cancer cells allows for aberrant activation of Wnt genes, which would otherwise remain un-transcribed due to the presence of the EMX2 repression complex in normal cells.

EMX2 expression in human lung cancer cell lines was determined by using quantitative real-time PCR (RT-PCR), and the relative expression was calculated by normalizing to an internal control, GAPDH. To examine whether downregulation of EMX2 in human lung cancer cell lines is due to methylation of the gene's promoter, a promoter methylation analysis was performed by using quantitative methylation specific PCR (qMSP).

Materials and Methods
Cell Culture

Human cell lines were obtained from the American Type Culture Collections (ATCC) (Manassas, Va.). These cell lines included non-small cell lung cancer (NSCLC) (A549, H1703, H460, H838, H1299, H1650, H1975, H2170, H1666, H522, H322, H441, and A427); mesothelioma (211H, H513, H2052, and H28); colon cancer (SW480, HCT116, HT29, and Lovo); melanoma (LOX, FEM, FEMX, and SK-Mel-2). Other human mesothelioma cancer cell lines H290 and MS-1 were obtained from the NIH (Frederick, Md.). Normal mesothelial cell line LP-9 was obtained from the Cell Culture Core Facility at Harvard University (Boston, Mass.). Human Barrett's-associated adenocarcinoma cell lines TE-7, BIC-1 and SEG-1 were obtained from Dr. Michael Korn (Comprehensive Cancer Center, University of California, San Francisco)—The human Barrett's associated adenocarcinoma cell lines OE19, OE21, and OE33 were obtained from the European Collection of Cell Culture (Salisbury, UK).

Most cell lines are routinely cultured in RPMI 1640 supplemented with 10% fetal bovine serum, penicillin (100 IU/ml) and streptomycin (100 ug/ml), except, LP-9 was cultured in M199 containing 15% CS plus 10 ng/ml of EGF plus 0.4 µg/ml of HC; the normal renal cell line HRE152 was cultured in alphaMEM supplemented with 10% fetal bovine serum, penicillin (100 IU/ml) and streptomycin (100 ug/ml); and normal human small airway epithelial cells (SAEC) and bronchial epithelial cells (NHBE) (primary cultures) will be obtained from Clonetics (Walkersville, Md.) and cultured in Clonetics SAGM™ Bullet Kit. All cell lines were cultured at 37° C. in a humid incubator with 5% $CO_2$.

Semi-quantitative Reverse Transcription Polymerase Chain Reaction (RT-PCR)

Reverse transcription-polymerase chain reaction (RT-PCR) was performed in a GeneAmp PCR system 9700 (Applied Biosystems, Foster City, Calif.), using an RT-PCR kit (SuperScript II one-step RT-PCR with Platinum Taq kit; Invitrogen, Carlsbad, Calif.) according to the manufacturer's protocol. Primers for RT-PCR were obtained from Operon Biotechnologies (Huntsville, Ala.). Total RNA of normal human lung was obtained from the Biochain Institute (Hayward, Calif.). Total RNA (500 ng) was used for each reaction. Primer sequences were as follows: human EMX2 DNA, Forward primer; 5'-GATATCTGGGTCATCGCTTC-3' (SEQ ID NO: 3), Reverse primer; 5'-TGAGTTTCCGTGAGGCT-GAG-3' (SEQ ID NO:4).

Quantitative Real-Time RT-PCR

First-strand cDNA was synthesized from total RNA using iScript cDNA synthesis kit (Bio-Rad, Hercules, Calif.) according to the manufacturer's instructions. Transcript analysis was done by real-time reverse transcription-PCR using the TAQMAN assay. Hybridization probes and primers (Inventoried, chosen from the online catalog) were purchased from Applied Biosystems (Foster City, Calif.). All samples were amplified simultaneously in triplicate and amplifications were run in a 7900 real-time PCR System (Applied Biosystems, Foster City, Calif.). Each value was normalized to its GAPDH level.

Quantitative Methylation-Specific PCR (qMSP)

qMSP methods were modified according to Fackler M. J. et al., "Quantitative multiplex methylation-specific PCR assay for the detection of promoter hypermethylation in multiple genes in breast cancer." Cancer Res 64:4442-52 (2004). Genomic DNA from cell lines and tissue samples was extracted with a DNEASY TISSUE KIT (Qiagen, Valencia, Calif.), according to the manufacturer's instructions. Primers and probes were designed using PRIMER EXPRESS Software and METHYL PRIMER EXPRESS Software v1.0 (Applied Biosystems, Foster City, Calif.) and purchased from Operon (Huntsville, Ala.) and Applied Biosystems respectively. Regular Methylation specific and un-methylation specific PCR was performed to validate the quality of the EMX2 rimers before they were used for qMSP, according to Clement G. et al., "Epigenetic alteration of the Wnt inhibitory factor-1 promoter occurs early in the carcinogenesis of Barrett's esophagus." Cancer Sci 99:46-53 (2008) and Galm et al., "Methylation-Specific Polymerase Chain Reaction." Methods Mol. Med. 113:296-291 (2005).

Bisulfite modification of genomic DNA was performed with a methylation kit (EZ DNA METHYLATION-GOLD KIT; Zymo Research, Orange, Calif.). ATCB primers and a probe designed in areas without CpG nucleotides, thus amplifying the ACTB gene after bisulfite modification and independent from the methylation status of CpG nucleotides, were used as an internal reference gene (Harden S. V. et al., "Gene promoter hypermethylation in tumors and lymph nodes of stage I lung cancer patients." Clin Cancer Res 9:1370-5 (2003)).

qMSP was performed in the same plates for both genes. To determine the relative levels of methylated promoter DNA in each sample, values were compared with the values of the internal reference gene (ACTB) in order to obtain a ratio that was then multiplied by 100 to give a percentage value (gene of interest/reference gene*100). Finally, the ratio of (tumor/normal expression in tissue samples or the H1703 expression as control in cell lines) was calculated. A cut-off ratio of hyper-methylation at 5.0 or more was fixed. The primer sequences are summarized in FIG. 20. Fluorogenic PCR was carried out in a reaction volume of 25 µl, consisting of 500 nM of each primer; 200 nM probe; TAQMAN UNIVERSAL PCR MASTER MIX (2×). Thermal cycling was initiated with a first denaturation step of 95° C. for 10 min, followed by 95° C. for 15 s and 58° C. for 1 min for 60 cycles. Amplifications were carried out in 96-well plates in a 7300 SEQUENCE DETECTOR (Applied Biosystems). All samples were run in triplicate and repeated two times. Each plate included multiple water blanks, as negative controls.

Cell Culture and 5-Aza-2'-deoxycytidine (DAC) Treatment

Human NSCLC cell lines H1299, H322 and A427 were purchased from American Type Culture Collection (ATCC), (Manassas, Va.). These cell lines were cultured in RPMI 1640 supplemented with 10% fetal bovine serum, penicillin (100 IU/mL) and streptomycin (100 µg/mL). All cells were cultured at 37° C. in a humidified incubator with 5% CO2. Total RNA from cell lines was isolated using RNeasy Mini kit (Qiagen). Treatment with 5 µM 5-aza-2'-deoxycytidine (DAC; Sigma) was done according to Clement G. et al., "Epigenetic alteration of the Wnt inhibitory factor-1 promoter occurs early in the carcinogenesis of Barrett's esophagus." Cancer Sci 99:46-53 (2008).

Results and Analysis

Hyper-methylation in the promoter region of EMX2 caused down-regulation of EMX2 expression in non-small cell lung carcinoma (NSCLC) cell lines and suppressed cell proliferation (FIG. 1). The bar graph in panel a) shows EMX2 expression levels in 12 different NSCLC cell lines and normal lung. The relative expression levels were determined by quantitative real-time PCR (RT-PCR). Glyceraldehyde 3-phosphate dehydrogenase (GAPDH), a housekeeping gene that is stably and constitutively expressed at high levels in most tissues and cells, was used as an internal control for normalization calculations. EMX2 expression was lost in almost all lung cancer cell lines examined as compared to the normal pleural control, with the exception of the H1703 and A427 lines.

A high degree of promoter methylation is associated with low EMX2 expression levels, and vice versa (FIG. 1). The bar graph in Panel B shows the extent of EMX2 promoter methylation in the same 12 NSCLC cell lines as a percentage (%) determined by quantitative methylation specific PCR (qMSP). Read in conjunction with one another, Panels A and B illustrate that the extent of EMX2 promoter methylation correlates with the extent of EMX2 gene expression in all lung cancer cell lines examined.

Figure 2:
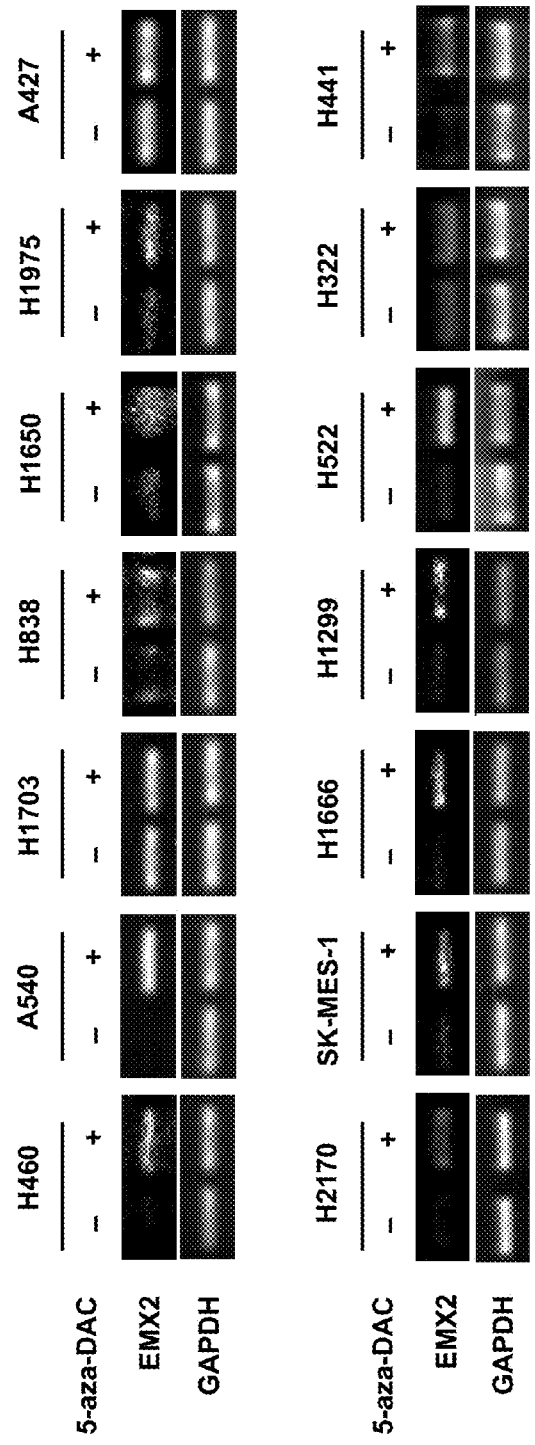
FIG. 2 is a series of ethidium-stained agarose gels demonstrating the semi-quantitative results from RT-PCR analyses. The runs show the results of RT-PCR for EMX2 performed on the above NSCLC cell lines. The cell lines were treated with 5 µM 5-aza-2'-deoxycytidine (DAC) in order to confirm the methylation status of their respective EMX2 promoters. Being a de-methylation treatment, DAC restored EMX2 expression levels in NSCLC cell lines (see, for example, the presence of strong white bands in upper right-hand sections when DAC is added, versus the general absence of white bands when DAC is not added). Accordingly, cell lines with initially silenced EMX2 were observed to re-express EMX2 when their promoters were chemically de-methylated with DAC.

FIG. 2 further illustrates that EMX2 expression is down-regulated by methylation in NSCLC cell lines. NSCLC cell lines were treated with 5 μM 5-aza-2'-deoxycytidine (DAC) in order to confirm the methylation status of their respective EMX2 promoters. Being a de-methylation treatment, DAC restored EMX2 expression levels in NSCLC cell lines (see, for example, the presence of strong white bands in upper right-hand sections when DAC is added, versus the general absence of white bands when DAC is not added). Accordingly, cell lines with initially silenced EMX2 were observed to re-express EMX2 when their promoters were chemically de-methylated with DAC. This result further supports the observation that methylation of the EMX2 promoter region suppresses EMX2 expression in NSCLC cell lines.

Example 2

Real-Time RT-PCR Analysis of EMX2 Expression and Methylation Analysis of the EMX2 Promoter in Human Primary Lung Cancer Tissue Samples A gene expression study was designed and conducted with the primary goal of molecularly characterizing gene expression in tissue samples from human lung cancer patients and correlating this with patient prognosis and clinical outcome.

Assays were performed on lung cancer tumor tissues obtained from 144 individual patients as detailed in the Materials and Methods section.

Materials and Methods
Patient Characteristics

A total of 144 patients with lung adenocarcinoma were studied. All patients underwent surgery at the University of California, San Francisco (UCSF) at some point between July 1999 and August 2006. TNM staging designations were made according to the World Health Organization (WHO) pathologic classification staging system. Pathological lymph node status was evaluated for all the specimens. The 144 patients included 81 adenocarcinoma patients without BAC, and 63 patients with features of BAC. In addition to histopathologic diagnosis, patients' clinical records including follow-up were documented. The median follow-up period for all patients was 42.8±2.1 months extending until May 10, 2007.
Tissue Samples and Extraction of RNA Fresh human lung cancer tissue was collected from patients undergoing resection of their tumors approval by the Committee on Human Research (CHR) at UCSF Shi Y. et al., "Inhibition of Wnt-2 and galectin-3 synergistically destabilizes beta-catenin and induces apoptosis in human colorectal cancer cells." *Int J Cancer* (2007). These tissue samples were snap-frozen in liquid nitrogen immediately after resection and kept at −170° C. prior to use. Total RNA from fresh tumor samples was extracted using the TRIzol LS method (Invitrogen, Carlsbad, Calif.).

Results and Analysis

Figure 3:
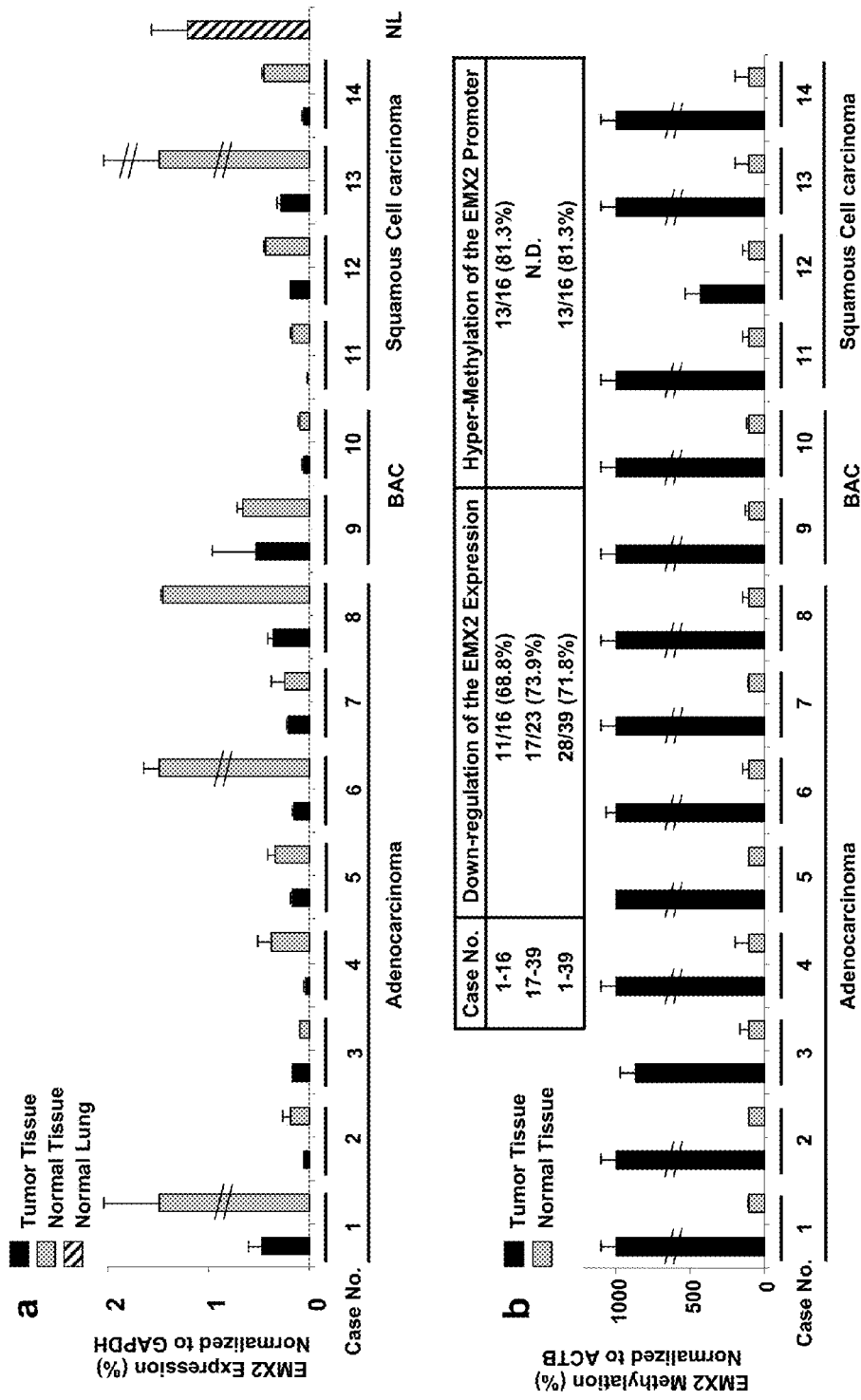
FIG. 3 presents two bar graphs showing a comparison of EMX2 expression levels and degree of promoter methylation in matched tissue samples from normal lung and lung adenocarcinoma. In Panel A 71.8% of the cancer tissue samples (28 out of 39; see inserted table) showed a reduction in EMX2 expression as compared to their matched normal samples. Panel B shows the results of qMSP of the EMX2 promoter in these same tissues. Hyper-methylation was found in 81.3% of the cases (13 out of 16) where EMX2 expression was also absent or diminished. These data indicate that in the selected NSCLC tissue samples, EMX2 down-regulation correlates with hypermethylation of CpG islands in the gene's promoter region.

In NSCLC tissue samples, EMX2 down-regulation correlates with hypermethylation of CpG islands in its promoter. FIG. 3 shows a comparison of matched tissue samples from normal lung and lung adenocarcinoma. In Panel A 71.8% cancer tissue samples (28 out of 39 cases) had less EMX2 expression than their matched normal samples (see inserted table; not all data shown). Panel B shows the results of quantitative Methylation Specific PCR (qMSP) of the EMX2 promoter in these same tissues. Hyper-methylation was found in 81.3% cases (13 out of 16 cases) where EMX2 expression was absent or diminished.

Example 3

Statistical Analysis of EMX2 Expression Levels in NSCLC Tissue Samples According to Clinical Characteristics and Outcome Lung cancer tissue samples were derived from 144 patients, 81 of which had adenocarcinoma without bronchioloalveolar carcinoma (BAC), and 63 of which had adenocarcinoma with features of BAC. These were compared to 65 normal lung tissue samples.

Materials and Methods

RNA extraction, RT-PCR, and qMSP were performed as described in Examples 1-2.

Statistical Analyses

The Kaplan-Meier method was used to estimate overall survival and recurrence-free survival. Differences in survival between the low-risk group (high level of EMX2 expression) and high-risk group (low level of EMX2 expression) were analyzed by a log-rank test. A Multivariate Cox proportional hazards regression analysis was used to assess the effect of EMX2 expression on survival. Hazard ratios (HR) and 95% confidence interval (CI) were calculated from the Cox regression model. The correlation between gene expression and discrete clinical categories were analyzed by the t-test, ANOVA with Bonferrini/Dunn test, Mann-Whitney's U-test for variables with two-categories, and the Kruskal-Wallis test for variables with more than two categories. All reported p-values were two-sided.

To compare the relative EMX2 expression levels among the patients, optimal cut-off points were created for partitioning the patients into high and low risk survival subgroups. The threshold of EMX2 expression levels at each cut-off point was determined by the use of survival trees. Assessment of the predictive reproducibility of the partitions was made based on Therneau, T. M. et al., "An introduction to recursive partitioning using the R-PART routines." *Technical report, Mayo Foundation* (1997).

Results and Analysis

The EMX2 expression status in the above NSCLC patients and corresponding clinical characteristics are set forth in the table presented in FIG. 4. 144 cancer patients with adenocarcinoma and/or bronchioloalveolar carcinoma and 65 normal lung patients gave tissue samples. As above, RT-PCR was used to determine EMX2 gene expression in each sample, and quantitative methylation specific PCR (qMSP) was used to determine the extent of EMX2 promoter methylation in each sample. EMX2 expression was evaluated in healthy and cancerous groups, and significant differences are shown. For example, consistently high EMX2 expression levels were significantly associated with overall survival (Hazard ratio: 0.44, CI: 0.23-0.85, p=0.02 EMX2 was associated with vital status (p=0.003), recurrence (p=0.007), and sex (p=0.04). Females and living patients had significantly higher EMX2 expression levels. In contrast, patients with recurrent cancer had low EMX2 expression levels. There was no significant association between EMX2 expression and tumor stage, age, smoking, histology, operation procedure, and ECOG PS.

In survival analyses in general, the Hazard Ratio (HR) is an estimate of the likelihood of patient survival. FIG. 5 is a table summarizing the HR of groups of patients separated by EMX2 expression levels. HR increases with increasingly severe pathological stage. Here, tissue samples were taken from lung cancer patients and separated into low and high expressing groups. High EMX2 expressing groups demonstrate a low HR, indicating a higher likelihood of survival for individuals in that group. Consistently high EMX2 expression levels are significantly associated with overall survival. Bronchioloalveolar carcinoma is reported to have a lower HR than adenocarcinoma; however, this may be only marginally significant (a p-value of 0.12 versus a p-value of less than 0.05 for statistically significant data).

Figure 6A:
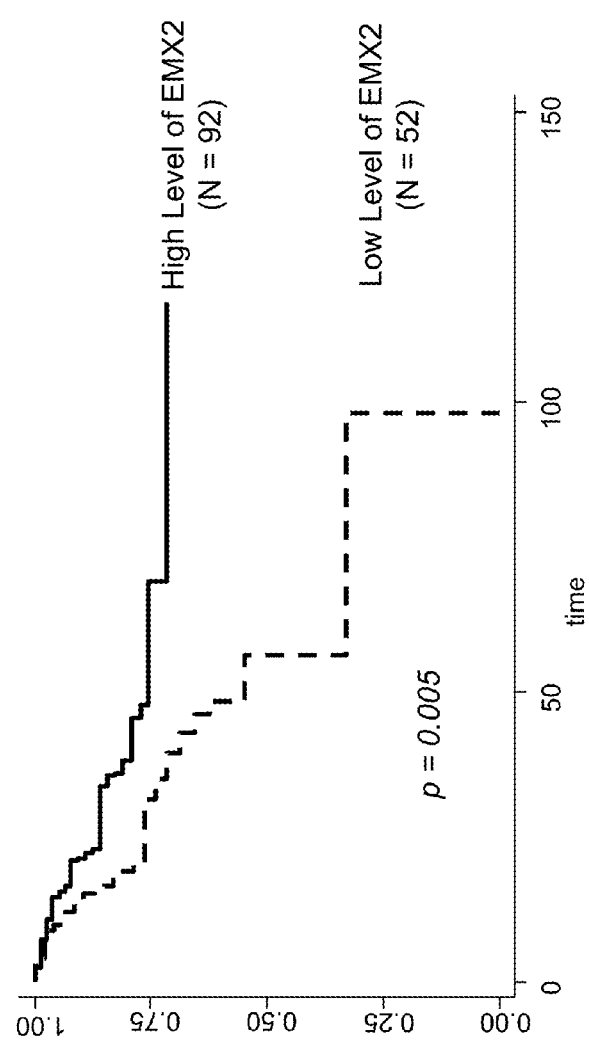
FIGS. 6A-6G show Kaplan-Meier survival curves for both adenocarcinoma and bronchioloalveolar carcinoma patients over a period of 100 to 150 months. Overall survival was significantly better in the EMX2-high expressing group compared to those in the EMX2-low expressing group in all patients (p=0.005; the median survival: high (not reached) vs. low (60 months)) (FIG. 6A), stage I patients using optimal cut-off point 1: 1.29 (p=0.01; not reached vs. 56 months) (FIG. 6B) or optimal cut-off point 2: 6.77 (p=0.006; not reached vs. 98 months) (FIG. 6C), and in adenocarcinoma patients with BAC features (p=0.03; not reached vs. 56 months) (FIG. 6D). On the other hand, no difference in survival was observed in patients with stages II to IV (p=0.36) (FIG. 6E), and in adenocarcinoma patients without BAC features (p=0.13) (FIG. 6F). Furthermore, there was statistical significance in recurrence-free survival for all patients: The median recurrence-free survival in EMX2-low expressing group was 24 months, compared to 52 months for the EMX2-high expressing group (p<0.001) (FIG. 6G).
Figure 6B:
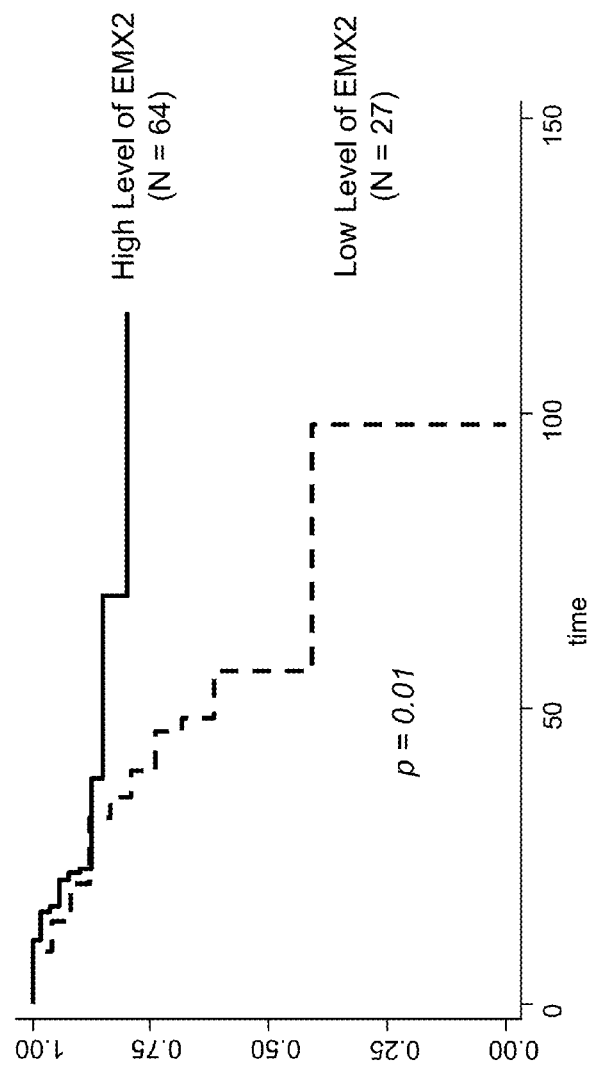
Figure 6C:
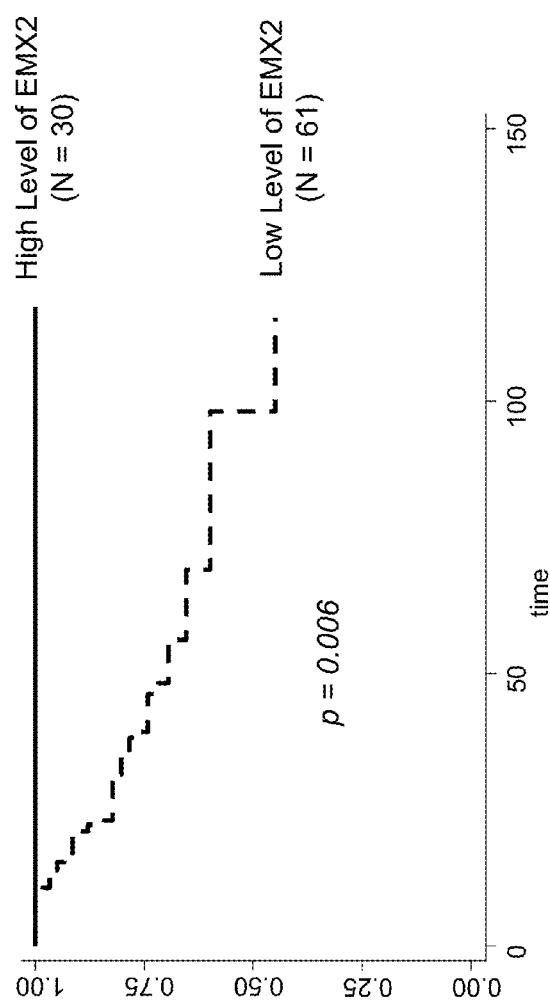
Figure 6D:
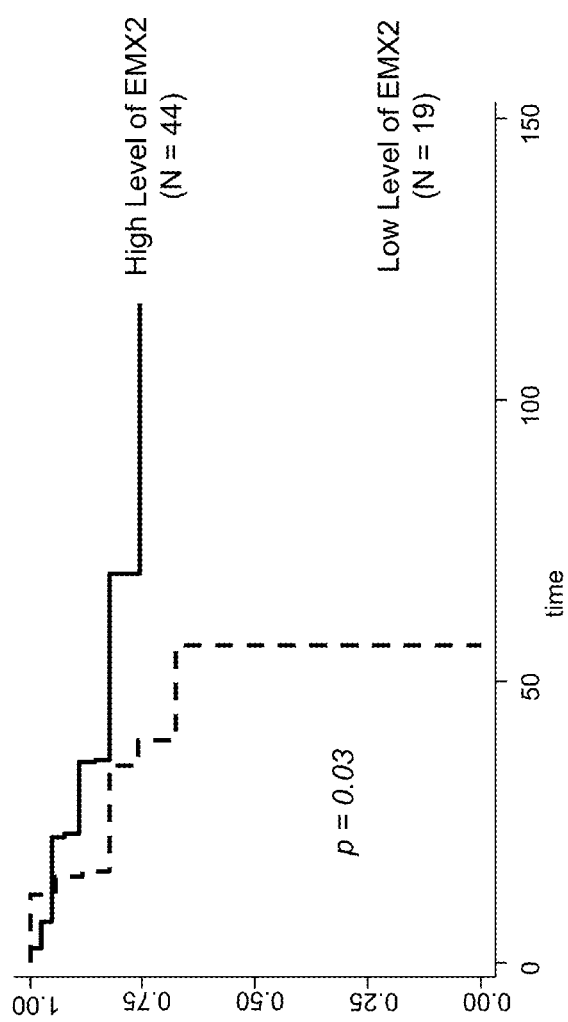
Figure 6E:
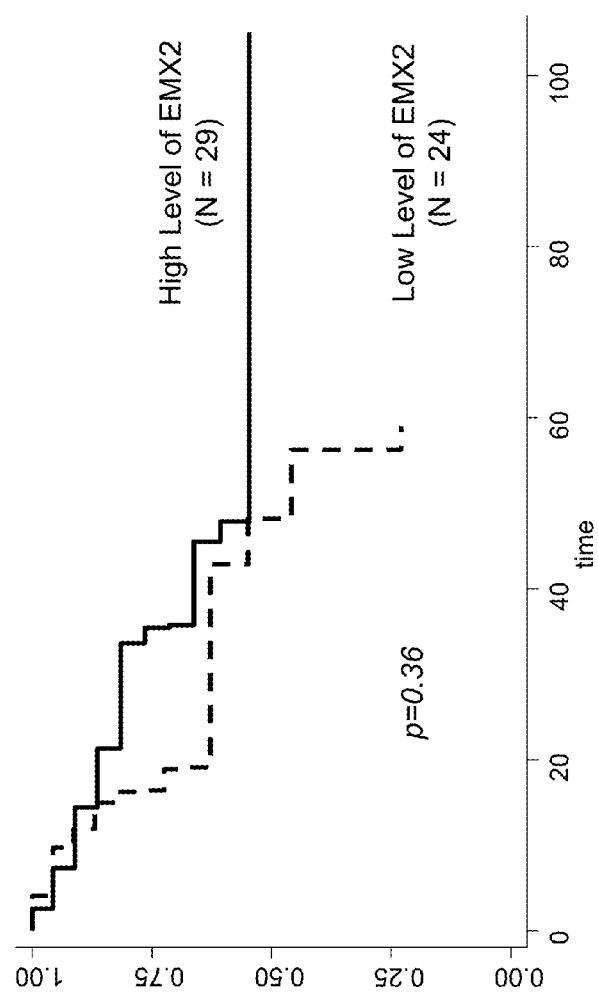
Figure 6F:
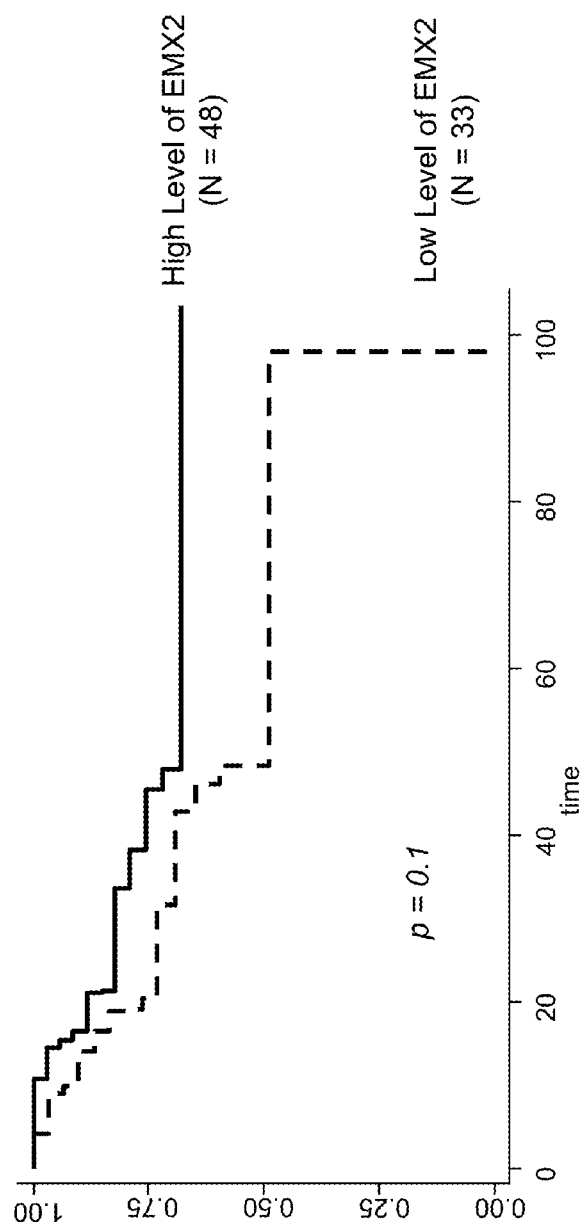
Figure 6G:
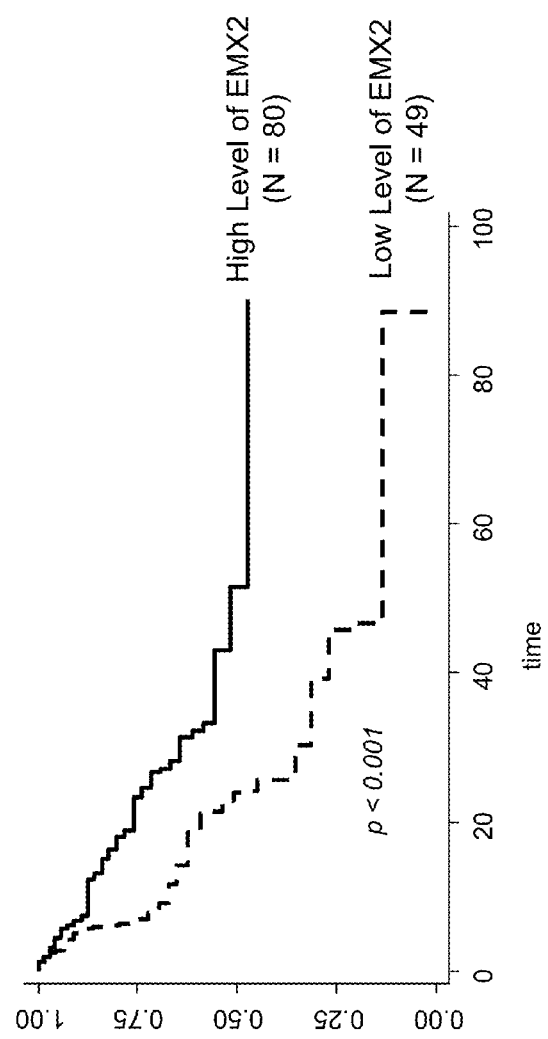

The Figures have been updated with labels, especially the Y-axis. The cut-off determination is described in section [00180] and [00181]. Kaplan-Meier survival estimates for both adenocarcinoma and bronchioloalveolar carcinoma patients over a period of 100 to 150 months using various cut-off points are presented in FIGS. 6A-6G. The graphs illustrate that overall survival was significantly improved in patients in the high EMX2 expressing group compared to those in the low EMX2 expressing group in all patients (p=0.005; the median survival: high (not reached) vs. low (60 months)) (FIG. 6A). Stage I patients using an optimal cut-off point of 1: 1.29 (p=0.01; not reached vs. 56 months) (FIG. 6B). An optimal cut-off point of 2: 6.77 (p=0.006; not reached vs. 98 months) (FIG. 6C). In adenocarcinoma patients with BAC features (p=0.03; not reached vs. 56 months) (FIG. 6D). Conversely, no difference was observed in survival of patients with stage II to IV cancer (p=0.36) (FIG. 6E), and adenocarcinoma patients without BAC features (p=0.13) (FIG. 6F). Furthermore, there was statistical significance in the recurrence-free survival for all patients. The median recurrence-free survival in the low EMX2 expressing group was 24 months, compared to 52 months for the high EMX2 expressing group (p<0.001) (FIG. 6G).

Example 4

Effects of EMX2 Restoration on Canonical Wnt Signaling Pathway in NSCLC Cells

A "knock-in" study was designed to determine whether the expression levels of several oncogenic Wnt genes were down-regulated as a result of EMX2 restoration. EMX2 as transfected (or "knocked-in") to three NSCLC lines. Semi-quantitative RT-PCR was performed on the cell lines to assess expression levels of Wnt pathway members in the presence of EMX2.

Materials and Methods

RNA extraction and RT-PCR were performed as described in Examples 1-2.

EMX2 Transfection into Lung Cancer Cell Lines

The pcDNA 3.1/EMX2 vector was sub-cloned from pCMV6-XL5 EMX2 vector (ORIGENE, Rockville, Md.). pCMV6-XL5 EMX2 and pcDNA3.1 (Invitrogen, Carlsbad, Calif.) were digested by the EcoRI restriction enzyme (BioLabs, Ipswich, Mass.). This insert and vector were purified by MUNIELUTE PCR Purification Kit (QIAGEN, Valencia, Calif.). Last, they were ligated using QUICK LIGATION Kit (BioLabs, Ipswich, Mass.). Human lung cancer cell lines H460, H1299 and H322 were plated in six-well plates with fresh media without antibiotics for 24 hrs before transfection. Cells were then transfected with pcDNA 3.1/EMX2 and with an empty pcDNA3.1 vector, using Lipofectamine 2000 transfection reagent (Invitrogen, Carlsbad, Calif.) according to the manufacturer's protocol. Cells were next detached and plated in 10 cm cell culture dishes with G418 (500 µg/ml; Invitrogen) for selection purposes. Stable transfectants were harvested and maintained with G418 for further analysis.

TOP/FOP FLASH Assay

Cells were plated in 12-well plates with fresh media without antibiotics 24 hrs before transfection. One microgram of the TOPFLASH or FOPFLASH reporter plasmid and 0.05 µg of the internal control plasmid pRL-TK (Promega, Madison, Wis.) were cotransfected transiently into cells as described previously. Transfection was performed by using LIPO-FECTAMIN 2000 (Invitrogen) according to the manufacturer's instructions. The cells were incubated at 37° C. for 24 hr, washed once with PBS, and then lysed to measure luciferase reporter gene expression by using a dual-luciferase reporter assay system (Promega). TCF-dependent transcriptional activity was determined by the ratio of pTOPFLASH/pFOP-FLASH luciferase activity, each normalized to luciferase activities of the pRL-TK reporter. All experiments were performed in triplicate.

Western Blotting

Whole cell lysates were obtained with M-PER protein extraction reagent (PIERCE, Rockford, Ill.). Cytosolic proteins were prepared as previously described. The proteins were separated on 4-15% gradient sodium dodecyl sulfate (SDS)—polyacrylamide gels and transferred to Immobilon-P membranes (Millipore, Billerica, Mass.). The proteins were first bound with the following primary antibodies: Dvl-3 and survivin (NOVUS, Littleton, Colo.), β-catenin (BD Biosciences Transduction Laboratories, Lexington, Ky.), cyclin D1 (Cell Signaling Technology, Danvers, Mass.), and β-actin (Sigma, St. Louis, Mo.). Antigen-antibody complexes were detected with an enhanced chemiluminescence (ECL) blotting analysis system (GE Healthcare Life Sciences, Piscataway, N.J.).

Results and Analysis

Figure 7:
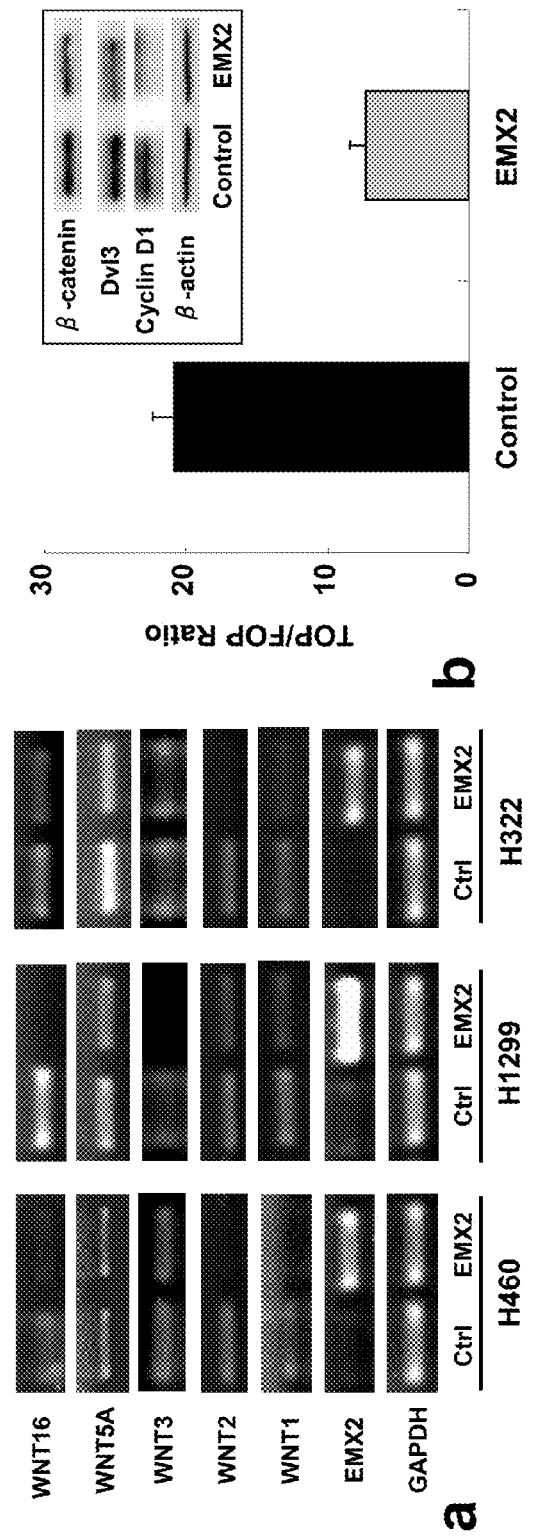
FIG. 7 is a series of ethidium-stained agarose gels demonstrating the semi-quantitative results from RT-PCR analyses, a Western blot showing protein levels of downstream effectors of Wnt in response to EMX2 restoration, and a summary bar graph. The RT-PCR results show the expression levels of several oncogenic Wnt genes. The expression of Wnt1, Wnt2, Wnt3, Wnt5A, and Wnt16 was down-regulated by EMX2 restoration in EMX2-transfected NSCLC cell lines (Panel A). Panel B is a Western blot result showing dramatic down-regulation of the Wnt pathway effectors such as cytosolic β-catenin, and Dvl3 level as well as one direct canonical Wnt downstream target gene, Cyclin D1, in EMX2-transfected NSCLC cell lines. As can be seen, levels of the proteins encoded by these genes decreased when EMX2 was exogenously introduced into the NSCLC lines.

The expression levels of several oncogenic Wnt genes, such as Wnt1, Wnt2, Wnt3, Wnt5A, and Wnt16 were down-regulated by EMX2 restoration (FIG. 7); Panel A shows the general absence of white bands in the right-hand sections when EMX2 s present. To further confirm the results observed in RT-PCR analysis, Western blot analysis was performed to examine the expression levels of several Wnt pathway effectors and downstream target genes in the present of EMX2 β-actin served as a loading control. Key indicators of canonical Wnt pathway activation include increased expression levels downstream targets of Wnt, including cytosolic β-catenin, Dvl3 and Cyclin D1. Each of these was dramatically down-regulated in the presence of EMX2 Panel B; table insert). EMX2 also inhibited expression of canonical Wnt signaling pathway members as measured by the TOP/FOP reporter assay (Panel B; bar graph).

Example 5

Restoration of EMX2 Suppresses the Proliferation of NSCLC Cells

The ability of EMX2 to suppress growth of NSCLC cells through inhibition of the Wnt signaling pathway was examined. EMX2 expression was introduced in NSCLC cell lines in order to determine whether proliferation increased or decreased.

Figure 8:
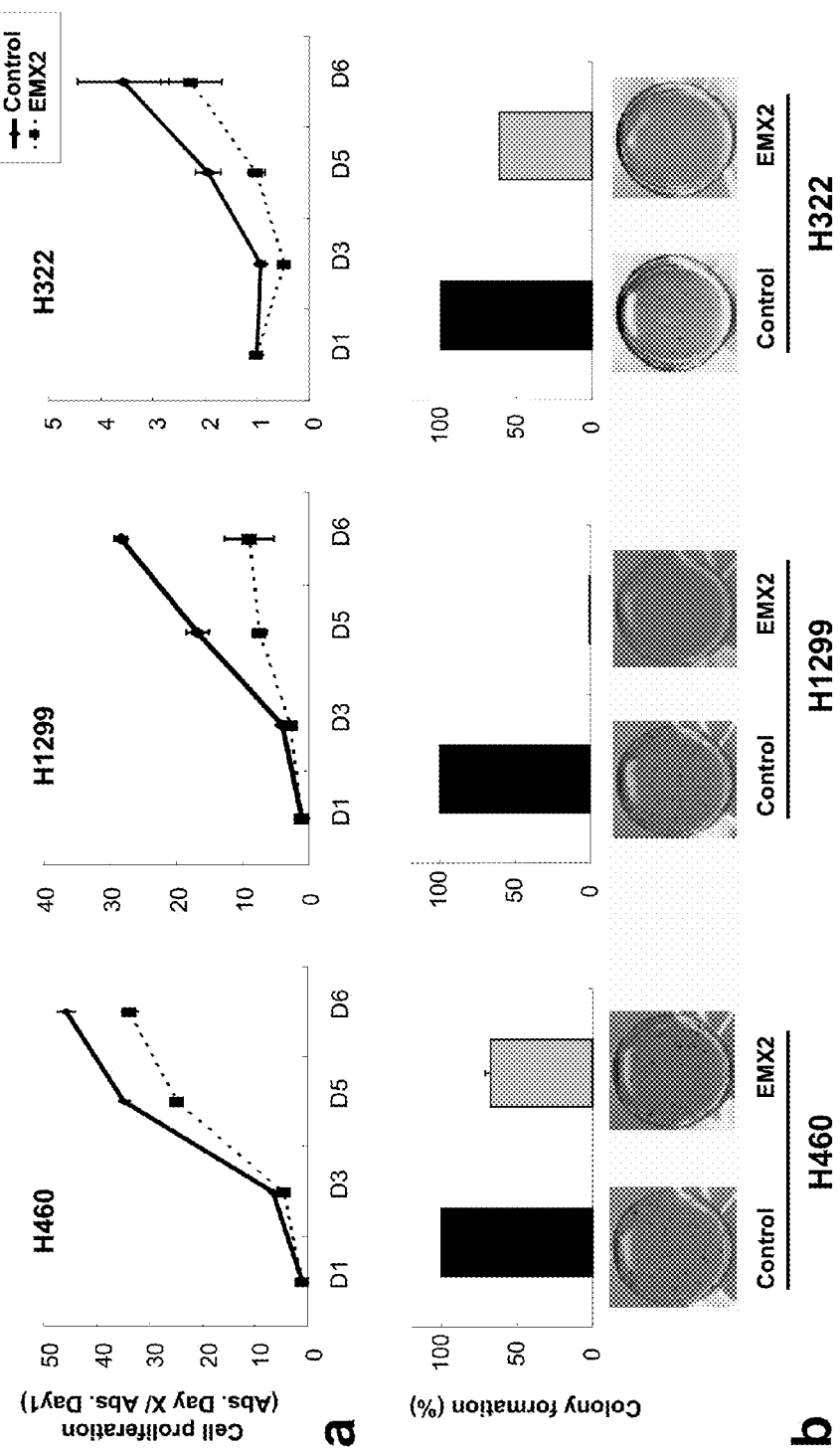
FIG. 8 shows inhibition of the growth of lung cancer cells by the restoration of EMX2 expression in NSCLC cell lines transfected with EMX2 DNA (Panel A). The bar graphs summarize the results of Multicellular Tumor Spheroid ("MTS") proliferation assays. This result is confirmed by the colony formation assays shown in Panel B.

Materials and Methods
Colony Formation Assay
500 cells of each stable line were split into 10 cm plates. Colonies were fixed by 10% formalin and stained with 0.5% crystal violet 10 days after split cells.
Cell Cycle Analysis
Cells were plated in 6-well plates, incubated for 24 hrs and treated with DMSO, 1 µM and 2 µM 17-AAG. For flow cytometry, cells were trypsinized and fixed in 70% ethanol at −20° C., and then washed and stained with 30 µg/ml propidium iodide (Sigma, St. Louis, Mo.) with 10 µg/ml RNase (Roche, Indianapolis, Ind.) for 1 hr at room temperature. Cells were evaluated on a FACScan machine (Becton Dickinson, Franklin Lake, N.J.) and the data were analyzed with ModFit LT 3.1 Mac software for modeling cell cycle distribution. Experiments were performed in triplicate. The data were expressed as mean±S.D.
Results and Analysis
When EMX2 expression was induced in NSCLC cell lines H1299 and H322, a suppression of proliferation was observed (FIG. 8) (in H1299, MTS: p<0.001; Colony formation: p<0.001; and in H322, MTS: p=0.02; Colony formation: p=0.02). Colonies (live cells) were stained by stained 0.5% crystal violet. The MTS result and bar graphs show the average in triplicate experiments. Error bars are standard deviations (S.D.). Thus, EMX2 suppresses the growth of NSCLC cells through inhibition of the Wnt signaling pathway.

Figure 10:
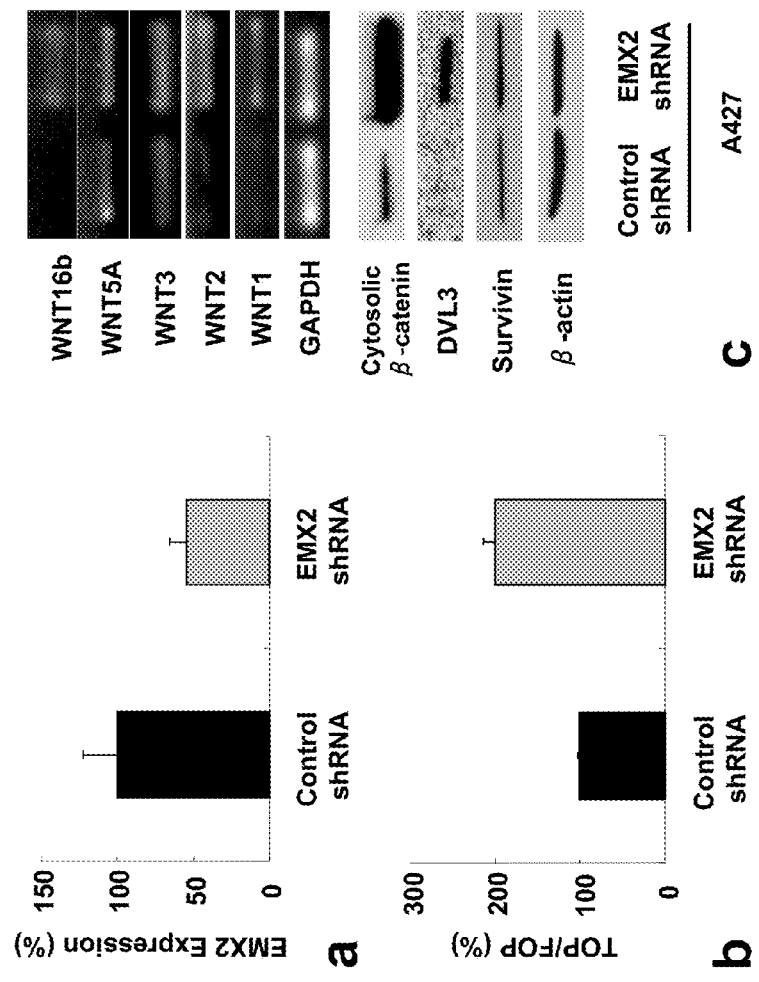
FIG. 10 shows the graphical results of the shRNA-knockdown of EMX2 in NSCLC cell line A427, which normally expresses EMX2. Panel A shows the shRNA knockdown of EMX2. Panel B shows stimulation of the canonical Wnt signaling pathway by EMX2 knockdown as measured by the TOP/FOP reporter assay. Panel C includes ethidium-stained agarose gels and Western blots showing up-regulated expression of several oncogenic Wnt genes as well as expression of several canonical Wnt pathway effectors and downstream target genes when EMX2 hRNA is administered.

In contrast, when endogenous EMX2 expression in NSCLC cell line A427 was silenced by shRNA against EMX2, cell proliferation was stimulated (MTS: p<0.001; Colony formation: p=0.04) (FIG. 10). This result complements and supports the data shown with the H1299 and H322 cells.

Example 6

Figure 9:
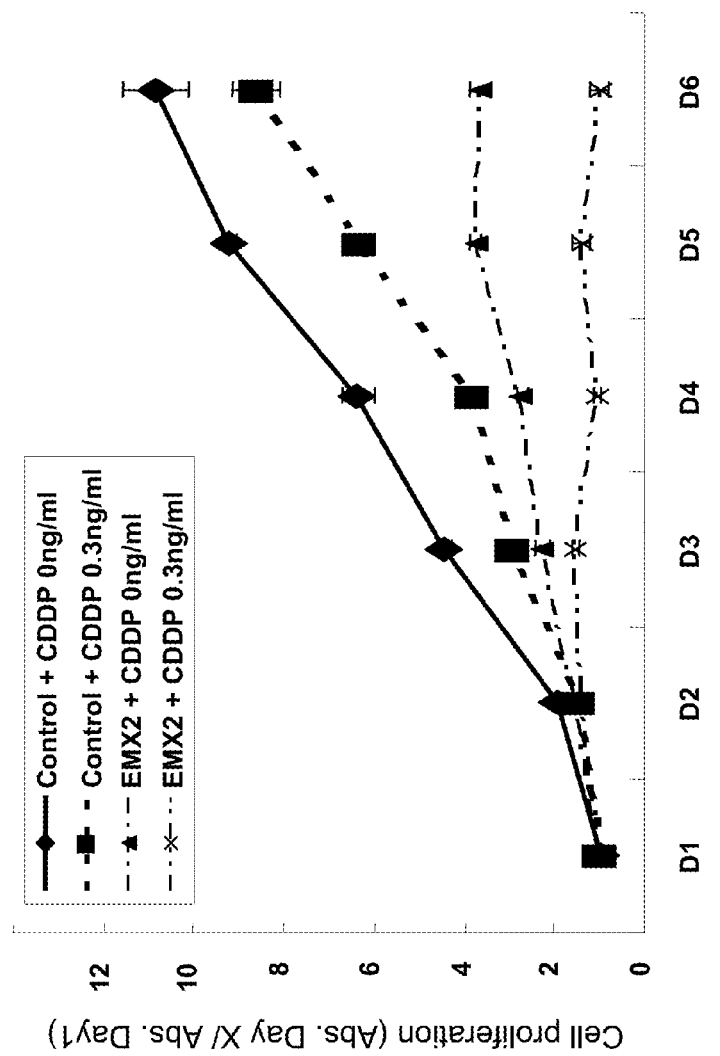
FIG. 9 is a plot showing a chemo-synergic effect between EMX2 and cisplatin as measured by MTS assay. Cell proliferation was more efficiently suppressed by both EMX2 and cisplatin than by CDDP alone in H1299 cells stably transfected with EMX2.

Restoration of EMX2 Expression and Chemotherapy Synergistically Inhibits Growth of Lung Cancer Cells The chemo-synergic effect between EMX2 and cisplatin was examined in order to determine whether EMX2 could sensitize NSCLC cells to cisplatin treatment. The H1299 lung cancer cell line was stably transfected with EMX2 The chemo-synergic effect between EMX2 and cisplatin was measured in this cell line by MTS assay (Promega, Madison, Wis.).
Materials and Methods
MTS Assay
Stable EV- or EMX2 transfected cells were plated in 96-well plates at a density of 500 cells per well in 100 µl of culture medium with G418. Medium was changed every three days. Cell viability was evaluated by CELLTITER 96 Aqueous one solution cell proliferation assay (MTS assay) (Promega, Madison, Wis.) on days 1-7. Briefly, 20 µl of reagent was added to each well and incubated in a culture hood for 2 hr. Absorbance at 490 nm was measured with a kinetic microplate reader (Vmax; Molecular Devices, Sunnyvale, Calif.) and was used as a measure of cell number. Experiments were repeated three times.
Results and Analysis
Although EMX2 stably transfected H1299 cells showed efficient suppression of cell proliferation as compared to control, this effect was further enhanced with the addition of cisplatin (FIG. 9). Chemotherapy is not routinely given to Stage I NSCLC patients prior to surgical resection due to the understanding that surgical treatment alone is sufficient for eradication of a less aggressive form of the disease. These results indicate a therapeutic role for the targeting of EMX2 in combination with current cytotoxic agents.

Example 7

SHRNA-Knockdown of EMX2 Promotes WNT Pathway Signaling in NSCLC Cells Expressing EMX2

The chemo-synergic effect between EMX2 and cisplatin was examined in order to determine whether EMX2 would sensitize NSCLC cells to cisplatin treatment. The slow-growing NSCLC cell line, A427, has previously shown relatively strong expression of EMX2 Therefore, to demonstrate the important role EMX2 plays in lung cancer, shRNA was used to knock down EMX2 expression in A427, which endogenously expresses EMX2.
Materials and Methods
RNA extraction and RT-PCR were performed as described in Examples 1-2.
RNA Interference
A427 cells were plated into a 6-well plate with fresh media without antibiotics 24 hr before transfection. EMX2 shRNAs 1-4 and the control (nonsilencing) shRNA, which does not target any known mammalian gene, were purchased from SUPERARRAY (Frederick, Md.). Transfection was performed by using Lupofectamine 2000 (Invitrogen, Carlsbad, Calif.) according to the manufacturer's instructions. Four kinds of EMX2 shRNA were mixed and used (EMX2 shRNA and a control non-silencing shRNA (25, 50, and 100 µM respectively). After shRNA transfection, cells were further stripped and plated in 10 cm cell culture dishes with G418 (500 ug/ml; Invitrogen) for selection purposes. Stable transfectants were harvested for further analysis after three days and maintained with G418.
Results and Analysis
The knock-down of EMX2 expression was first confirmed by quantitative RT-PCR in EMX2 hRNA transfected cells (FIG. 10). Panel A shows that the shRNA knockdown EMX2 stimulated the canonical Wnt signaling pathway. This was then measured by the TOP/FOP reporter assay (Panel B). In accordance with this result, the expression levels of several oncogenic Wnt genes, as well as the expression levels of several canonical Wnt pathway effectors and downstream target genes, were up-regulated in response to EMX2 shRNA (Panel C). The results indicate that when shRNA is used to knockdown EMX2 this promotes Wnt pathway signaling in lung cancer A427 cells expressing EMX2.

Example 8

SHRNA-Knockdown of EMX2 Promotes Growth of NSCLC Cells Expressing EMX2

A proliferation assay was designed to determine if EMX2 regulates growth of NSCLC cells through regulation of the Wnt signaling pathway. EMX2 expression was blocked in NSCLC cell lines in order to observe whether proliferation increased. Specifically, shRNA was used to knock down EMX2 expression in a NSCLC cell line, A427, which expresses EMX2. An MTS assay was then used to measure the cell proliferation at different time points.
RNA extraction and RT-PCR were performed as described in Examples 1-2.

Results and Analysis

When EMX2 expression was induced in NSCLC cell lines H1299 and H322, a suppression of proliferation was observed (FIG. 11a for H1299) (in H1299, MTS: p<0.001; Colony formation: p<0.001; and in H322, MTS: p=0.02; Colony formation: p=0.02).

Figure 11:
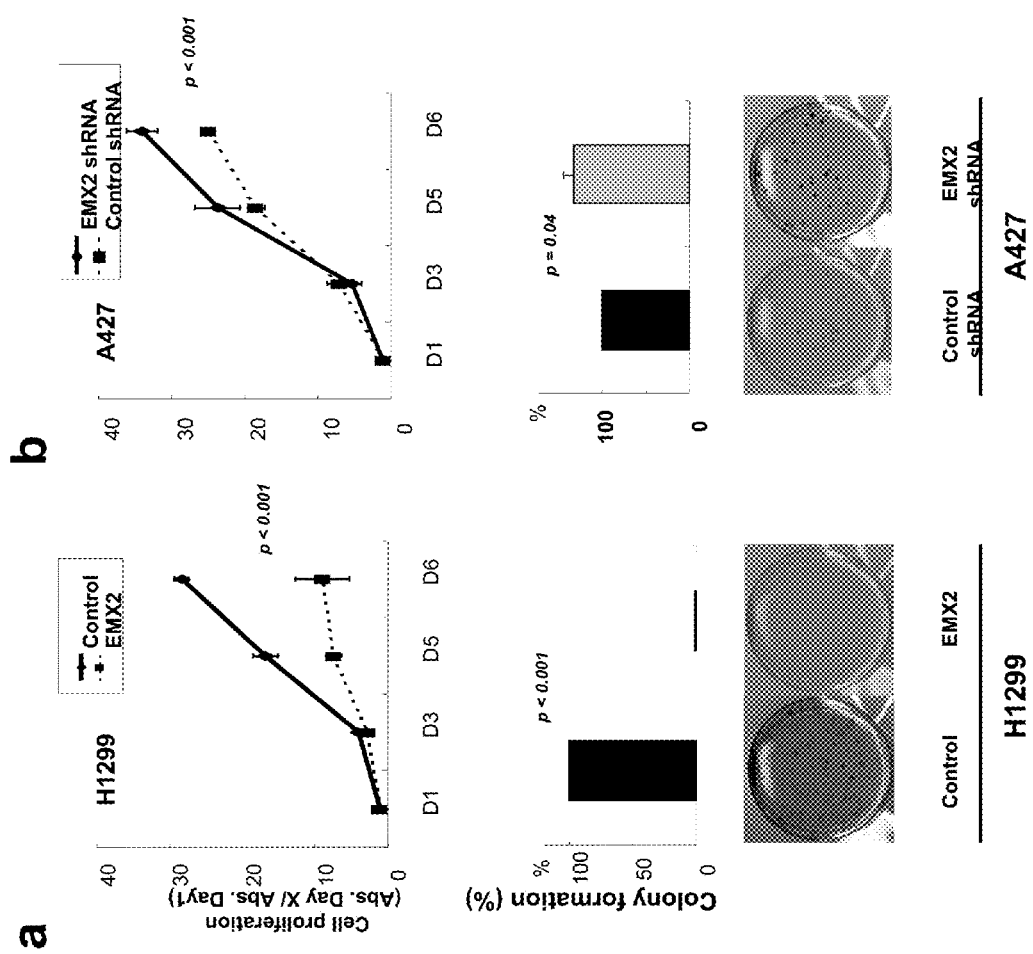
FIG. 11 Panel A shows decreased proliferation of EMX2-transfected H1299 cells (via MTS assay), as well as colony formation assays confirming these results.

In contrast, when endogenous EMX2 expression in NSCLC cell line A427 was silenced by shRNA against EMX2 cell proliferation was stimulated (MTS: p<0.001; Colony formation: p=0.04) (FIG. 11, Panel B). Proliferation of the EMX2 shRNA transfected cells significantly increased compared to that of control shRNA transfected cells (p<0.001). In accordance with this, a colony formation assay also confirmed a significant increase in the number of colonies after shRNA knock-down of EMX2 expression (p=0.02). Colonies were stained by stained 0.5% crystal violet. MTS results show the average in triplicate experiments. Error bars are standard deviations (S.D.).

Example 9

Analysis of EMX2 Function in NSCLC Cells in 3D Cultures

To further assess the function of EMX2 in lung cancer progression, a 3D-organotypic cell culture model was used to mimic an in vivo environment. An organotypic 3D-culture system was established for lung carcinoma cells in order to determine the role of EMX2 in repressing the malignant characteristics of initiated epithelial cells. EMX2 stably transfected H1299 and EMX2 NA-stably transfected A427 cells were used for 3D-culture, and growth characteristics were analyzed over a time period of 7 days.
Materials and Methods
Three-Dimensional Culture (3D-Culture)

Figure 12:
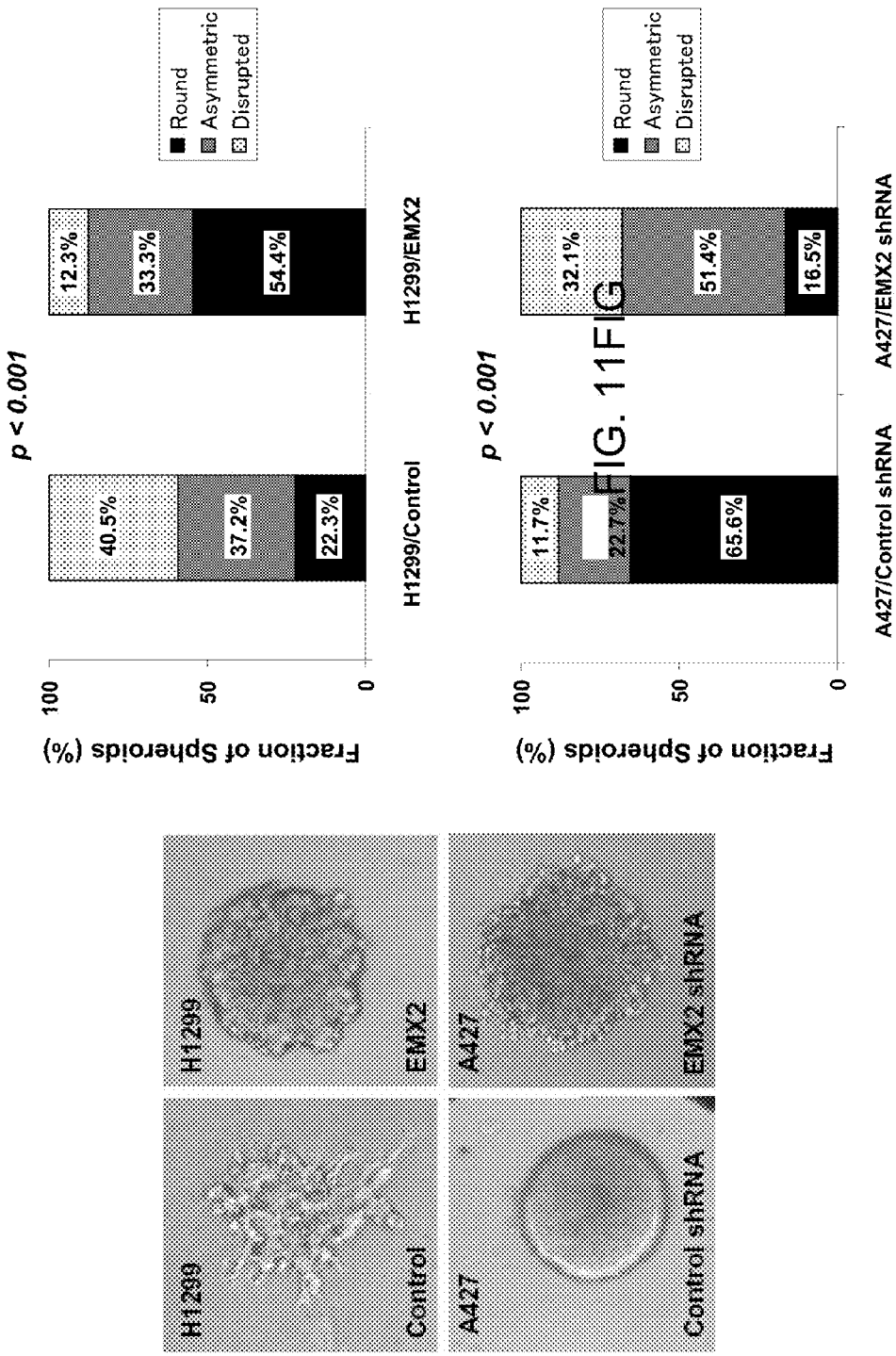
FIG. 12 show images generated from a 3D organotypic cell culture model. In the upper panel, H1299 cells stably transfected with EMX2 show more round and less invasive spheroids than control non-EMX2 expressing H1299 cells. In contrast, the lower panel shows A427 cells transfected with EMX2 DNA having less round and more invasive spheroids than control cells. Phenotypes were quantified in the bar graph to the left (150 spheroids for each treatment were scored and each phenotype was calculated as a percentage of total number of the spheroids. Solid filling area represents smooth branch-less spheroids; dense-dotted area represents spheroids with extending arms; sparse-dotted area represents disrupted non-spherical organoids).

The three-dimensional culture of NSCLC cells on a recombinant basement membrane was carried out as follows. Briefly, eight-chambered culture slides (BD Biosciences) were coated with 35 µl growth-factor reduced Cultrex Basement Membrane Extract (Trevigen, Gaithersburg, Md.) per well and left to solidify for 15 min. H460, H1299 or A427 was treated with trypsin and resuspended in regular culture medium with serum. Cultrex was added to a total concentration of 2%, and 500 µl of the cell suspension was added to each chamber of the Matrigel-coated eight-chambered slide. The assay medium was replaced every 2 days. At least 100 acini were graded for acinar disruption after one week. Following grading, spheres were fixed in 2% PFA at room temperature for 20 min and permeabilized in 0.5% Triton X-100/PBS for 10 min at 4° C. Indirect immunostaining of acinar structures was done as previously described (Debnath J. et al., "Morphogenesis and oncogenesis of MCF-10A mammary epithelial acini grown in three-dimensional basement membrane cultures." *Methods* 30:256-68 (2003).
Results and Analysis Control-non EMX2 expressing H1299 cells formed 3D-spheroids with multiple invasive cellular branch-like structures (i.e., the basal membrane was broken). However, EMX2 stably transfected H1299 cells formed spheroids with a round, less invasive phenotype (p<0.001). (FIG. 12; upper panel). In contrast, A427 cells treated with control shRNA formed more round and less invasive spheroids than those treated with shRNA against EMX2 p<0.001) (FIG. 12; lower panel).

Example 10

Expression of Exogenous EMX2 did not Affect KLE Cells that Endogenously Express EMX2

EMX2 was further studied in the context of growth suppression of NSCLC cells through inhibition of Wnt expression as well as general inhibition of the Wnt signaling pathway.

Figure 13:
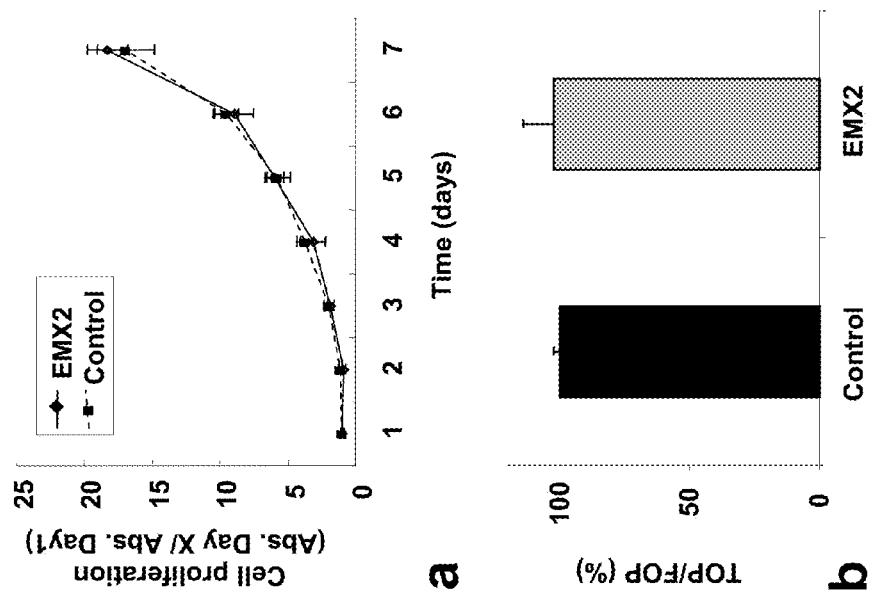
FIG. 13 shows the results of cell proliferation and TOP/FOP assays of EMX2-expressing KLE cells versus control KLE cells which endogenously express EMX2. The values are relatively matched, as expected in this negative control. The MTS results in Panel A are confirmed by the reporter assay results of Panel B. Panel C shows ethidium stained-agarose gels and Western blots of various Wnt effectors in EMX2 expressing KLE cells versus control KLE cells which endogenously express EMX2.

KLE cells, which endogenously express EMX2, were transformed with a vector encoding EMX2. Cell proliferation, Wnt signaling, and the protein levels of typical Wnt effectors were measured in the EMX2 expressing cells, serving the purpose of a negative control.
Materials and Methods EMX2 expressing KLE cells ($2 \times 10^5$) were plated in 6-well plates and transfected with 2 µg of EMX2 DNA/pcDNA3.1 expression vector using LIPOFECTAMIN 2000. After selection with G418 for about one week, stably transfected cells were re-plated in 96-well plates. The MTS assay was used to measure the cell proliferation at different time points.
Results and Analysis Cell proliferation measurements at different time points were roughly identical between the control and the cells transfected with the vector encoding EXM2 (FIG. 13, Panel A). EMX2 expression was confirmed by semi-quantitative RT-PCR in EMX2 DNA transfected cells (data not shown). EMX2 restoration did not inhibit cell proliferation or canonical Wnt signaling as measured by the TOP/FOP reporter assay (FIG. 13, Panel B). In addition, no noticeable changes in protein levels of Wnt effectors, such as Wnt-1, Wnt-16, cytosolic β-catenin and Cyclin D1, etc., were observed in the KLE cells having endogenous EMX2 expression (FIG. 13, Panel C). The MTS result and bar graphs show the average in triplicate experiments. Error bars are standard deviations (S.D.).

Example 11

Figure 14:
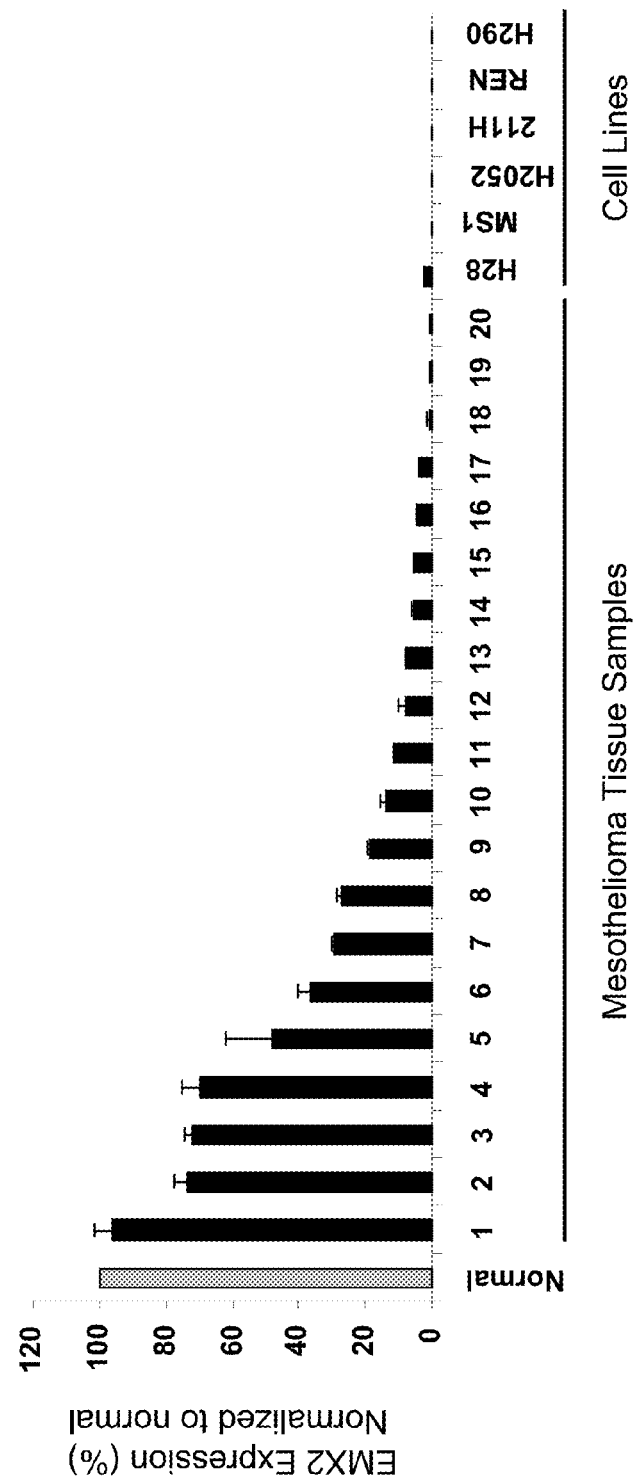
FIG. 14 shows successive down-regulation of EMX2 expression in human primary mesothelioma tissue sample compared to a normal mesothelial tissue sample, as measured by quantitative real-time RT-PCR. The relative expression levels were calculated by normalizing to an internal control, GAPDH, and then to that of adult normal mesothelial tissue which was set as 100%.

Real-Time RT-PCR Analysis of EMX2 Expression in Human Primary Mesothelioma Tissue Samples EMX2 expression levels in human primary mesothelioma were compared to that of normal mesothelial tissues using quantitative real-time RT-PCR. The relative expression levels were calculated by normalizing to the internal control, GAPDH. Quantitative real-time PCR was performed at the UCSF Genome Core Facility. EMX2 as frequently down-regulated in primary mesothelioma tissue samples (FIG. 14). RNA extraction and RT-PCR were performed as described in Examples 1-2.

Example 12

Figure 15:
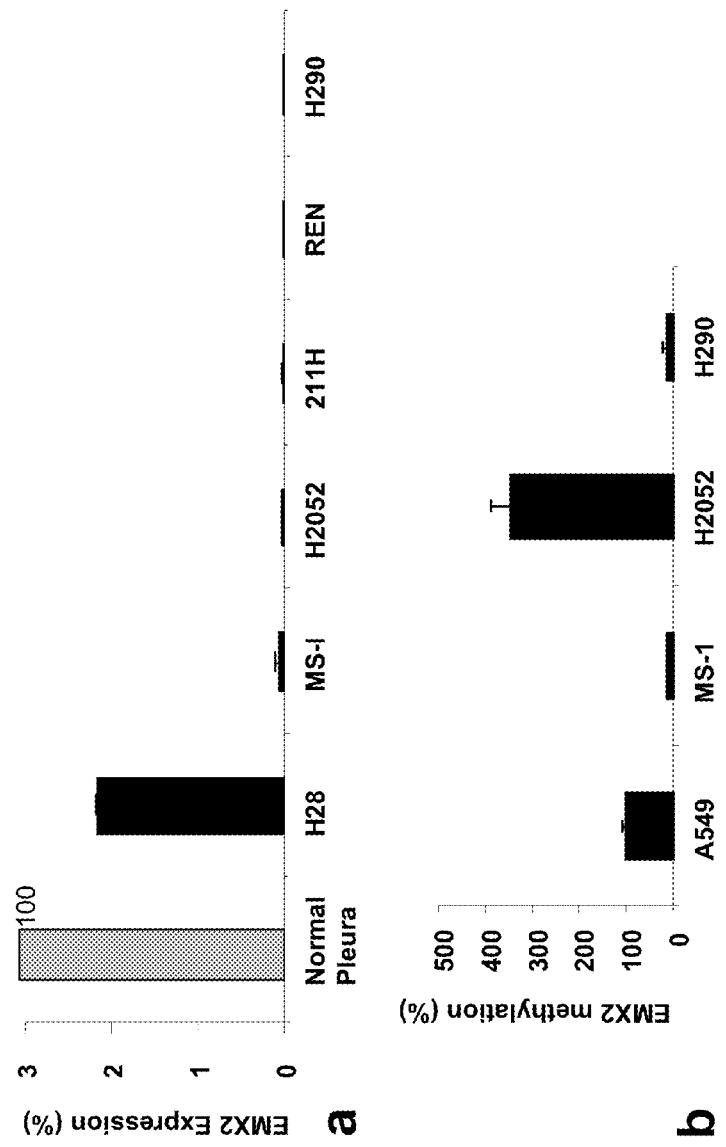
FIG. 15 presents in bar graph form, the results of RT-PCR for EMX2 in various mesothelioma cell lines as compared to a normal tissue sample. Panel A shows loss of EMX2 expression in almost all mesothelioma cell lines examined as compared to the normal pleural control. As before, the relative expression levels were calculated by normalizing to an internal control, GAPDH, and then to that of adult normal mesothelial tissue which was set as 100%. Panel B shows EMX2 methylation as a percentage (%) of EMX2 promoter methylation in cell line A549 (set as 100%) measured by qMSP in human mesothelioma cell lines.

Real-Time RT-PCR Analysis of EMX2 Expression and Methylation Analysis of the EMX2 Promoter in Human Mesothelioma Cell Lines EMX2 expression levels in human mesothelioma cell lines were examined using quantitative real-time RT-PCR, and the relative gene expression levels were calculated by normalizing to the internal control, GAPDH. The EMX2 expression was lost in almost all mesothelioma cell lines examined as compared to the normal pleural control (FIG. 15, Panel A). RNA extraction, RT-PCR and qMSP were performed as described in Examples 1-2.

To examine whether the down-regulation of EMX2 in human mesothelioma cell lines is due to promoter methylation, promoter methylation was performed using quantitative methylation specific PCR (qMSP). EMX2 expression levels correlate with the respective promoter methylation status in all the mesothelioma cell lines that examined (FIG. 15, Panel B).

Example 13

Overall Survival in Mesothelioma Patients

Figure 16:
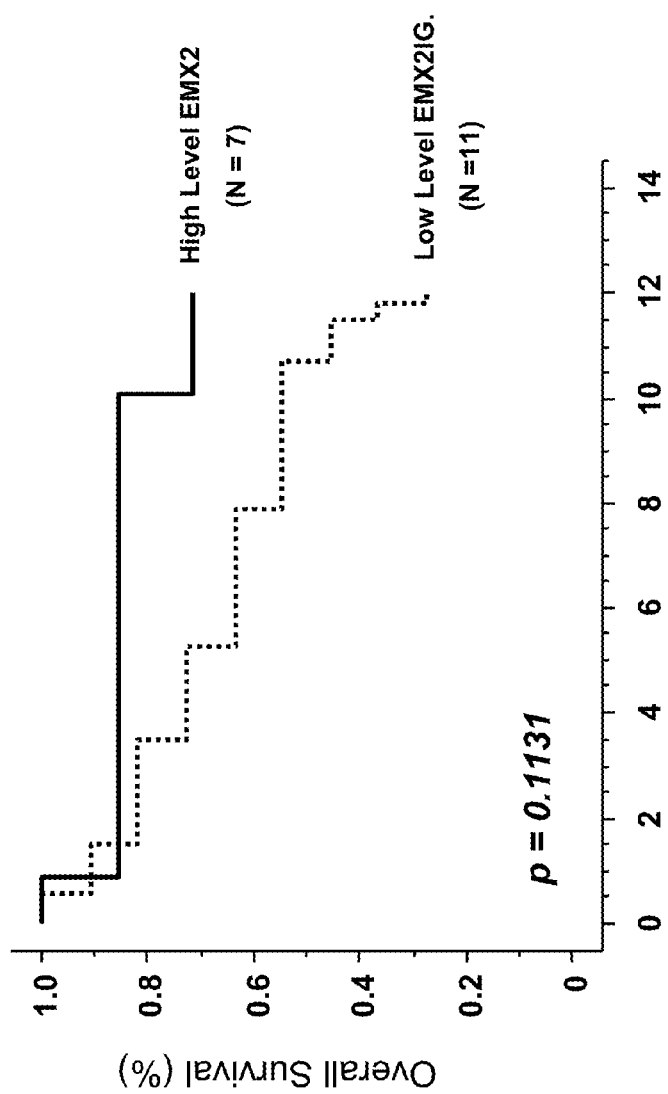
FIG. 16 is a Kaplan-Meier curve showing that overall survival in mesothelioma patients correlates with high levels of EMX2 expression.

Mesothelioma tissue samples were derived from 20 patients. Normal pleural mesothelial tissue sample from one of the mesothelioma patients was used for normalization of EMX2 mRNA expression levels in tumor samples.
Materials and Methods
RNA extraction and real-time RT-PCR were performed as described in Examples 1-2. Statistical analysis was performed as described in Examples 3.
Results and Analysis
Kaplan-Meier survival estimate for 18 Mesothelioma patients over a period of 12 months is presented in FIG. 16. The graphs illustrate that overall survival was improved in patients in the high EMX2 expressing group compared to those in the low EMX2 expressing group in all patients (p=0.1131; the median survival: high (not reached) vs. low (10.6 months)) (FIG. 16). The difference did not reach statistical significance due to the small number of patients analyzed.

Example 14

Figure 17:
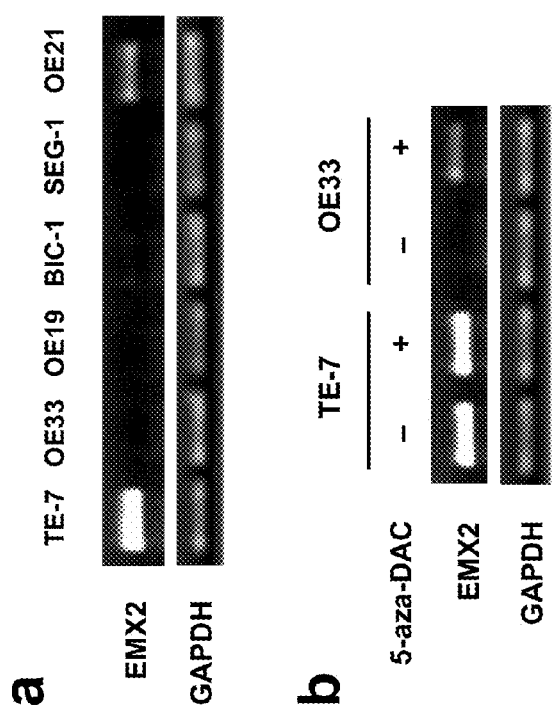
FIG. 17 presents two ethidium-stained agarose gels. Panel A shows little or no expression of EMX2 expression in 4 of the 6 esophageal cancer cell lines tested. As before, EMX2 expression was measured by semi-quantitative RT-PCR, and GAPDH served as an internal control. Panel B shows restoration of EMX2 expression in OE33 cells which did not express EMX2 after de-methylation treatment with DAC.

Semi-Quantitative RT-PCR and Methylation Analysis of EMX2 Expression in Human Esophageal Cancer Cell Lines EMX2 expression levels in human melanoma cell lines were examined using semi-quantitative RT-PCR. As above, GAPDH served as an internal control. Most esophageal cancer cell lines lacked EMX2 expression (FIG. 17, Panel A). After treatment with the de-methylation reagent 5-aza-DAC, EMX2 expression was restored in OE33 cells that did not originally express it (FIG. 17, Panel B). This suggests that EMX2 silencing in esophageal cancer cells is caused by methylation of the EMX2 gene. A negative control confirms that after treatment with 5-aza-DAC, EMX2 expression levels were not affected in TE-7 cells that endogenously expressed EMX2. RNA extraction, RT-PCR and the DAC assay were performed as described in Examples 1-2.

Example 15

Real-Time RT-PCR Analysis of EMX2 Expression in Human Colon Cancer Cell Lines

Figure 18:
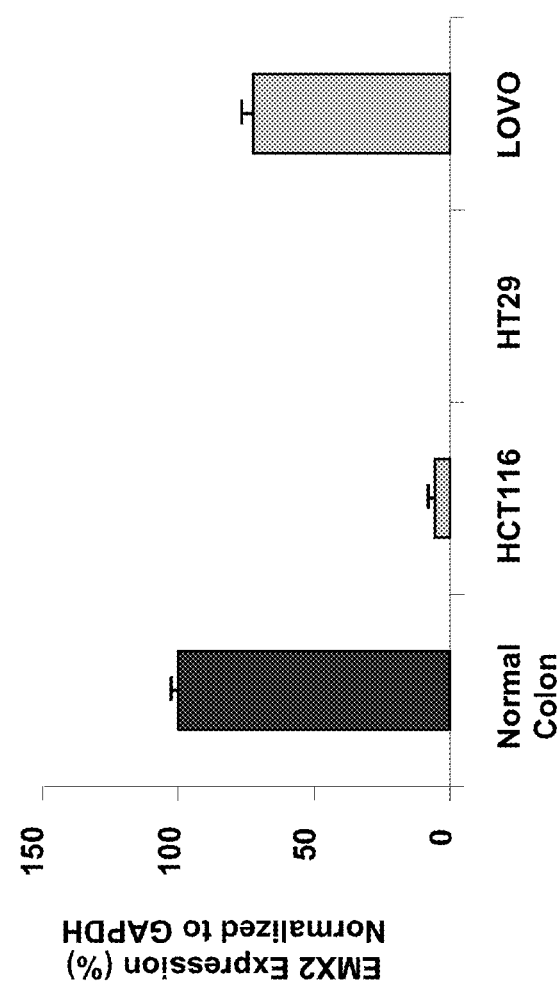
FIG. 18 presents a bar graph of EMX2 expression (y-axis) versus a normal colon tissue sample and three human colon cancer cell lines (x-axis). The expression levels of EMX2 in the human colon cancer cell lines was measured by quantitative real-time RT-PCR and relative expression was calculated by normalizing to the internal control, GAPDH. As can be seen, the normal colon sample expressed EMX2 but colon cancer cell lines expressed less or no EMX2

EMX2 expression levels in human colon cancer cell lines were examined using quantitative real-time RT-PCR, and relative expression levels were again calculated by normalizing to the internal control, GAPDH. Total RNA from a normal colon tissue sample was used as the positive control. While the normal colon tissue sample expressed EMX2, colon cancer cell lines expressed less or lacked EMX2 expression altogether (FIG. 18). RNA extraction and RT-PCR were performed as described in Examples 1-2.

Example 16

Figure 19:
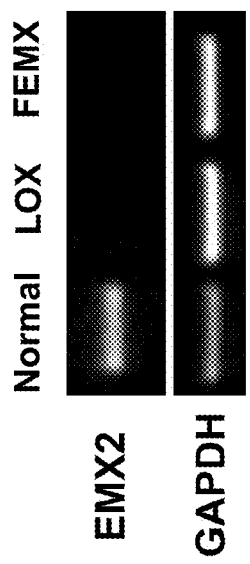
FIG. 19 is an ethidium-stained agarose gel show the expression of EMX2 in two human melanoma cell lines, versus normal skin cell line. As can be seen, the normal control expressed EMX2 but the two melanoma cell lines did not.

Semi-Quantitative RT-PCR Analysis of EMX2 Expression in Human Melanoma Cell Lines EMX2 expression levels in human melanoma cell lines were examined using semi-quantitative RT-PCR, and GAPDH served as an internal control. A normal skin cell line was used as a positive control. While normal skin cells expressed EMX2 all melanoma cell lines failed to express EMX2 (FIG. 19). RNA extraction and RT-PCR were performed as described in Examples 1-2.

Example 17

EMX2 Suppresses Human Lung Cancer Through Inhibition of the WNT Signaling

Lung cancer is the most common cancer and the leading cause of cancer-related death worldwide. The WNT signaling pathway plays important roles in biological processes ranging from embryogenesis to tumorigenesis. Aberrant activation of WNT signaling is also strongly implicated in lung carcinogenesis. EMX2, a human homologue of the *Drosophila* empty spiracles gene is a homeodomain-containing transcription factor. The function of EMX2 has been linked to the WNT signaling pathway during embryonic patterning in mice. However, little is known about the role of EMX2 in human tumorigenesis. In this study, we demonstrate that EMX2 was dramatically down-regulated in lung cancer tissue samples and this down-regulation was associated with methylation of the EMX2 promoter. Restoration of EMX2 expression in lung cancer cells lacking endogenous EMX2 expression suppressed cell proliferation and invasive phenotypes, inhibited transcription of oncogenic WNT genes and canonical WNT signaling, and sensitized lung cancer cells to the treatment of the chemo cytotoxic drug cisplatin. On the other hand, knock-down of EMX2 expression in one lung cancer cell line expressing endogenous EMX2 promoted cell proliferation and an invasive phenotype, as well as upregulated transcription of oncogenic WNT genes and canonical WNT signaling. Taken together, our study suggests that EMX2 may play important roles as a novel suppressor in human lung cancer.
Introduction
The American Cancer Society (ACS) lists lung cancer as the leading cause of cancer death in the U.S. with over 160,000 deaths forecasted in 2009. These lung cancer deaths represent 29% of all cancer mortality, a figure exceeding all deaths from the next four most deadly cancers, i.e. breast, colon, prostate and pancreatic cancers combined (American Cancer Society, *Cancer facts and figures* (2008)). Lung cancer is conventionally divided into two main types: non-small cell lung cancer (NSCLC) comprising nearly 80% of the total, and small cell lung cancer comprising the other 20%. Within NSCLC, there are three distinct histological subtypes: adenocarcinoma (which itself accounts for 40% of all lung cancers), squamous cell carcinoma and large cell carcinoma. The mainstays of conventional therapy, surgery, radiation, and chemotherapy, have offered patients only a limited and generally short-term benefit. Overall five-year survival has remained at a dismal 14-15% for over two decades (American Lung Association, *Trends in lung cancer morbidity and mortality* (2007)). The molecular carcinogenesis of lung cancer is characterized by multiple alterations of gene expression and function. These arise from a series of molecular and morphological events affecting oncogenes such as K-ras and EGFR (Fong K M et al., *Thorax* 58:892-900 (2003)) and tumor suppressor genes such as p53 and p16 (Zochbauer-Muller S et al., *Clin Lung Cancer* 2:141-5 (2000)), all leading inexorably to abnormal changes in cell signaling transduction pathways.

The WNT pathway plays an important role in embryogenesis, stem cell renewal and oncogenesis (Klaus A and Birchmeier W., *Nat Rev Cancer* 8:387-98 (2008)). Mutations in key WNT signaling genes such as APC or β-catenin, frequently associated with colon cancer, seem to be rare in lung cancer (Königshoff M and Eickelberg O., *Am J Respir Cell Mol Biol* (2009) March 27 [PMID: 19329555]). Methylation-silencing of secreted WNT antagonists: WNT Inhibitory Factor-1 (WIF-1) and secreted Frizzled-related proteins (sFRPs) has been reported to be associated with aberrant WNT activation in lung cancer (Mazieres J et al., *Cancer Res* 64:4717-20 (2004); He B et al., *Cancer Res* 65:743-8 (2005)). Moreover, over-expression of several WNT genes may be critical to WNT activation and lung cancer growth (He B et al., *Neoplasia* 6:7-14 (2004); You L et al., *Oncogene* 23:6170-4 (2004); Huang C L et al., *Eur J Cancer* 44:2680-8 (2008); Akiri G et al., *Oncogene* 28:2163-72 (2009)). How the transcription of WNT genes is regulated in lung cancer remains to be elucidated.

The homeobox gene family encodes transcription factors, regulating morphogenesis and cell differentiation during embryogenesis by activating or repressing the expression of target genes (Boersma C J et al., *Mol Cell Biol Res Commun* 2:117-24 (1999)). In addition, several homeobox genes have recently been shown to be associated with cancers (Raman V et al., *J Biol Chem* 275:26551-5 (2000); Abate-Shen C., *Nat Rev Cancer* 10:777-85 (2002); Samuel S and Naora H., *Eur J Cancer* 16:2428-37 (2005); Yoshida H et al., *Cancer Res* 2:889-97 (2006)). EMX2 is a human homologue of the *Drosophila* empty spiracles gene (ems), a homeodomain-containing transcription factor with important functions during early development. For example, mice harboring homozygous mutation of EMX2 (EMX2−/−) exhibit small cerebral hemispheres and olfactory bulbs (Dalton D et al., *Genes Dev* 3:1940-56 (1989)). EMX2 affects the proliferation of adult neural stem cells (ANSCs) by regulating the frequency of symmetric divisions that generate two stem cells within the ANSC population, and over-expression of EMX2 decreases the frequency of symmetric divisions (Galli R et al., *Development* 129:1633-44 (2002)). EMX2 controls mammalian reproduction by adjusting endometrial cell proliferation without effecting differentiation (Taylor H S and Fei X, *Mol Endocrinol* 19:2839-46 (2005)). Moreover, it has been reported that EMX2 is a direct repressor of WNT1 expression with loss of EMX2 function leading to ectopic WNT1 expression in the developing mammalian telecephalon, resulting in cortical dysplasia (Ligon K L et al., *Development* 130:2275-87 (2003)). There have been only a limited number of recent studies suggesting possible involvement of EMX2 in human cancer. For example, EMX2 may be anti-proliferative in the endometrium and its expression is decreased in endometrial tumors (Noonan F C et al., *Genomics* 76:37-44 (2001); Noonan F C et al., *Genomics* 81:58-66 (2003)). EMX2 also displayed methylation but rarely in non-seminomas (Lind G E et al., *J Pathol* 210:441-9 (2006)). The role of EMX2 in tumorigenesis, however, is still largely unknown. In this study, we seek to investigate the role of EMX2 and the mechanisms of transcriptional regulation of aberrantly activated WNT signaling in human lung cancer.

Materials and Methods

Tissues and RNA Extraction. Fresh samples (lung cancer tissue and its adjacent normal tissue) were collected from patients undergoing surgical resection with approval by the Committee on Human Research at the University of California, San Francisco (UCSF). Samples were promptly snap-frozen in liquid nitrogen and stored at −170° C. before use. Total RNA was extracted using TRIzol LS (Invitrogen).

Quantitative Real-time Reverse Transcription PCR. cDNA synthesis and Taqman PCR were performed as previously described (Raz D et al., *Clin Cancer Res* 14:5565-70 (2008)). Hybridization probes and primers (FIG. 26) were purchased from Applied Biosystems (ABI). EMX2 expression was assayed in triplicate using an ABI 7300 Real-time PCR System. Samples were normalized to their housekeeping gene GAPDH and expression levels were calculated using the $2^{-ddCt}$ method, compared to total RNA of adult normal lung tissue (BioChain).

Quantitative Methylation-specific PCR (qMSP). qMSP was performed as previously described (Fackler M J et al., *Cancer Res* 64:4442-52 (2004); Grote H J et al., *Cancer* 108:129-34 (2006); Grote H J et al., *Int J Cancer* 116:720-5 (2005); Kempkensteffen C et al., *J Cancer Res Clin Oncol* 132:765-70 (2006); Harden S V et al., *Clin Cancer Res* 9:1370-5 (2003)). Genomic DNA from cell lines and tissue samples was extracted with Qiagen DNeasy kits and bisulfite modification of genomic DNA was performed using EZ DNA Methylation-Gold Kits (Zymo Research) per manufacturers' protocols. Primers and probes were designed using Primer Express® and Methyl Primer Express® Software v1.0 (ABI) and purchased from Operon (FIG. 26). Relative EMX2 methylation levels were determined by using the $2^{-dCt}$ method (normalizing to the housekeeping gene ACTB (Raz D et al., *Clin Cancer Res* 14:5565-70 (2008))) and then calculating the ratio (tumor/matched normal for tissues; cell line/an adult normal lung tissue (BioChain) for cell lines). PCR cycling conditions were: 95° C. for 10 min, 95° C. for 15 s and 58° C. for 1 min for 50 cycles. qMSP was done in triplicate using an ABI 7300 Real-time PCR System and each experiment was repeated three times.

Cell Culture and 5-Aza-2'-deoxycytidine (DAC) Treatment. Human lung cancer cell lines H460, A549, H1703, H838, H1975, A427, H2170, H1666, H1299, H522, H322, and H441 were purchased from American Type Culture Collection (ATCC). Genomics, Proteomics and immunology technologies are used to characterize cell lines at ATCC. Experiments were performed within 3 months after resuscitation of each cell line. They were cultured in RPMI 1640 with 10% fetal bovine serum, penicillin (100 IU/ml)/streptomycin (100 μg/ml) at 37° C. in a humidified 5% $CO_2$ incubator. Total RNA from cell lines was isolated using Qiagen RNeasy kit. Treatment of cells lines with 5 μM 5-aza-2'-deoxycytidine (DAC) (Sigma) was performed as previously described (Mazieres J et al., *Cancer Res* 64:4717-20 (2004)).

Transfection and RNA Interference. pcDNA 3.1/EMX2 mammalian expression-vector was subcloned from pCMV6-XL5/EMX2 vector (Origene). EMX2 shRNAs and control (non-silencing) shRNA (all are in pRFP-C-RS vector) were purchased from Origene. The targeted EMX2 sequences are: 5'-TCAAGCCATTTACCAGGCTTCGGAGGAAG-3' (SEQ ID NO:27) and 5'-CGGTGGAGAATCGCCACCAAGCAG-GCGAG-3' (SEQ ID NO:28). Cell lines were plated in six-well plates with fresh media without antibiotics for 24 hrs before transfection. Transfection was performed using Lipofectamine2000 (Invitrogen) per manufacturer's protocol. Transfected cells were re-plated in 10 cm dishes for selection with G418 (500 μpg/ml; Invitrogen). Stable transfectants were maintained in regular medium with G418 (300 pg/ml) for further analysis.

Proliferation Assays. Stably transfected cells were plated in 96-well plates at a density of 500-1000 cells/well in 100 μl of G418 culture medium. Medium was changed every day. Cell viability was evaluated in triplicate by CellTiter 96 AQueous (Promega) per manufacturer's protocol. For colony formation assay, 500 individual cells of the stable lines were seeded in 10 cm dishes and cultured for 10 days. Colonies were then fixed by 10% formalin, stained with 0.5% crystal violet and counted.

Colony Formation in Soft Agar. One thousand cells were seeded into 60-mm dishes in a suspension of 0.5% bacto-agar (Difco) in medium supplemented with 10% fetal calf serum on top of a bed of 0.5% bacto-agar (Difco) in the same medium. Cells were plated on top of 1 ml of 0.5% agarose. Plates were incubated at 37° C. in 5% CO2, and colonies formed after 15-30 days incubation were counted. Cells were seeded in triplicate.

Cell Invasion Assay. Invasion assays were carried out using BD BioCoat Matrigel Invasion Chamber according to the manufacturer's protocol in triplicate for each transfectant. Cells from five different fields of each insert membrane were counted under a light microscope (40×) and the percent invasion was determined as follows: % Invasion=(Mean # of cells invading through matrigel insert membrane/Mean # of cells migrating through control insert membrane without matrigel)×100.

TOP/FOP and WNT Promoter-reporter Assays. Performed 24 hrs after transfection as previously described (Clement G et al., *Cancer Sci* 99:46-53 (2008); Reguart N et al., *Biochem Biophys Res Commun.* 323:229-34 (2004)).

Western Blot. Performed as previously described (Clement G et al., *Cancer Sci* 99:46-53 (2008)). Primary antibodies used include: β-catenin (BD Biosciences), Cyclin D1 (Cell Signaling Technology), and β-actin (Sigma). Cytosolic proteins were prepared by using NE-PER Nuclear and Cytoplasmic Extraction Reagents (Cat# 78833) (Pierce Biotechnology) according to the manufacturer's protocol.

Three-dimension (3D) Culture. Eight-chambered culture slides (BD) were coated with 35 µl growth-factor reduced Cultrex Basement Membrane Extract (Trevigen) per well and left to solidify for 15 min. H1299 or A427 cells were treated with trypsin and resuspended in regular culture medium with serum. Cultrex was added to a total concentration of 2%, and 500 µl of the cell suspension was added to each chamber of the Matrigel-coated slide. Medium was replaced every 2 days. After one week, 100+ acini were graded for disruption. Following grading, spheres were fixed in 2% PFA at room temperature for 20 min and permeabilized in 0.5% Triton X-100 in PBS for 10 min at 4° C. Indirect immunostaining of acinar structures was performed.

Statistical Analysis. All data were calculated as means±standard deviations. Differences between groups were compared with a two-sided student's t-test. A p value of 0.05 or less was considered to be significant.

Results

EMX2 Expression is Down-regulated by Methylation in Lung Cancer

Figure 21:
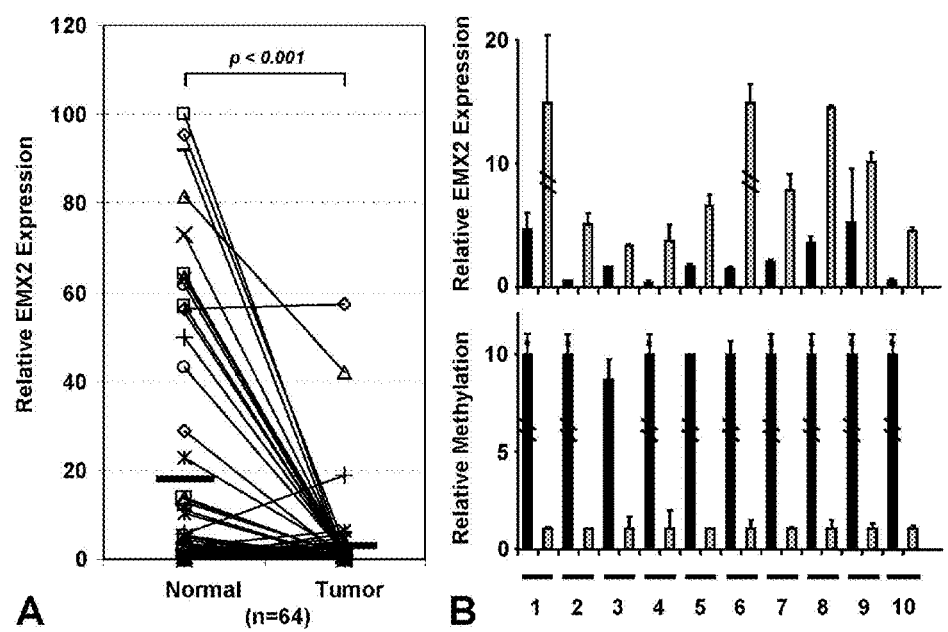
FIG. 21. EMX2 expression is down-regulated by methylation in lung cancer tissue samples. (A) Quantitative RT-PCR of 64 tumors and their matched adjacent normal lung tissues. Y-axis represents normalized relative EMX2 mRNA expression (arbitrary unit). (B) Quantitative RT-PCR (upper panel) and quantitative MSP (lower panel) of 10 representative tumors compared with their matched adjacent normal lung tissues.
Figure 22:
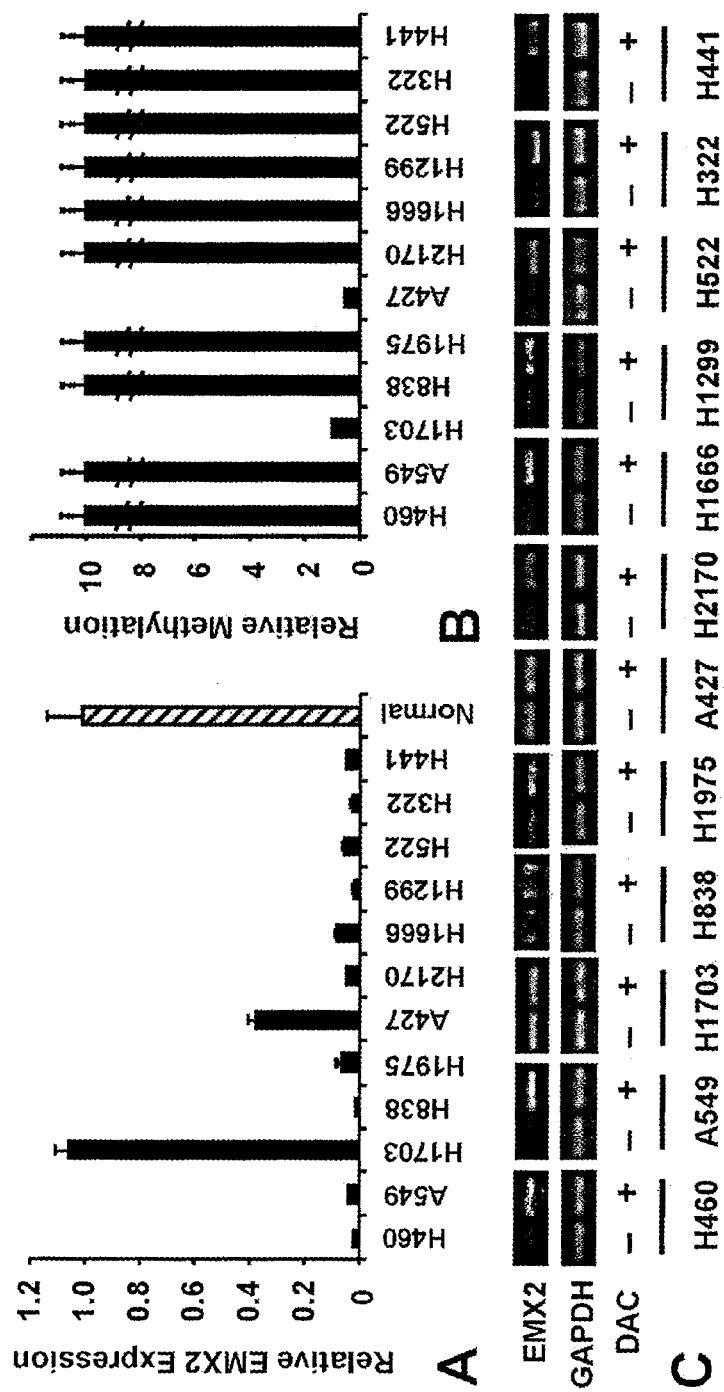
FIG. 22. EMX2 expression is down-regulated by methylation in lung cancer cell lines. (A) Quantitative RT-PCR analysis. An adult normal lung tissue was used as a control. (B) Quantitative MSP analysis. (C) DAC treatment of lung cancer cell lines. 72 hours 5 µM after treatment, EMX2 expression was examined by semi-quantitative RT-PCR. GAPDH served as control for RNA quality and loading.

We first examined the mRNA levels of EMX2 in human lung cancer tissues samples and their matched adjacent normal tissues obtained from 64 patients with lung cancer. Upon comparison 71.8% (46 of 64) lung cancer samples analyzed were found to have less EMX2 expression that their matched adjacent normal tissues (FIG. 21A) and this down-regulation was statistically significant (mean values of EMX2 expression measured by quantitative RT-PCR were 3.78 and 18.01 in cancer tissues and their matched adjacent normal tissues, respectively; p<0.001). Diminished/absent EMX2 expression was consistently associated with hypermethylation of the EMX2 promoter in these cases evaluated by qMSP (FIG. 21B showed an example of ten paired tissue samples). We also analyzed EMX2 expression and the EMX2 promoter methylation status in 12 lung cancer cell lines to verify these results. 10 of the 12 lines examined were found to lack EMX2 expression (FIG. 22A). Using qMSP we found that the EMX2 promoter in the same 10 cells lines was also methylated (FIG. 22B). Next, using a demethylating reagent DAC we restored EMX2 expression in cell lines with initially silenced EMX2 (FIG. 22C). These data indicate that EMX2 promoter methylation suppresses EMX2 expression in lung cancer.

EMX2 Inhibits Proliferation and Metastatic Phenotype of Lung Cancer Cells

Figure 23:
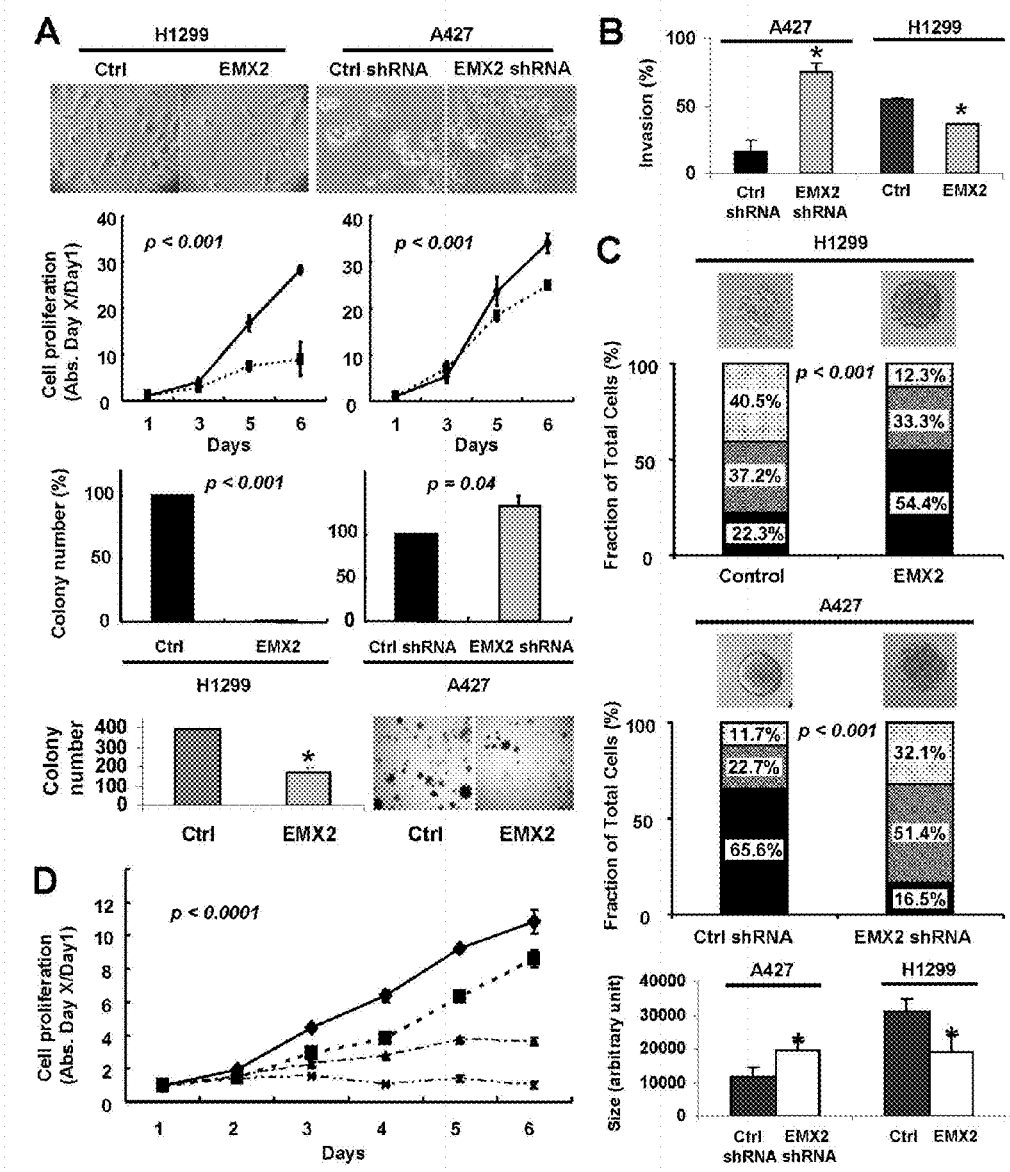
FIG. 23. Restoration of EMX2 expression suppressed lung cancer cell proliferation and sensitized lung cancer cells to cisplatin. (A) From top to bottom are morphology under light microscope (40×); MTS assay; colony formation assay, and soft agar assay in H1299 cells stably transfected with EMX2 (pictures were taken under light microscope (20×)), respectively. In both MTS and colony formation assays, left is H1299 cells stably transfected with EMX2 (solid diamonds; empty pCDNA3.1 vector was used as control (solid squares)); and right is A427 cells stably transfected with EMX2 shRNA (solid squares; non-silencing shRNA was used as control (solid diamonds)). Controls were set as 100%; (B) Invasion assay using trans-well chamber with and without matrigel. (C) Analyses of 3D cultures of H1299 cells stably transfected with EMX2 and A427 cells stably transfected with EMX2 shRNA. Phenotypes of spheroids were categorized into 3 types (round (solid filling), asymmetric (dense-dotted), and disrupted (sparse-dotted)) and quantified. Representative phenotypes in each treatment were shown. Bottom is quantification of size of spheroids. (D) Synergistic effect between EMX2 and cisplatin in H1299. Diamonds, squares, triangles, and crosses are treatments of control vector alone, control vector+cisplatin (0.3 ng/ml), EMX2 cDNA alone, and EMX2 cDNA+cisplatin (0.3 ng/ml), respectively. Results are Means±S.D. (error bars).
Figure 27:
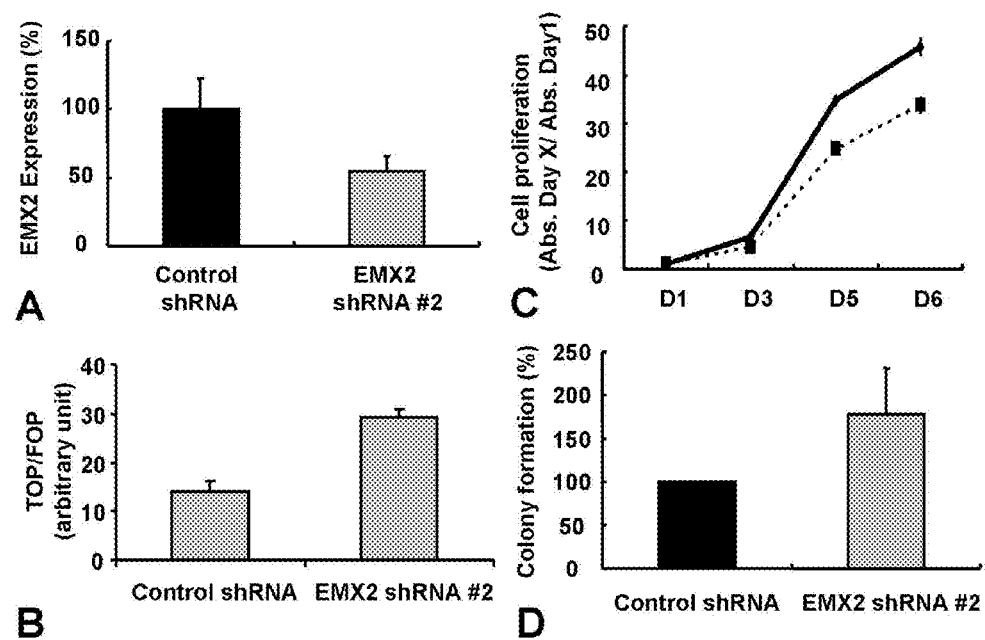

We next investigated the roles of EMX2 in the growth of lung cancer cells in which EMX2 was methylation-silenced. One week after transfection and subsequent G418 selection, we found that EMX2 restoration in H1299 led to significant proliferative suppression (MTS: p<0.001; Colony formation assays: p<0.001) without dramatic morphological changes (FIG. 23A). In contrast, when endogenous EMX2 expression in A427 was silenced by anti-EMX2 shRNAs, cell proliferation was stimulated (MTS: p<0.001; Colony formation: p=0.04) with dramatic morphological changes (cells were larger with more branches after EMX2 shRNA treatment) (FIG. 23A and FIGS. 27C, 27D). These results complement and support the data observed in H1299 cells.

To further assess the function of EMX2 in lung cancer progression, we performed a cell invasion assay and found that the percent invasion of EMX2-stably transfected H1299 cells was significantly reduced (p<0.05) and that the percent invasion of EMX2 shRNA-stably transfected A427 cells was significantly increased (p<0.05) (FIG. 23B). Consistently, when we investigated phenotypes of those transfectants using a 3D-spheriod model to mimic an in vivo microenvironment, we found that control (non-EMX2 expressing) H1299 cells formed 3D-spheroids with multiple invasive cellular branch-like structures indicating broken basal membrane. However, EMX2-stably transfected H1299 formed a less invasive rounder phenotype (p<0.001) (FIG. 23C). In contrast, A427 cells treated with control shRNA formed more round/less invasive spheroids than those treated with EMX2 shRNA (p<0.001) (FIG. 23C). In addition, it appeared that EMX2-stably transfected H1299 formed smaller spheroids (p<0.05) and EMX2 shRNA-stably transfected A427 formed larger spheroids (p<0.05) (FIG. 23C). Together, our results suggest that EMX2 may play a role as a suppressor of malignant lung cell progression.

EMX2 Sensitizes Lung Cancer Cells to Cisplatin Treatment

Cisplatin is widely used in the clinic to treat lung cancer. Using H1299 stably transfected with EMX2, we examined the chemosynergic effect between EMX2 and cisplatin (FIG. 23D). We observed that the suppressive potential of moderate doses of cisplatin was significantly enhanced by re-expressing EMX2 in H1299 cells (p<0.0001), indicating the potential future therapeutic role for EMX2 in combination with current cytotoxic agents in lung cancer.

EMX2 Suppresses the Canonical WNT Pathway in Lung Cancer Cells

Figure 24:
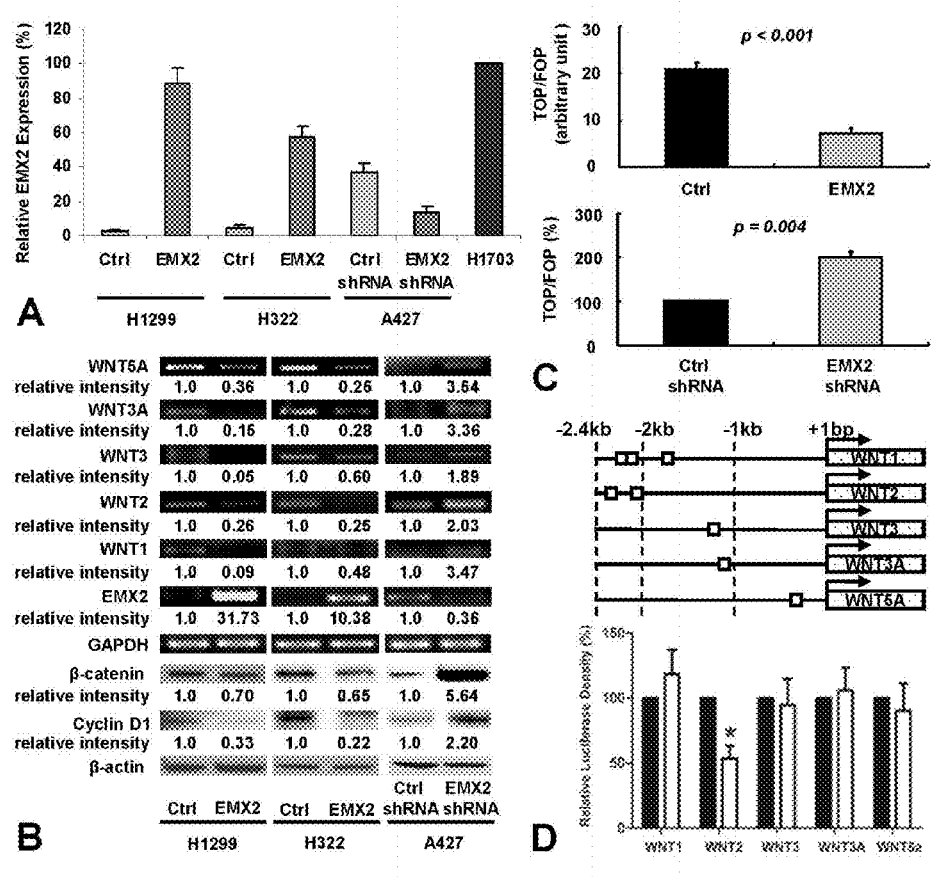
FIG. 24. EMX2 suppressed transcription of WNT genes and canonical WNT signaling in lung cancer cell lines. (A) Quantitative RT-PCR of EMX2 expression in cell lines stably transfected with control or EMX2 expression vector (in H1299 and H322) and with non-silencing control or EMX2 specific shRNA (in A427). H1703 served as a EMX2 expression level control. (B) Semi-quantitative RT-PCR of WNT genes. RT-PCR was performed using Invitrogen one-step RT-PCR kit. GAPDH served as RNA control. Western blotting of key canonical WNT downstream effector (cytosolic β-catenin) and target protein (Cyclin D1) was shown below the RT-PCR results. β-actin was used as protein control. The relative intensity value of each band (gene or protein X) in EMX2 cDNA and shRNA transfectants was measured in Photoshop and calculated by normalizing to relative intensity value of gene X/GAPDH (or protein X/β-actin) in each control which was set as 1.0. (C) TOP/FOP luciferase assays of transcription activity of the canonical WNT pathway in H322 cells stably transfected with EMX2 cDNA (top); and in A427 cells stably transfected with EMX2 shRNA (bottom), respectively. (D) Top is schematic of promoter regions of human WNT genes. Putative EMX2 binding sites (TAATT) are shown as open boxes. Sequences were obtained from human genome sequence database (http://genome.ucsc.edu). Bottom is luciferase-reporter assay of the WNT promoters in 293T cells transfected with EMX2 expression vector. All WNT promoters (~1.0-1.5 kb in length including putative EMX2 binding sites) were inserted in a pGL3 basic vector (pGL3B) upstream of the Firefly Luciferase gene. Detailed method of the promoter cloning is as previously described (Reguart N et al., *Biochem Biophys Res Commun.* 323:229-34 (2004)). The average mean±SD (errors bars) values are shown.
Figure 28:
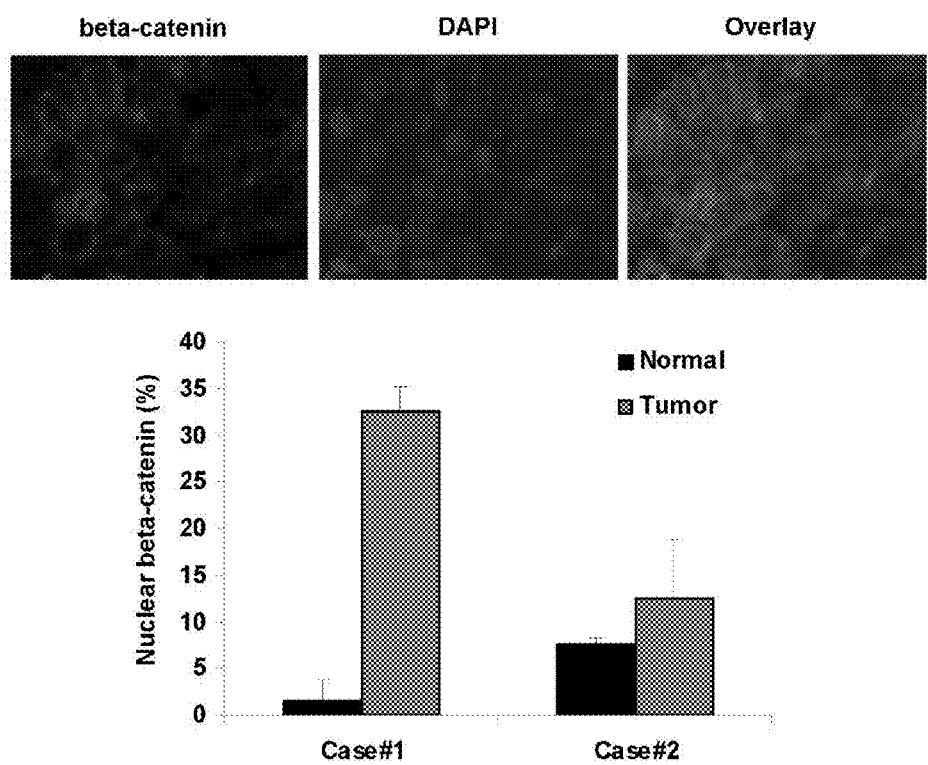
FIG. 28. Example of immunofluorescent (IF) staining of beta-catenin and score of nuclear beta-catenin in human lung cancer tissue samples. Mouse monoclonal β-catenin antibody was purchased from BD Biosciences. IF staining was performed according to standard protocol previously described (DeNardo D G, et al., *Cancer Cell* 16(2):91-102 (2009). 200 cells were scored for each sample and percent staining of nuclear beta-catenin was determined by normalizing positive nuclear staining to the total number of cells scored.
Figure 29:
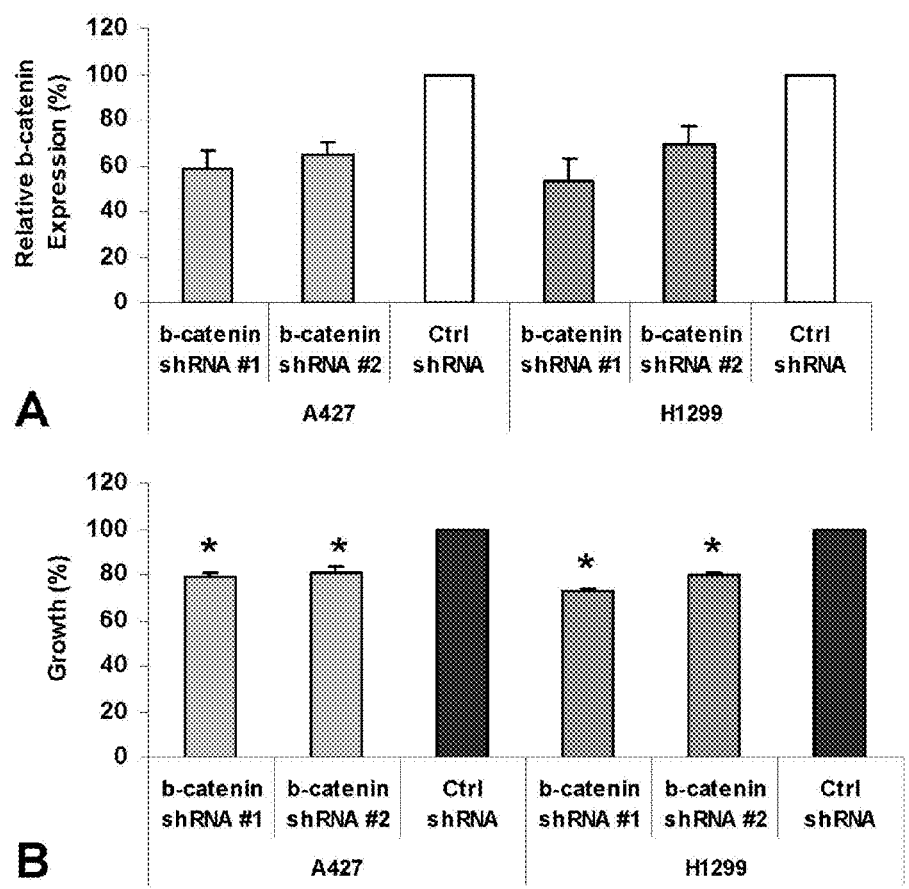
FIG. 29. Knock-down of β-catenin by shRNA suppresses growth of human lung cancer cell lines H1299 and A427. A) Quantitative RT-PCR of β-catenin gene GAPDH served as RNA control and normalization. B) Cell proliferation assay. (*) indicates statistical significance (p<0.05). H1299 and A427 cells were transfected with two different β-catenin shRNA and non-silencing shRNA control. Then RNA was isolated 3 days after transfection and MTS assay was performed 4 days after transfection. Controls in each experiment were set as 100%; Two β-catenin shRNAs (in pRFP-C-RS vector) were purchased from Origene. The targeted β-catenin gene sequences are: 5'-GGTCCTCTGTGAACTTGCTCAGGACAAGG-3' (SEQ ID NO:25); and 5'-GGCTGGTATCTCAGAAAGTGCCTGACACA-3' (SEQ ID NO:26).

To investigate the association of EMX2 expression with the status of WNT activation in lung cancer, we first examined the WNT family genes by real-time RT-PCR (data not shown) and nuclear β-catenin by immunofluorescent (IF) staining in cell lines and tissue samples (Table 1 and FIG. 28). Most samples were found to have up-regulation of at least one WNT family gene with increased amount of nuclear β-catenin, suggesting a possible association of reduced EMX2 expression and canonical WNT activation in lung cancer. EMX2 was then transfected into H1299 and H322 cells lacking EMX2 expression, and anti-EMX2 shRNAs was used in EMX2-expressing A427 cells. We used real-time RT-PCR to confirm EXM2 expression levels after stable transfectants were established. Levels of forced EMX2 expression in H1299 and H322 cells were compatible to that in H1703 (FIG. 24A) and endogenous EMX2 was significantly reduced (FIGS. 24A and 27A). We observed that re-expression of EMX2 led to a suppression of WNT1, WNT2, WNT3, WNT3A, and WNT5A transcripts as well as decreased levels of the canonical WNT downstream proteins β-catenin and Cyclin D1 (FIG. 24B). In contrast, shRNA silencing of EMX2 in A427 resulted in upregulation of those WNT genes and the canonical WNT downstream proteins β-catenin and its target Cyclin D1 (FIG. 24B). TOP/FOP experiments in these cell lines corroborated the interaction between EMX2 and activation of the canonical WNT pathway (FIGS. 24C and 27B) which appeared to be required for proliferation of these lung cancer cells (FIG. 29). To address how EMX2 regulates critical components of WNT signaling, we analyzed the promoter regions of the WNT family genes and confirmed the presence of putative EMX2 binding sites in several of them such as WNT1, WNT2, WNT3, WNT3A, and WNT5A, suggesting that EMX2 may function as a transcriptional repressor of those WNT genes in human lung cancer (FIG. 24D). We also examined activity of these WNT promoters (FIG. 24D) and found that overexpressing EMX2 significantly down-regulated activity of the WNT2 promoter but not the WNT1, WNT3, WNT3A, and WNT5A promoters, suggesting that transcription of these WNT genes may be directly or indirectly regulated by EMX2.

Figure 25:
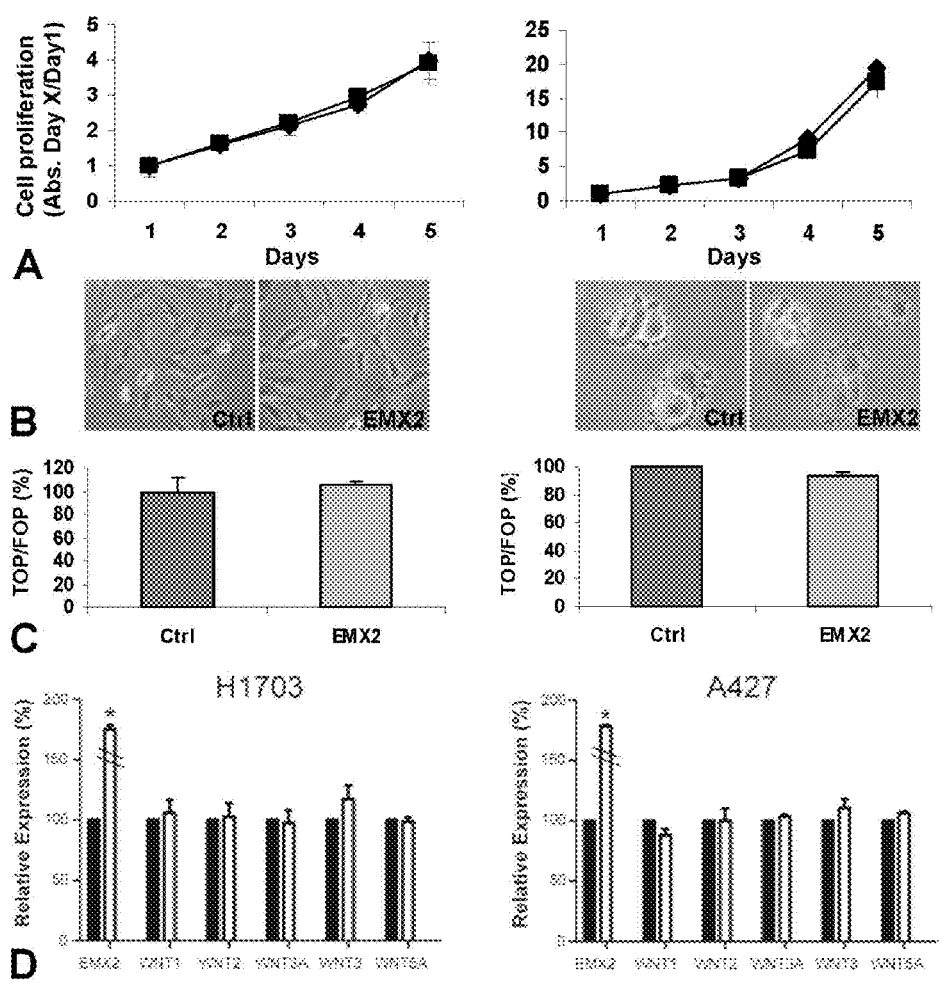
FIG. 25. Restoration of EMX2 did not affect cells expressing endogenous EMX2. (A) MTS result in H1703 and A427 cells stably transfected with EMX2 (solid squares) and empty vector (solid diamonds). The data shown is the mean of triplicate with error bars (S.D.). (B) Morphology of the H1703 and A427 cells stably transfected with EMX2 under light microscope (40×). (C) TOP/FOP assay of the canonical WNT pathway transcription activity in H1703 and A427 cells stably transfected with EMX2. (D) Quantitative RT-PCR expression analyses of EMX2 and WNT family genes in H1703 and A427 cells stably transfected with EMX2.

Finally, as a control, EMX2-expressing H1703 and A427 cells were stably transfected with EMX2 cDNA. We found that EMX2 restoration did not significantly affect cell proliferation, morphology (FIGS. 25A and 25B), or the canonical WNT signaling measured by TOP/FOP assay (FIG. 25C). Consistently, no noticeable changes in mRNA levels of WNT genes were observed in these transfected cells (FIG. 25D). WNT expression in the presence of EMX2 expression found in H1703 and A427 cells suggests that other mechanisms may be responsible for their transcriptional regulation.

Discussion

Abnormal WNT activation occurs in adulthood, and may play a decisive and pivotal role in the context of lung cancer. There has been no clear evidence of mutation or amplification of the WNT genes documented in human cancers, including lung cancer (Karim R et al., *Pathology* 36:120-8 (2004)), suggesting that other mechanisms may be involved in regulation of the WNT gene transcription in tumorigenesis. In the present study, we investigated the role of EMX2 in lung cancer and whether its expression is associated with the transcription of the WNT genes, and in turn, regulates the aberrant WNT activation in lung cancer. We observed a significant decrease in EMX2 expression in primary lung cancer tissue samples when compared to their adjacent normal tissues as well as in lung cancer cell lines. This EMX2 down-regulation was found to be significantly associated with hypermethylation of CpG islands in the EMX2 promoter region, indicating that epigenetic modification may be one of the important mechanisms to silence EMX2 gene in lung cancer. Interestingly, methylation silencing was recently reported for several other homeobox gene family members in cancer. For example, HOXA5 was identified as a direct transcription activator of tumor suppressor p53 and HOXA5 silencing by hypermethylation consequently limits p53 expression in breast cancer (Raman V et al., *J Biol Chem* 275:26551-5 (2000)). The HOXA9 promoter was found to be frequently methylated in non-seminomatous TGCT (Lind G E et al., *J Pathol* 210:441-9 (2006)). Our data also revealed that in a few cases, promoter hypermethylation of EMX2 did not correlate with decreased EMX2 expression, suggesting that alternative mechanisms may account for EMX2 down-regulation. Indeed, a report showed that EMX2 transcripts were reduced in a subset of endometrial cancers investigated with a 35% incidence of LOH for the 10q25.3-q26.1 region that includes the EMX2 gene. Sequencing analysis uncovered multiple EMX2 variants, including somatic mutations, intronic polymorphisms, and polymorphisms in the 3'-UTR (Noonan F C et al., *Genomics* 76:37-44 (2001)).

The down-regulation of EMX2 in lung cancer also suggests that EMX2 may function as a transcriptional repressor in a similar manner in lung cancer as it does during embryonic development. To test this hypothesis, we forced EMX2 expression in lung cancer cell lines lacking endogenous EMX2 expression and observed significant transcriptional suppression of several oncogenic WNT genes. Consistently, the WNT signaling dependent transcription activity as well as expression of the WNT downstream effectors and target genes were inhibited in these cells. In conjunction with WNT suppression, over-expressing EMX2 also inhibited cell proliferation, suggesting that EMX2 may inhibit lung cancer growth through regulation of WNT transcription and WNT signaling activity. Furthermore, our shRNA knock-down experiments in lung cancer cells expressing endogenous EMX2 confirmed our observations and supported our conclusions. However, given that the positions of putative EMX2 binding sites in promoter regions of the WNT family genes are distinct and that EMX2 fails to significantly down-regulate activities of several WNT promoters that we examined, with the exception of the WNT2 promoter, our interpretation is that EMX2 may regulate transcription of the oncogenic WNT genes either directly or indirectly. Other co-factors may also play important roles in EMX2-related transcription regulation. The identification of direct target(s) of EMX2 and its interacting proteins is needed to further elucidate the function of EMX2 and its relationship with activation of WNT signaling in lung cancer. Interestingly, both oncogenic and tumor-suppressing roles of WNT5A have been reported in various cancer types (McDonald SL and Silver A., *British J Cancer* 101:209-14 (2009)). In lung cancer, however, WNT5A was found to be upregulated in tumor tissues compared to normal lung tissues and over-expression of WNT5A was associated with more aggressive lung cancer (Huang C L et al., *J Clin Oncol* 23:8765-73 (2005)). Our observation that EMX2 regulates WNT5A expression appears to be consistent with the possible oncogenic role of WNT5A in lung cancer previously reported by Huang C L, et al. (Huang C L et al., *J Clin Oncol* 23:8765-73 (2005)).

Figure 30:
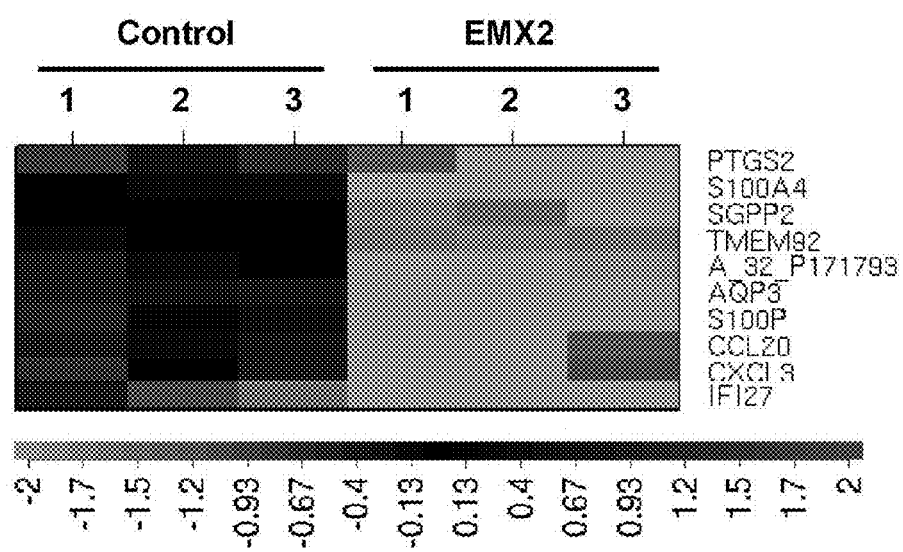
FIG. 30. Microarray profiling of lung cancer cell line H322 stably transfected with EMX2 and empty vector control. Partial heatmap plot of hierarchical clustering including S100A4 and S100P is shown. Sample preparation, labeling, and array hybridizations were performed according to standard protocols from the UCSF Shared Microarray Core Facilities and Agilent Technologies (www.arrays.ucsf.edu and www.agilent.com). Total RNA quality was assessed using a Pico Chip on an Agilent 2100 Bioanalyzer (Agilent Technologies, Palo Alto, Calif.). RNA was amplified and labeled with Cy3-CTP or Cy5-CTP using the Agilent low RNA input fluorescent linear amplification kits following the manufacturers protocol (Agilent). Labeled cRNA was assessed using the Nandrop ND-100 (Nanodrop Technologies, Wilmington Del.), and equal amounts of Cy3 and Cy5 labeled target were hybridized to Agilent whole human genome 44K Ink-jet arrays (Agilent). Hybridization samples were randomized on the 3×44K format to correct any batch bias. Hybridizations were performed for 14 hrs, according to the manufacturer's protocol. Arrays were scanned using the Agilent microarray scanner and raw signal intensities were extracted with Feature Extraction v9.5 software (Agilent).

In addition, we found that EMX2 inhibited invasive phenotypes of lung cancer, suggesting EMX2 may play an important role in lung cancer invasion and/or metastasis. In support, our preliminary microarray analysis revealed that EMX2 over-expression down-regulated metastasis genes such as S100P and S100A4, members of the EF-hand calcium-binding protein family (FIG. 30). These proteins have been reported to induce metastasis in rodent mammary model systems for breast cancer and to be associated with poor patient outcomes in breast, colon, lung cancer, and esophageal carcinoma (Donato R., *Int J Biochem Cell Biol* 33:637-68 (2001); Heizmann C W et al., *Front Biosci* 7:d1356-68 (2002); Zimmer D B et al., *Microsc Res Tech* 60:552-9 (2003); Marenholz I et al., *Biochem Biophys Res Commun* 322:1111-22 (2004)). It is possible that in lung cancer EMX2 regulates transcription of these metastasis genes directly or indirectly by down-regulating canonical WNT signaling; this is supported by recent evidence that S100P and 5100A4 may be direct downstream targets of WNT signaling (Stein U et al., *Gastroenterology* 131:1486-500 (2006); Ganesan K et al., *Cancer Res* 68:4277-86 (2008)).

In conclusion, this is the first demonstration of the importance of EMX2 as a transcription factor regulating the control of cellular proliferation in lung carcinogenesis, by itself and by suppressing the transcription of oncogenic WNT genes. We also demonstrate that epigenetic events affecting EMX2 lead to its silencing, loss of function and consequent cancer cell proliferation and metastasis. Epigenetic silencing of EMX2 expression may be important for over-expression of oncogenic WNTs, accounting for the aberrant activation of the WNT pathway in lung cancer.

TABLE 1

Canonical WNT Signaling Analyses in Human Lung Cancer

| | | Wnt Gene Upregulation | Nuclear β-catenin |
|---|---|---|---|
| Tissues | Case # | | |
| | 1 | Wnt2, Wnt3 | +++ |
| | 2 | Wn1, Wnt3, Wnt5a | ++ |
| | 3 | Wnt2 | + |
| | 4 | Wnt2, Wnt3 | + |
| | 5 | Wnt1, Wnt3 | + |
| | 6 | Wnt1, Wnt2 | ++ |
| | 7 | Wnt1 | + |
| | 8 | Wnt2, Wnt3 | ++ |
| | 9 | Wnt2, Wnt3a | + |
| | 10 | Wn1, Wnt3, Wnt3a, Wnt5a | + |
| Cell Lines | H460 | Wnt1, Wnt3, Wnt3a, Wnt5a | ++ |
| | A549 | Wnt2, Wnt3, Wnt5a | + |
| | H1703 | Wnt1 | − |
| | H838 | Wnt1 | + |
| | H1975 | Wnt1, Wnt3a | + |
| | A427 | Wnt2, Wnt3, Wnt3a | +/− |
| | H2170 | ND | + |
| | H1666 | Wnt1, Wnt5a | + |
| | H1299 | Wnt1, Wnt2, Wnt3a | ++ |
| | H322 | Wnt3a, Wnt5a | + |
| | H441 | Wnt1, Wnt2 | + |

Note:
ND, not deteremined

Example 18

Downregulation of EMX2 is Associated with Clinical Outcomes in Lung Adenocarcinoma Patients Purpose EMX2, a human homologue of the *Drosophila* empty spiracles gene, is a homeodomain-containing functional transcription factor. However, little is known about the role of EMX2 in tumorigenesis. This study assessed the expression of EMX2 in lung adenocarcinoma and correlated it with patient prognosis and clinical outcomes.

Patients and Methods

One hundred forty-four patients with lung adenocarcinoma undergoing surgery were studied. Quantitative real-time reverse transcriptase polymerase chain reaction (RT-PCR) was used to analyze EMX2 mRNA expression. Association of EMX2 levels with clinical outcomes was evaluated with the R package software.

Results

EMX2 mRNA expression was significantly downregulated in lung adenocarcinoma compared to their adjacent normal tissues (p<0.001). EMX2 expression level correlated with overall survival (OS) and recurrence free survival (RFS) in patients, shown by Kaplan-Meier analysis. The EMX2-high expressing group had statistically significant better OS than the EMX2-low expressing group among all adenocarcinoma patients analyzed (p=0.005), stage I patients (p=0.01), or patients with features of bronchioloalveolar carcinoma (BAC) (p=0.03). The EMX2-high expressing group also had statistically significant better RFS than the EMX2-low expression group in adenocarcinoma patients (p<0.001).

Conclusion

Downregulation of EMX2 is associated with a poorer outcome in lung adenocarcinoma patients and it may have a clinical role as an important prognostic marker.

Introduction

Lung cancer is the most common cancer in the world and the leading cause of cancer-related death. (Parkin, D M, *Lancet Oncol;* 2:533-43 (2000)) NSCLC constitutes around 80% of all lung cancers (predominant histology is adenocarcinoma). (Gridelli C, et al., *J Clin Oncol;* 25:1898-907 (2007)) Overall NSCLC survival is 15% in the U.S., lower in developing countries and 35-50% of early stage I NSCLC patients relapse within 5 years. (Jemal A, et al., *CA Cancer Clin;* 57:43-66 (2007); Guo L., et al., *Clin Cancer Res;* 12:3344-54 (2006)) The molecular carcinogenesis of lung cancer is characterized by multiple alterations of gene expression and function. These arise from a series of molecular and morphological events affecting oncogenes such as K-ras and EGFR and tumor suppressor genes such as p53 and p16. Despite efforts by various methods, meaningful prognostic biomarkers remain to be optimized and evaluated through clinical trials. (Chen, H Y, et al., *N Engl J Med;* 356:11-20 (2007))

The homeobox gene family encodes transcription factors, regulating morphogenesis and cell differentiation during embryogenesis by activating or repressing the expression of target genes (Saad, R S, et al., *Mod Pathol;* 17:1235-42 (2004)). In addition, several homeobox genes have recently been shown to be associated with cancers (Kitamura, H, et al., *Am J Clin Pathol;* 111:610-22 (1999); Okubo, K, et al., *J Thorac Cardiovasc Surg;* 118:702-9 (1999); Noguchi, M, et al., *Cancer;* 75:2844-52 (1995); Raz, D J, et al., *Curr Opin Pulm Med;* 13:290-6 (2007)). EMX2, a human homologue of the *Drosophila* empty spiracles gene (ems) is a homeodomain-containing transcription factor with important functions during early development. For example, mice harboring homozygous EMX2 mutation exhibit small olfactory bulbs and cerebral hemispheres. (Dalton, D, et al., *Genes Dev;* 3:1940-56 (1989)) EMX2 affects adult neural stem cell proliferation controlling the frequency of symmetric divisions and over-expressing EMX2 decreases division frequency. (Galli, R, et al., *Development;* 129:1633-44 (2002)) EMX2 controls mammalian reproduction via endometrial cell proliferation without effecting differentiation. (Taylor, H S, et al., *Mol Endocrinol;* 19:2839-46 (2005)) Moreover, it has been reported that loss of EMX2 leads to ectopic Wnt-1 expression in the developing mammalian telecephalon resulting in cortical dysplasia. (Ligon, K L, et al., *Development;* 130:2275-87 (2003)) A limited number of recent studies suggest possible involvement of EMX2 in human cancers. For example, EMX2 may be anti-proliferative in the endometrium and its expression is decreased in endometrial tumors. EMX2 was also reported being rarely methylated in non-seminomas. However, the role of EMX2 in tumorigenesis is still largely unknown. Because of the functional linkage between EMX2 and regulation of the Wnt gene expression, and critical roles that Wnt signaling plays in oncogenesis including lung cancer (Chen, H Y, et al., *N Engl J Med;* 356:11-20, 9-12 (2007); Ligon K L, et al., *Development;* 130:2275-87 (2003); Therneau, TaA, E., An introduction to recursive partitioning using the rpart routines, Technical report, Mayo Foundation (1997);

Jemal, A, et al., *CA Cancer J Clin;* 58:71-96 (2008); Yoshida Y, et al., *Lung Cancer;* 50:1-8 (2005)), we hypothesize that EMX2 may be functional important during lung cancer progression. Therefore, in this study we investigated the EMX2 expression and its clinical significance in lung cancer patients.

Patients and Methods

Patients: 144 patients with lung adenocarcinoma undergoing surgery at the University of California, San Francisco (UCSF) from July 1999 to August 2006 were studied. TNM staging was made according to the World Health Organization pathologic classification system. Pathological lymph node status was evaluated from resected specimens. The 144 patients included 81 adenocarcinoma without features of BAC, and 63 with features of BAC (Table 2). Patients who received pre-operative chemotherapy were excluded from the study, so as not to confound development of a purely prognostic tool. In addition to histopathology, patients' clinical follow-up was documented (median follow-up for all patients was 42.8±2.1 months extending to May 10, 2007). The primary endpoint was OS. RFS was defined as the time from surgery until radiographic evidence of recurrent disease or time until the last documented physician follow-up visit in the absence of recurrent disease. Patients consented to tissue specimen collection prospectively, and the study was approved by the Committee on Human Research at UCSF.

Tissue RNA Extraction and Quantitative Real-Time RT-PCR: Fresh samples were collected from patients undergoing surgical resection and were promptly snap-frozen in liquid nitrogen and stored at −170° C. before use. Total RNA was extracted using the TRlzol LS method (Invitrogen, Carlsbad, Calif.). cDNA synthesis and quantitative Taqman PCR were performed as previously described. Hybridization probes and primers for EMX2 and housekeeping gene GAPDH were purchased from Applied Biosystems (ABI, Foster City, Calif.). The EMX2 mRNA expression was assayed in triplicate in ABI 7300 Real-time PCR System. Samples were normalized to their internal control GAPDH and then calculated using $2^{-ddCT}$ method, compared to that of total RNA from adult normal lung tissue (BioChain, Hayward, Calif.).

Statistical Analysis: The Kaplan-Meier method was used to estimate overall survival and recurrence-free survival. Differences in survival between the low-risk group (high EMX2 expression) and high-risk group (low EMX2 expression) were analyzed by log-rank test. Multivariate Cox proportional hazards regression analysis was used to assess the effect of EMX2 expression on survival. Hazard ratios (HR) and 95% confidence interval (CI) were calculated from Cox regression model. The associations between gene expression and discrete clinical categories were analyzed by the t-test, ANOVA with Bonferrini/Dunn test, Mann-Whitney's U-test for variables with two-categories, and the Kruskal-Wallis test for variables with more than two categories. All reported p-values were two-sided. A p value of 0.05 or less was considered to be significant.

Results

EMX2 Expression is Down-regulated in Lung Adenocarcinoma

Figure 31:
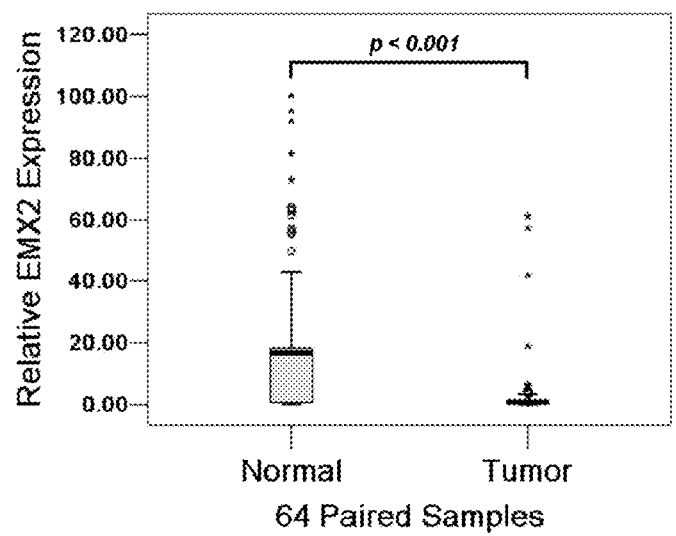
FIG. 31. EMX2 expression is down-regulated in lung adenocarcinoma. Quantitative RT-PCR result of 64 tumors and their matched normal lungs was shown. 25th and 75th percentiles are as box margins, 10th and 90th percentiles are as error bars, and the median is as a line in the box. Outlying data are as dots.

We first examined the mRNA levels of EMX2 in human lung cancer tissues samples and their matched adjacent normal tissues obtained from 64 patients with lung adenocarcinoma. Upon comparison 71.8% (46 of 64) lung cancer samples analyzed were found to have less EMX2 expression that their matched adjacent normal tissues (FIG. 31) and this down-regulation was statistically significant (mean values of EMX2 expression measured by quantitative RT-PCR were 3.78 and 18.01 in cancer tissues and their matched adjacent normal tissues, respectively; p<0.001).

EMX2 Expression is Associated with Improved Survival in Lung Adenocarcinoma

Figure 32:
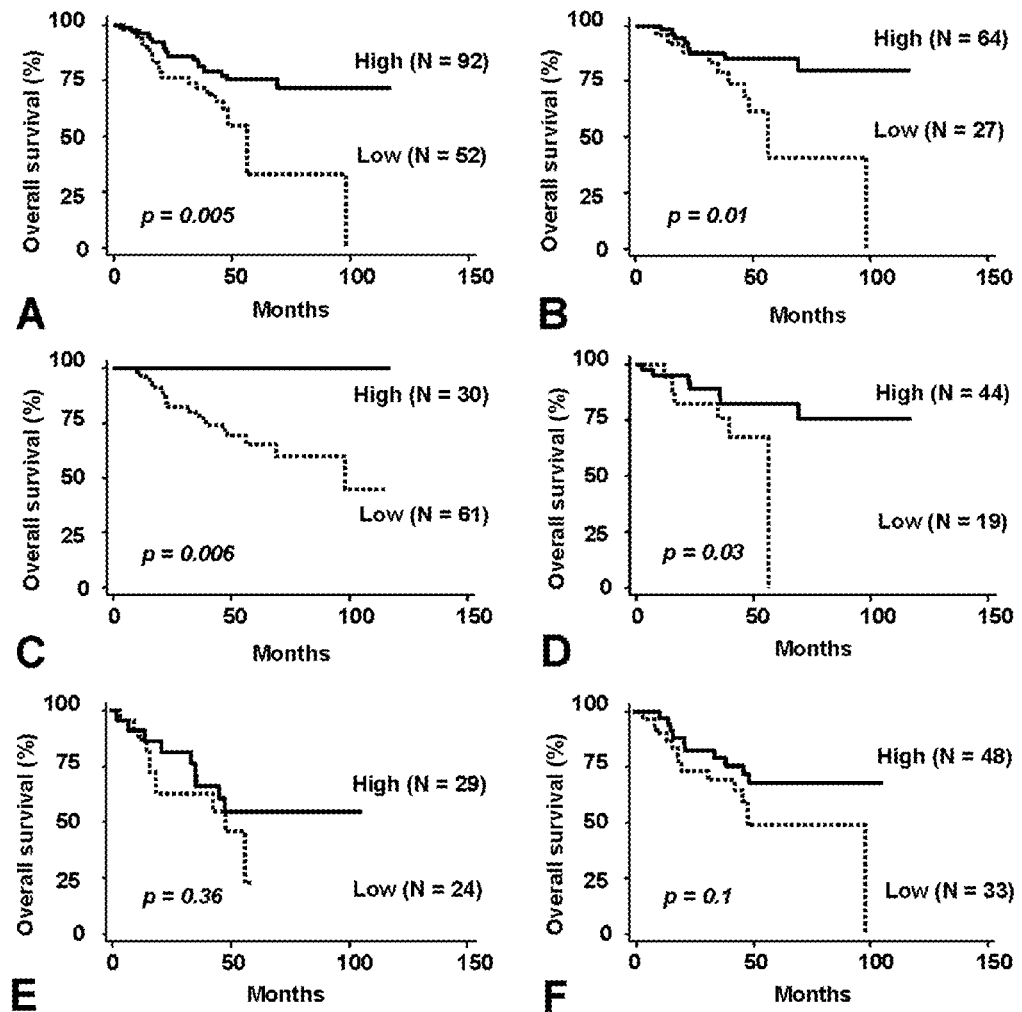
FIGS. 32A-F. Kaplan-Meier estimates of overall survival according to EMX2 expression level using quantitative RT-PCR. (A) Overall survival in 144 adenocarcinoma patients with or without BAC feature; (B) and (C) Overall survival in 91 stage I patients: using 1.29 and 6.77 as cut-off point, respectively; (D) Overall survival in 63 adenocarcinoma patients with BAC feature; (E) Overall survival in 40 stage II to IV patients; (F) Overall survival in 81 adenocarcinoma patients without BAC feature.
Figure 33:
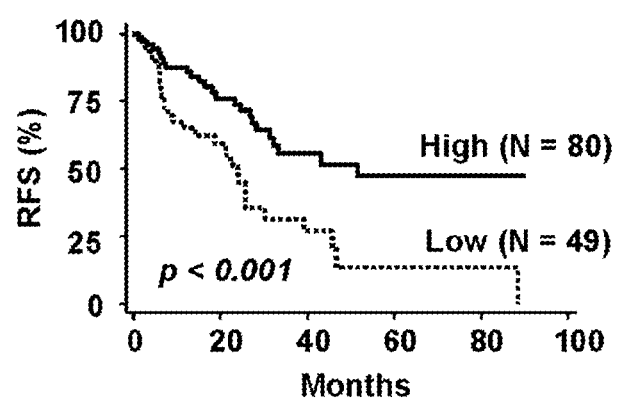
FIG. 33. Kaplan-Meier estimates of recurrence-free survival according to EMX2 expression level using quantitative RT-PCR in 129 adenocarcinoma patients with or without BAC feature.

To compare EMX2 expression levels among patients, optimal cut-off points for partitioning into high/low risk survival subgroups, based on threshold EMX2 expression at the cut-point, were determined using survival trees. Assessment of the predictive reproducibility of the partition made recourse to cross-validation. (Therneau TaA, E., An introduction to recursive partitioning using the rpart routines, Technical report, Mayo Foundation (1997)) We found that EMX2 was associated with survival (p=0.003), recurrence (p=0.007), and gender (p=0.04). There was no significant association between EMX2 expression and tumor stage, age, smoking status, histology, surgical procedure, and ECOG PS. Overall survival was significantly better in patients in the EMX2-high expressing group compared to those in the EMX2-low expressing group in all patients (p=0.005; the median survival: high (not reached) vs. low (60 months)) (FIG. 32A), stage I patients using optimal cut-off point 1: 1.29 (p=0.01; not reached vs. 56 months) (FIG. 32B) or optimal cut-off point 2: 6.77 (p=0.006; not reached vs. 98 months) (FIG. 32C), and in adenocarcinoma patients with BAC features (p=0.03; not reached vs. 56 months) (FIG. 32D). On the other hand, no difference in survival was observed in patients with stages 11 to IV (p=0.36) (FIG. 32E), and in adenocarcinoma patients without BAC features (p=0.13) (FIG. 32F). Furthermore, there was statistical significance in recurrence-free survival for all patients: The median recurrence-free survival in EMX2-low expressing group was 24 months, compared to 52 months for the EMX2-high expressing group (p<0.001) (FIG. 33). According to Cox multivariate regression analysis, consistent EMX2 expression level was significantly associated with overall survival (Hazard ratio 0.44, Cl 0.23-0.85, p=0.02) (Table 3).

Discussion

Despite therapeutic advances, NSCLC remains the main cause of cancer deaths worldwide. (Jemal, A, et al., *CA Cancer J Clin;* 58:71-96 (2008)) NSCLC occurs through multi-step oncogenesis: atypical adenomatous hyperplasia (AAH), a pre-malignant lesion of bronchioloalveolar carcinoma (BAC), a type of adenocarcinoma, is often adjacent to invasive cancer. (Yoshida, Y, et al., *Lung Cancer;* 50:1-8 (2005); Saad, R S, et al., *Mod Pathol;* 17:1235-42 (2004); Kitamura, H, et al., *Am J Clin Pathol;* 111:610-22 (1999); Okubo K, et al., *J Thorac Cardiovasc Surg;* 118:702-9 (1999)) BAC with its characteristic histology lacking fibroblastic proliferation, seen as pure ground glass opacities (GGO) on contrast enhanced high resolution CT, shows less chances of nodal metastasis and improved prognosis. (Noguchi, M, et al., *Cancer;* 75:2844-52 (1995)) Five-year survival for stage I NSCLC and BAC is 60-80%. (Raz, D J, et al., *Curr Opin Pulm Med;* 13:290-6 (2007)). Abnormal genetic differences affecting signaling pathways cause the heterogeneity of NSCLC. Tumor suppressor genes and oncogenes play a major role in the development of NSCLC through delicate balances regulating cell proliferation according to tumor type and stage. (Bishop, J M, *Cell;* 64:235-48 (1991); Weinberg, R A, *Science;* 254:1138-46 (1991)) There is evidence that stage I NSCLC patients display different genetic characteristics to those with progressive disease but unanswered questions regarding tumor biology prevail. (Yu, Y, et al., *Nat Med;* 10:175-81 (2004)) This creates controversy about standards of care, exemplified in early stage NSCLC where the standard of care is lobectomy with systematic Imphadenectomy. (Adam Yagui-Beltran, D M J, *Expert Review of Respiratory*

*Medicine*; Vol. 1:343-53 (2007)) The adequacy of these therapeutic practices is increasingly questioned as knowledge of lung tumor biology improves resulting in effective staging tools and tumor molecular profiling. Consequently, and in an effort to further dissect and understand the mechanisms underlying NSCLC we have examined the correlation between EMX2 expression and clinical outcome in lung adenocarcinoma. We show that EMX2 expression strongly correlates with disease recurrence. Furthermore, survival rates were found to be significantly different in stage I NSCLC, adenocarcinoma, and BAC patients according to EMX2 expression through Kaplan-Meier analysis. Multivariate Cox proportional hazards analysis showed that EMX2 is a good prognostic factor for lung cancer and independently linked to mortality. This is important in early stage patients and in those with BAC histology where high expression of EMX2 correlates with better prognosis. In late stage NSCLC (stages II to IV) and in adenocarcinoma without BAC features high-EMX2 expression correlated with better recurrence-free survival rates compared to patients with low EMX2 expression; but this was not statistically significant.

In conclusion, we demonstrate for the first time, the importance of EMX2 as a transcription factor regulating the control of cellular proliferation in the context of lung carcinogenesis, by itself and by suppressing the transcription of oncogenic Wnts. We demonstrate that epigenetic events affecting EMX2 lead to its silencing, loss of function and consequent cancer cell proliferation, eventual metastasis and decreased patient disease-free survival. EMX2, upon further validation may serve as a potential prognostic marker in early stage lung adenocarcinoma.

TABLE 2

EMX2 Expression and Clinical Characteristics in Lung Adenocarcinoma Patients

| Characteristics | Adenocarcinoma and **BAC (N = 144) | | |
|---|---|---|---|
| | Number (%) | EMX2 Expression | p-value |
| Age | | | |
| Median | 67.6 ± 0.9 (years) | | |
| Range | 41-91 (years) | | |
| Whole | 144 (100%) | 21.36 ± 4.68 | N.S. |
| Young (<50) | 9 (6.2%) | 8.36 ± 6.13 | |
| Middle (50<, 75<) | 98 (68.1%) | 20.79 ± 5.66 | |
| Old (75>) | 37 (25.7%) | 26.04 ± 10.29 | |
| Sex | | | |
| Male | 54 (37.5%) | 15.34 ± 5.91 | |
| Female | 90 (62.5%) | 24.97 ± 6.58 | p = 0.04 |
| Race | | | |
| Caucasian | 110 (76.4%) | 20.39 ± 5.43 | |
| Asian | 22 (15.3%) | 20.42 ± 10.50 | |
| Others | 11 (7.6%) | 31.04 ± 20.21 | |
| Unknown | 1 (0.7%) | 42.63 | N.S. |
| Smoking | | | |
| Never | 33 (22.9%) | 19.54 ± 8.20 | |
| Smoker | 107 (74.3%) | 21.27 ± 5.73 | |
| Past | 68 (47.2%) | 24.56 ± 8.22 | |
| Current | 39 (27.1%) | 15.55 ± 6.50 | |
| Unknown | 4 (2.8%) | 38.62 ± 21.72 | N.S. |
| Pack per year | | | |
| Median | 34.4 ± 3.0 | | |
| Range | 0-160 | | |
| Sex, Smoking | | | |
| Male, Smoker | 46 (31.9%) | 17.11 ± 6.91 | |
| Male, Non-Smoker | 8 (5.6%) | 5.18 ± 2.66 | |
| Female, Smoker | 61 (42.4%) | 24.41 ± 8.63 | |
| Female, Non-Smoker | 25 (17.3%) | 24.14 ± 10.68 | |
| Unknown | 4 (2.8%) | 38.62 ± 21.72 | N.S. |
| Tumor size | | | |
| Median | 3.5 ± 0.2 (cm) | | |
| Range | 0.8 ± 13.0 (cm) | | |
| 3 cm or less | 76 (52.8%) | 28.74 ± 8.02 | |
| over 3 cm | 67 (46.5%) | 13.24 ± 4.11 | |
| Unknown | 1 (0.7%) | 3.79 | N.S. |
| Pathological Stage | | | |
| Stage I | 91 (63.2%) | 18.55 ± 4.29 | |
| Stage II | 17 (11.8%) | 16.09 ± 11.19 | |

TABLE 2-continued

EMX2 Expression and Clinical Characteristics in Lung Adenocarcinoma Patients

| Characteristics | Number (%) | EMX2 Expression | p-value |
|---|---|---|---|
| Stage III | 25 (17.4%) | 15.70 ± 8.57 | |
| Stage IV | 10 (6.9%) | 72.00 ± 46.35 | |
| Unknown | 1 (0.7%) | 1.52 | N.S. |
| Histology | | | |
| Adenocarcinoma | 81 (56.3%) | 26.03 ± 7.56 | |
| **BAC | 63 (43.7%) | 15.35 ± 4.42 | |
| Mixed BAC | 42 (29.1%) | 18.24 ± 6.34 | |
| Pure BAC | 21 (14.6%) | 9.57 ± 3.83 | N.S. |
| *ECOG PS | | | |
| 0 | 76 (52.8%) | 19.31 ± 4.90 | |
| 1 | 29 (20.1%) | 11.18 ± 6.53 | |
| 2 | 6 (4.2%) | 1.73 ± 0.70 | |
| Unknown | 33 (22.9%) | 38.60 ± 15.80 | N.S. |
| Operation Procedure | | | |
| Wedge Resection | 13 (9.0%) | 44.31 ± 33.91 | |
| Segmentectomy | 5 (3.5%) | 15.17 ± 10.23 | |
| Lobectomy | 113 (78.5%) | 19.74 ± 4.43 | |
| Biobectomy | 7 (4.9%) | 17.45 ± 14.72 | |
| Pnumonectomy | 6 (4.1%) | 11.83 ± 11.07 | N.S. |
| Chemotherapy | | | |
| Yes | 69 (47.9%) | 22.87 ± 6.02 | |
| No | 74 (51.4%) | 20.21 ± 7.20 | |
| N/A | 1 (0.7%) | 215 | N.S. |
| Vital Status | | | |
| Alive | 91 (63.2%) | 30.51 ± 7.16 | |
| Dead | 53 (36.8%) | 5.64 ± 1.91 | p = 0.003 |
| Recurrence | | | |
| Positive | 55 (38.2%) | 6.48 ± 2.11 | |
| Negative | 74 (51.4%) | 22.75 ± 5.46 | p + 0.007 |
| Follow up, months | | | |
| Median | 41.6 ± 2.3 (months) | | |
| Range | 0.3-117.3 (months) | | |

*Eastern Cooperative Oncology Group performance status
**Bronchioloalveolar carcinoma

TABLE 3

Cox-multivariate Model in Lung Adenocarcinoma and BAC Patients

| Variable | Hazard Ratio | (95% Cl*) | p-value |
|---|---|---|---|
| EMX2 Expression | | | |
| High Expression Group | 0.44 | 0.23-0.85 | 0.02 |
| Pathological stage (compared to Stage I) | 0.81 | 0.71-1.04 | 0.03 |
| Stage II | 1.36 | 0.50-3.72 | 0.55 |
| Stage III | 2.47 | 1.13-5.41 | 0.02 |
| Stage IV | 3 88 | 1.41-10.69 | 0.009 |
| Histology | | | |
| BAC (compared to Adenocarcinoma | 0.60 | 0.80-4.90 | 0.12 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

All patents, patent applications, and other publications, including GenBank Accession Numbers, cited in this application are incorporated by reference in the entirety for all purposes.

LITERATURE

Noonan et al., "Characterization of the Homeodomain Gene EMX2 Sequence Conservation, Expression Analysis and a Search for Mutations in Endometrial Cancer." *Genomics* 76:37-44 (2001).

Lind et al., "Novel Epigenetically Deregulated Genes in Testicular Cancer Include Homeobox Genes and SCGB3A1 (HIN-1)." *J. Pathol.* 210:4414-449 (2006).

Theil et al., "Wnt and Bmp Signalling Cooperatively Regulate Graded EMX2 expression in the Dorsal Telencephalon." *Development* 129(13):3045-54 (2002).

Raz et al., "Current concepts in bronchioloalveolar carcinoma biology." *Clin Cancer Res.* 12(12):3698-704 (2006).

Galm et al., "Methylation-Specific Polymerase Chain Reaction." *Methods Mol. Med.* 113:296-291 (2005).

U.S. Patent Publication No. 20040219575 (Neuman et al.)

| U.S. Patent Publication No. 20070065859 (Wang et al.) | U.S. Patent Publication No. 20040247593 |
| U.S. Patent Publication No. 20070026393 (Berlin et al.) | U.S. Patent Publication No. 20060040883 |

What is claimed is:

1. A method of predicting the likelihood of overall survival and recurrence-free survival for a patient having cancer, the method comprising:
   (a) assaying an expression level of an EMX2 RNA transcript in a biological sample comprising a cancer cell obtained from said patient, wherein the cancer is selected from the group consisting of lung, colon, and esophageal cancer, wherein said assaying comprises using a reverse transcription-PCR (RT-PCR) assay, wherein the RT-PCR assay comprises the use of a primer comprising the nucleotide sequence of SEQ ID NO: 3, and wherein the expression level of the EMX2 RNA transcript directly correlates with a likelihood of overall survival or recurrence-free survival of the patient; and
   (b) providing information comprising an estimate of the likelihood of overall survival or recurrence-free survival, wherein the estimate of a low likelihood of overall survival or recurrence-free survival is solely based on a decrease in the expression level of the EMX2 RNA transcript observed in the biological sample as compared to the expression level from a control sample from a subject that does not have cancer.

2. The method of claim 1, wherein step (a) is performed on the biological samples from two or more patients, and wherein step (b) further comprises providing an estimate of lower likelihood of survival when a larger decrease is observed in step (a).

3. The method of claim 1, wherein the cancer is a lung cancer.

4. The method of claim 3, wherein the lung cancer is non-small cell lung carcinoma, adenocarcinoma, or mesothelioma.

5. The method of claim 3, wherein the lung cancer is bronchioloalveolar carcinoma.

6. The method of claim 1, wherein said determining comprises determining a normalized expression level of the EMX2 RNA transcript.

7. The method of claim 1, wherein said expression level is determined by quantitative real-time PCR.

8. The method of claim 1, wherein said providing comprises generating a report comprising the information.

9. The method of claim 8, wherein said report comprises information regarding treatment options for cancers according to an expression level of an EMX2 RNA transcript.

10. The method of claim 1 wherein the RT-PCR assay further comprises the use of a primer comprising the nucleotide sequence of SEQ ID NO: 4.

11. A method of predicting the likelihood of overall survival and recurrence-free survival for a patient having cancer, the method comprising:
   (a) assaying an expression level of an EMX2 RNA transcript in a biological sample comprising a cancer cell obtained from said patient, wherein the cancer is selected from the group consisting of lung, colon, and esophageal cancer, wherein said assaying comprises using an EMX2 promoter methylation assay, wherein the promoter methylation assay is a methylation-specific polymerase chain reaction (MSP), wherein the MSP assay comprises the use of a primer comprising the nucleotide sequence of SEQ ID NO: 20, and wherein the expression level of the EMX2 RNA transcript directly correlates with a likelihood of overall survival or recurrence-free survival of the patient; and
   (b) providing information comprising an estimate of the likelihood of overall survival or recurrence-free survival, wherein the estimate of a low likelihood of overall survival or recurrence-free survival is solely based on a decrease in the expression level of the EMX2 RNA transcript observed in the biological sample as compared to the expression level from a control sample from a subject that does not have cancer.

12. The method of claim 11 wherein the MSP assay further comprises the use of a primer comprising the nucleotide sequence of SEQ ID NO: 21.

13. The method of claim 11, wherein step (a) is performed on the biological samples from two or more patients, and wherein step (b) further comprises providing an estimate of lower likelihood of survival when a larger decrease is observed in step (a).

14. The method of claim 11, wherein the cancer is a lung cancer.

15. The method of claim 14, wherein the lung cancer is non-small cell lung carcinoma, adenocarcinoma, or mesothelioma.

16. The method of claim 14, wherein the lung cancer is bronchioloalveolar carcinoma.

17. The method of claim 11, wherein said expression level is determined by quantitative MSP.

18. The method of claim 11, wherein said providing comprises generating a report comprising the information.

19. The method of claim 18, wherein said report comprises information regarding treatment options for cancers according to an expression level of an EMX2 RNA transcript.

20. A method for assaying the expression level of an EMX2 RNA transcript in a biological sample comprising:
    (a) providing a biological sample, wherein the biological sample comprises esophageal tissue or colon tissue;
    (b) employing an EMX2 promoter methylation assay, wherein the promoter methylation assay is methylation-specific polymerase chain reaction (MSP); and
    (c) using the result of step (b) for assaying the expression level of an EMX2 RNA transcript.

21. The method of claim 20 wherein the MSP assay comprises the use of a primer comprising the nucleotide sequence of SEQ ID NO: 20 or comprises the use of a primer comprising the nucleotide sequence of SEQ ID NO: 21.

22. The method of claim 21 wherein the MSP assay comprises the use of primers comprising the nucleotide sequences of SEQ ID NO: 20 and SEQ ID NO: 21.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: synthetic PT-PCR EXM2 forward primer

<400> SEQUENCE: 1
gatatctggg tcatcgcttc                                       20

<210> SEQ ID NO 2
<211> LENGTH: 20
<212> TYPE: DNA
<213> ORGANISM: Artificial Sequence
<220> FEATURE:
<223> OTHER INFORMATION: synthetic PT-PCR EXM2 reverse primer

<400> SEQUENCE: 2
tgagtttccg tgaggctgag                                       20

<210> SEQ ID NO 3
<211> LENGTH: 20
<212> TYPE: DNA
<213> ORGANISM: Artificial Sequence
<220> FEATURE:
<223> OTHER INFORMATION: synthetic PT-PCR EMX2 forward primer

<400> SEQUENCE: 3
gatatctggg tcatcgcttc                                       20

<210> SEQ ID NO 4
<211> LENGTH: 20
<212> TYPE: DNA
<213> ORGANISM: Artificial Sequence
<220> FEATURE:
<223> OTHER INFORMATION: synthetic PT-PCR EMX2 reverse primer

<400> SEQUENCE: 4
tgagtttccg tgaggctgag                                       20

<210> SEQ ID NO 5
<211> LENGTH: 20
<212> TYPE: DNA
<213> ORGANISM: Artificial Sequence
<220> FEATURE:
<223> OTHER INFORMATION: synthetic PT-PCR WNT1 forward primer

<400> SEQUENCE: 5
ctgcagcgac aacattgact                                       20

<210> SEQ ID NO 6
<211> LENGTH: 18
<212> TYPE: DNA
<213> ORGANISM: Artificial Sequence
<220> FEATURE:
<223> OTHER INFORMATION: synthetic PT-PCR WNT1 reverse primer

<400> SEQUENCE: 6
cgtggcactt gcactcct                                         18

```
<210> SEQ ID NO 7
<211> LENGTH: 25
<212> TYPE: DNA
<213> ORGANISM: Artificial Sequence
<220> FEATURE:
<223> OTHER INFORMATION: synthetic PT-PCR WNT2 forward primer

<400> SEQUENCE: 7
ggatgccaga gccctgatga atctt                                    25

<210> SEQ ID NO 8
<211> LENGTH: 24
<212> TYPE: DNA
<213> ORGANISM: Artificial Sequence
<220> FEATURE:
<223> OTHER INFORMATION: synthetic PT-PCR WNT2 reverse primer

<400> SEQUENCE: 8
gccagccagc atgtcctgag agta                                     24

<210> SEQ ID NO 9
<211> LENGTH: 23
<212> TYPE: DNA
<213> ORGANISM: Artificial Sequence
<220> FEATURE:
<223> OTHER INFORMATION: synthetic PT-PCR WNT3 forward primer

<400> SEQUENCE: 9
atcataaggg gccgcctggc gaa                                      23

<210> SEQ ID NO 10
<211> LENGTH: 20
<212> TYPE: DNA
<213> ORGANISM: Artificial Sequence
<220> FEATURE:
<223> OTHER INFORMATION: synthetic PT-PCR WNT3 reverse primer

<400> SEQUENCE: 10
atgagcgtgt cactgcaaag                                          20

<210> SEQ ID NO 11
<211> LENGTH: 20
<212> TYPE: DNA
<213> ORGANISM: Artificial Sequence
<220> FEATURE:
<223> OTHER INFORMATION: synthetic PT-PCR WNT3A forward primer

<400> SEQUENCE: 11
caagattggc atccaggagt                                          20

<210> SEQ ID NO 12
<211> LENGTH: 20
<212> TYPE: DNA
<213> ORGANISM: Artificial Sequence
<220> FEATURE:
<223> OTHER INFORMATION: synthetic PT-PCR WNT3A reverse primer

<400> SEQUENCE: 12
atgagcgtgt cactgcaaag                                          20

<210> SEQ ID NO 13
<211> LENGTH: 20
<212> TYPE: DNA
<213> ORGANISM: Artificial Sequence
<220> FEATURE:
<223> OTHER INFORMATION: synthetic PT-PCR WNT5A forward primer
```

<400> SEQUENCE: 13
agggcattac ttgttcgtta                                               20

<210> SEQ ID NO 14
<211> LENGTH: 20
<212> TYPE: DNA
<213> ORGANISM: Artificial Sequence
<220> FEATURE:
<223> OTHER INFORMATION: synthetic PT-PCR WNT5A reverse primer

<400> SEQUENCE: 14
gaacatattt gatggcctgt                                               20

<210> SEQ ID NO 15
<211> LENGTH: 20
<212> TYPE: DNA
<213> ORGANISM: Artificial Sequence
<220> FEATURE:
<223> OTHER INFORMATION: synthetic PT-PCR WNT16 forward primer

<400> SEQUENCE: 15
tgtccagtat ggcatgtggt                                               20

<210> SEQ ID NO 16
<211> LENGTH: 20
<212> TYPE: DNA
<213> ORGANISM: Artificial Sequence
<220> FEATURE:
<223> OTHER INFORMATION: synthetic PT-PCR WNT16 reverse primer

<400> SEQUENCE: 16
ttccagcatg ttttcacagc                                               20

<210> SEQ ID NO 17
<211> LENGTH: 25
<212> TYPE: DNA
<213> ORGANISM: Artificial Sequence
<220> FEATURE:
<223> OTHER INFORMATION: synthetic qMSP ATCB forward primer

<400> SEQUENCE: 17
tggtgatgga ggaggtttag taagt                                         25

<210> SEQ ID NO 18
<211> LENGTH: 27
<212> TYPE: DNA
<213> ORGANISM: Artificial Sequence
<220> FEATURE:
<223> OTHER INFORMATION: synthetic qMSP ATCB reverse primer

<400> SEQUENCE: 18
aaccaataaa acctactcct cccttaa                                       27

<210> SEQ ID NO 19
<211> LENGTH: 30
<212> TYPE: DNA
<213> ORGANISM: Artificial Sequence
<220> FEATURE:
<223> OTHER INFORMATION: synthetic qMSP ATCB probe
<221> NAME/KEY: modified_base
<222> LOCATION: (1)...(1)
<223> OTHER INFORMATION: a modified by 6-FAM

<400> SEQUENCE: 19
accaccaccc aacacacaat aacaaacaca                                    30

```
<210> SEQ ID NO 20
<211> LENGTH: 20
<212> TYPE: DNA
<213> ORGANISM: Artificial Sequence
<220> FEATURE:
<223> OTHER INFORMATION: synthetic qMSP EMX2 forward primer

<400> SEQUENCE: 20
attcggattt ggtgttcgtc                                              20

<210> SEQ ID NO 21
<211> LENGTH: 20
<212> TYPE: DNA
<213> ORGANISM: Artificial Sequence
<220> FEATURE:
<223> OTHER INFORMATION: synthetic qMSP EMX2 reverse primer

<400> SEQUENCE: 21
cgaatcccgc tactacgaaa                                              20

<210> SEQ ID NO 22
<211> LENGTH: 22
<212> TYPE: DNA
<213> ORGANISM: Artificial Sequence
<220> FEATURE:
<223> OTHER INFORMATION: synthetic qMSP EMX2 probe
<221> NAME/KEY: modified_base
<222> LOCATION: (1)...(1)
<223> OTHER INFORMATION: t modified by 6-FAM
<221> NAME/KEY: modified_base
<222> LOCATION: (22)...(22)
<223> OTHER INFORMATION: g modified by TAMRA

<400> SEQUENCE: 22
tattcggtgt cgtcgtcgta cg                                           22

<210> SEQ ID NO 23
<211> LENGTH: 30
<212> TYPE: DNA
<213> ORGANISM: Artificial Sequence
<220> FEATURE:
<223> OTHER INFORMATION: synthetic qMSP ATCB probe

<400> SEQUENCE: 23
accaccaccc aacacacaat aacaaacaca                                   30

<210> SEQ ID NO 24
<211> LENGTH: 22
<212> TYPE: DNA
<213> ORGANISM: Artificial Sequence
<220> FEATURE:
<223> OTHER INFORMATION: synthetic qMSP EMX2 probe

<400> SEQUENCE: 24
tattcggtgt cgtcgtcgta cg                                           22

<210> SEQ ID NO 25
<211> LENGTH: 29
<212> TYPE: DNA
<213> ORGANISM: Artificial Sequence
<220> FEATURE:
<223> OTHER INFORMATION: synthetic targeted beta-catenin gene sequence

<400> SEQUENCE: 25
ggtcctctgt gaacttgctc aggacaagg                                    29
```

```
<210> SEQ ID NO 26
<211> LENGTH: 29
<212> TYPE: DNA
<213> ORGANISM: Artificial Sequence
<220> FEATURE:
<223> OTHER INFORMATION: synthetic targeted beta-catenin gene sequence

<400> SEQUENCE: 26
ggctggtatc tcagaaagtg cctgacaca                                          29

<210> SEQ ID NO 27
<211> LENGTH: 29
<212> TYPE: DNA
<213> ORGANISM: Artificial Sequence
<220> FEATURE:
<223> OTHER INFORMATION: synthetic targeted EMX2 gene sequence

<400> SEQUENCE: 27
tcaagccatt taccaggctt cggaggaag                                          29

<210> SEQ ID NO 28
<211> LENGTH: 29
<212> TYPE: DNA
<213> ORGANISM: Artificial Sequence
<220> FEATURE:
<223> OTHER INFORMATION: synthetic targeted EMX2 gene sequence

<400> SEQUENCE: 28
cggtggagaa tcgccaccaa gcaggcgag                                          29
```